(12) United States Patent
Bonutti

(10) Patent No.: US 9,192,395 B2
(45) Date of Patent: Nov. 24, 2015

(54) ROBOTIC FASTENING SYSTEM

(71) Applicant: P Tech, LLC, Effingham, IL (US)

(72) Inventor: Peter M Bonutti, Delray Beach, FL (US)

(73) Assignee: P Tech, LLC, Effingham, IL (US)

( * ) Notice: Subject to any disclaimer, the term of this patent is extended or adjusted under 35 U.S.C. 154(b) by 0 days.

(21) Appl. No.: 13/888,957

(22) Filed: May 7, 2013

(65) Prior Publication Data

US 2013/0274760 A1    Oct. 17, 2013

Related U.S. Application Data

(63) Continuation of application No. 10/102,413, filed on Mar. 20, 2002.

(51) Int. Cl.
*A61B 17/00* (2006.01)
*A61B 17/16* (2006.01)
(Continued)

(52) U.S. Cl.
CPC ......... *A61B 17/1626* (2013.01); *A61B 17/0401* (2013.01); *A61B 17/0644* (2013.01);
(Continued)

(58) Field of Classification Search
CPC ............ A61B 17/068; A61B 17/128–17/1285; A61B 19/22; A61B 19/5225; A61B 19/5244; A61B 1/00; A61B 2017/2932; A61B 2019/464–2019/466; A61B 2019/4857; A61B 17/1626; A61B 19/2203; A61B 17/0644; A61B 17/0401; A61B 19/54; A61B 2017/0648; A61B 2019/2207; A61B 17/154; A61B 2017/00557; A61B 2019/465; A61B 19/50; A61F 2/0063

USPC ........ 606/232–233, 144–148, 1, 130; 227/19; 128/898; 173/1–4
See application file for complete search history.

(56) References Cited

U.S. PATENT DOCUMENTS

| 319,296 A | 6/1885 | Molesworth |
| 668,878 A | 2/1901 | Jensen |

(Continued)

FOREIGN PATENT DOCUMENTS

| CA | 2641580 | 8/2007 |
| CA | 2660827 | 9/2008 |

(Continued)

OTHER PUBLICATIONS

Translation of DE9002844.9 with translator's certificate dated Sept 26, 2013 (cited in IPR 2013-00631, 2013-00632).

(Continued)

*Primary Examiner* — Amy R Weisberg

(57) ABSTRACT

An improved apparatus and method of securing body tissue may be performed with a robotic mechanism. The robotic mechanism may be utilized to tension a suture with a predetermined force and urge a suture retainer toward body tissue with a predetermined force. Ultrasonic vibratory energy may be transmitted to the suture retainer to effect a gripping of the suture by the suture retainer. The body tissue may be secured with a staple. Legs of the staple may be bonded together to secure the staple. The legs of the staple may be bonded together by transmitting ultrasonic vibratory energy to the legs of the staple. A tissue positioning assembly may be used to hold the body tissue in a desired position. Images of the body tissue being secured may be obtained using various known devices including one or more endoscopes, a fluoroscope, a magnetic resonance imaging device, and/or other known imaging devices.

7 Claims, 15 Drawing Sheets

(51) Int. Cl.
  *A61B 17/04* (2006.01)
  *A61B 17/064* (2006.01)
  *A61B 19/00* (2006.01)
  *A61F 2/00* (2006.01)
  *A61B 17/15* (2006.01)
  *A61B 17/88* (2006.01)

(52) U.S. Cl.
  CPC ........... *A61B19/2203* (2013.01); *A61F 2/0063* (2013.01); *A61B 17/154* (2013.01); *A61B 17/8875* (2013.01); *A61B 19/50* (2013.01); *A61B 19/5225* (2013.01); *A61B 19/54* (2013.01); *A61B 2017/00557* (2013.01); *A61B 2017/0648* (2013.01); *A61B 2019/2207* (2013.01); *A61B 2019/465* (2013.01)

(56) References Cited

U.S. PATENT DOCUMENTS

| | | |
|---|---|---|
| 668,879 A | 2/1901 | Miller |
| 702,789 A | 6/1902 | Gibson |
| 862,712 A | 8/1907 | Collins |
| 2,178,840 A | 11/1926 | Lorenian |
| 2,121,193 A | 12/1932 | Hanicke |
| 2,187,852 A | 8/1936 | Friddle |
| 2,199,025 A | 4/1940 | Conn |
| 2,235,419 A | 3/1941 | Callahan |
| 2,248,054 A | 7/1941 | Becker |
| 2,270,188 A | 1/1942 | Longfellow |
| 2,518,276 A | 8/1950 | Braward |
| 2,557,669 A | 6/1951 | Lloyd |
| 2,566,499 A | 9/1951 | Richter |
| 2,621,653 A | 12/1952 | Briggs |
| 2,725,053 A | 11/1955 | Bambara |
| 2,830,587 A | 4/1958 | Everett |
| 3,204,635 A | 9/1965 | Voss |
| 3,347,234 A | 10/1967 | Voss |
| 3,391,690 A | 7/1968 | Armao |
| 3,477,429 A | 11/1969 | Sampson |
| 3,513,848 A | 5/1970 | Winston |
| 3,518,993 A | 7/1970 | Blake |
| 3,577,991 A | 5/1971 | Wilkinson |
| 3,596,292 A | 8/1971 | Erb |
| 3,608,539 A | 9/1971 | Miller |
| 3,625,220 A | 12/1971 | Engelsher |
| 3,648,705 A | 3/1972 | Lary |
| 3,653,388 A | 4/1972 | Tenckhoff |
| 3,656,476 A | 4/1972 | Swinney |
| 3,657,056 A | 4/1972 | Winston |
| 3,678,980 A | 7/1972 | Gutshall |
| 3,709,218 A | 1/1973 | Halloran |
| 3,711,347 A | 1/1973 | Wagner |
| 3,739,773 A | 6/1973 | Schmitt |
| 3,760,808 A | 9/1973 | Bleuer |
| 3,788,318 A | 1/1974 | Kim |
| 3,789,852 A | 2/1974 | Kim |
| 3,802,438 A | 4/1974 | Wolvek |
| 3,807,394 A | 4/1974 | Attenborough |
| 3,809,075 A | 5/1974 | Matles |
| 3,811,449 A | 5/1974 | Gravlee |
| 3,825,010 A | 7/1974 | McDonald |
| 3,833,003 A | 9/1974 | Taricco |
| 3,835,849 A | 9/1974 | McGuire |
| 3,842,824 A | 10/1974 | Neufeld |
| 3,845,772 A | 11/1974 | Smith |
| 3,857,396 A | 12/1974 | Hardwick |
| 3,867,932 A | 2/1975 | Huene |
| 3,875,652 A | 4/1975 | Arnold |
| 3,898,992 A | 8/1975 | Balamuth |
| 3,918,442 A | 11/1975 | Nikolaev |
| 3,968,800 A | 7/1976 | Vilasi |
| 3,976,079 A | 8/1976 | Samuels |
| 4,023,559 A | 5/1977 | Gaskell |
| 4,064,566 A | 12/1977 | Fletcher |
| 4,089,071 A | 5/1978 | Kainberz |
| 4,156,574 A | 5/1979 | Boden |
| 4,164,794 A | 8/1979 | Spector |
| 4,171,544 A | 10/1979 | Hench |
| 4,183,102 A | 1/1980 | Guiset |
| 4,199,864 A | 4/1980 | Ashman |
| 4,200,939 A | 5/1980 | Oser |
| 4,210,148 A | 7/1980 | Stivala |
| 4,213,816 A | 7/1980 | Morris |
| 4,235,233 A | 11/1980 | Mouwen |
| 4,235,238 A | 11/1980 | Ogiu |
| 4,244,370 A | 1/1981 | Furlow |
| 4,257,411 A | 3/1981 | Cho |
| 4,265,231 A | 5/1981 | Scheller |
| 4,281,649 A | 8/1981 | Derweduwen |
| 4,291,698 A | 9/1981 | Fuchs |
| 4,309,488 A | 1/1982 | Heide |
| 4,320,762 A | 3/1982 | Bentov |
| 4,351,069 A | 9/1982 | Ballintyn |
| 4,364,381 A | 12/1982 | Sher |
| 4,365,356 A | 12/1982 | Broemer |
| 4,388,921 A | 6/1983 | Sutter |
| 4,395,798 A | 8/1983 | McVey |
| 4,409,974 A | 10/1983 | Freedland |
| 4,414,166 A | 11/1983 | Carlson |
| 4,437,191 A | 3/1984 | van der Zat |
| 4,437,362 A | 3/1984 | Hurst |
| 4,444,180 A | 4/1984 | Schneider |
| 4,448,194 A | 5/1984 | DiGiovanni |
| 4,456,005 A | 6/1984 | Lichty |
| 4,461,281 A | 7/1984 | Carson |
| 4,493,317 A | 1/1985 | Klaue |
| 4,495,664 A | 1/1985 | Bianquaert |
| 4,501,031 A | 2/1985 | McDaniel |
| 4,504,268 A | 3/1985 | Herlitze |
| 4,506,681 A | 3/1985 | Mundell |
| 4,514,125 A | 4/1985 | Stol |
| 4,526,173 A | 7/1985 | Sheehan |
| 4,532,926 A | 8/1985 | O'Holla |
| 4,535,772 A | 8/1985 | Sheehan |
| 4,547,327 A | 10/1985 | Bruins |
| 4,556,059 A | 12/1985 | Adamson |
| 4,556,350 A | 12/1985 | Bernhardt |
| 4,566,138 A | 1/1986 | Lewis |
| 3,367,809 A | 5/1986 | Soloff |
| 4,589,868 A | 5/1986 | Dretler |
| 4,590,928 A | 5/1986 | Hunt |
| 4,597,379 A | 7/1986 | Kihn et al. |
| 4,599,085 A | 7/1986 | Riess |
| 4,601,893 A | 7/1986 | Cardinal |
| 4,606,335 A | 8/1986 | Wedeen |
| 4,611,593 A | 9/1986 | Fogarty |
| 4,621,640 A | 11/1986 | Mulhollan et al. |
| 4,630,609 A | 12/1986 | Chin |
| 4,632,101 A | 12/1986 | Freedland |
| 4,645,503 A | 2/1987 | Lin |
| 4,657,460 A | 4/1987 | Bien |
| 4,659,268 A | 4/1987 | del Mundo |
| 4,662,063 A | 5/1987 | Collins |
| 4,662,068 A | 5/1987 | Polonsky |
| 4,662,887 A | 5/1987 | Turner |
| 4,669,473 A | 6/1987 | Richards |
| 4,681,107 A | 7/1987 | Kees |
| 4,685,458 A | 8/1987 | Leckrone |
| 4,691,741 A | 9/1987 | Affa |
| 4,705,040 A | 11/1987 | Mueller |
| 4,706,670 A | 11/1987 | Andersen |
| 4,708,139 A | 11/1987 | Dunbar |
| 4,713,077 A | 12/1987 | Small |
| 4,716,901 A | 1/1988 | Jackson |
| 4,718,909 A | 1/1988 | Brown |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble |
| 4,739,751 A | 4/1988 | Sapega |
| 4,741,330 A | 5/1988 | Hayhurst |
| 4,749,585 A | 6/1988 | Greco |
| 4,750,492 A | 6/1988 | Jacobs |

(56) References Cited

U.S. PATENT DOCUMENTS

| | | |
|---|---|---|
| 4,768,507 A | 9/1988 | Fischell |
| 4,772,286 A | 9/1988 | Goble |
| 4,776,328 A | 10/1988 | Frey |
| 4,776,738 A | 10/1988 | Winston |
| 4,776,851 A | 10/1988 | Bruchman |
| 4,781,182 A | 11/1988 | Purnell |
| 4,790,303 A | 12/1988 | Steffee |
| 4,792,336 A | 12/1988 | Hiavacek |
| 4,817,591 A | 4/1989 | Klause |
| 4,822,224 A | 4/1989 | Carl |
| 4,823,794 A | 4/1989 | Pierce |
| 4,832,025 A | 5/1989 | Coates |
| 4,832,026 A | 5/1989 | Jones |
| 4,834,752 A | 5/1989 | VanKampen |
| 4,841,960 A | 6/1989 | Garner |
| 4,843,112 A | 6/1989 | Gerhart |
| 4,846,812 A | 7/1989 | Walker |
| 4,862,882 A | 9/1989 | Venturi |
| 4,869,242 A | 9/1989 | Galluzzo |
| 4,870,957 A | 10/1989 | Goble |
| 4,883,048 A | 11/1989 | Purnell |
| 4,890,612 A | 1/1990 | Kensey |
| 4,895,148 A | 1/1990 | Bays |
| 4,898,156 A | 2/1990 | Gattuma |
| 4,899,729 A | 2/1990 | Gill |
| 4,899,743 A | 2/1990 | Nicholson |
| 4,899,744 A | 2/1990 | Fujitsuka |
| 4,901,721 A | 2/1990 | Hakki |
| 4,921,479 A | 5/1990 | Grayzel |
| 4,922,897 A | 5/1990 | Sapega |
| 4,924,865 A | 5/1990 | Bays |
| 4,924,866 A | 5/1990 | Yoon |
| 4,932,960 A | 6/1990 | Green |
| 4,935,026 A | 6/1990 | McFadden |
| 4,935,028 A | 6/1990 | Drews |
| 4,945,625 A | 8/1990 | Winston |
| 4,946,468 A | 8/1990 | Li |
| 4,954,126 A | 9/1990 | Wallsten |
| 4,955,910 A | 9/1990 | Bolesky |
| 4,957,498 A | 9/1990 | Caspari et al. |
| 4,961,741 A | 10/1990 | Hayhurt |
| 4,963,151 A | 10/1990 | Ducheyne |
| 4,964,862 A | 10/1990 | Arms |
| 4,966,583 A | 10/1990 | Debbas |
| 4,968,315 A | 11/1990 | Gattuma |
| 4,969,888 A | 11/1990 | Scholten |
| 4,969,892 A | 11/1990 | Burton |
| 4,990,161 A | 2/1991 | Kampner |
| 4,994,071 A | 2/1991 | MacGregor |
| 4,997,445 A | 3/1991 | Hodorek |
| 4,998,539 A | 3/1991 | Delsanti |
| 5,002,550 A | 3/1991 | Li |
| 5,002,563 A | 3/1991 | Pyka |
| 5,009,652 A | 4/1991 | Morgan |
| 5,009,663 A | 4/1991 | Broome |
| 5,009,664 A | 4/1991 | Sievers |
| 5,013,316 A | 5/1991 | Goble |
| 5,019,090 A | 5/1991 | Pinchuk |
| 5,021,059 A | 6/1991 | Kensey |
| 5,031,841 A * | 7/1991 | Schafer .................. 239/584 |
| 5,035,713 A | 7/1991 | Friis |
| 5,037,404 A | 8/1991 | Gold |
| 5,037,422 A | 8/1991 | Hayhurst |
| 5,041,093 A | 8/1991 | Chu |
| 5,041,114 A | 8/1991 | Chapman |
| 5,041,129 A | 8/1991 | Hayhurst |
| 5,046,513 A | 9/1991 | Gattuma |
| 5,047,055 A | 9/1991 | Bao |
| 5,051,049 A | 9/1991 | Wills |
| 5,053,046 A | 10/1991 | Janese |
| 5,053,047 A | 10/1991 | Yoon |
| 5,059,193 A | 10/1991 | Kuslich |
| 5,059,206 A | 10/1991 | Winters |
| 5,061,274 A | 10/1991 | Kensey |
| 5,061,286 A | 10/1991 | Lyle |
| 5,069,674 A | 12/1991 | Farnot |
| 5,078,731 A | 1/1992 | Hayhurst |
| 5,078,744 A | 1/1992 | Chvapil |
| 5,078,745 A | 1/1992 | Rhenter |
| 5,084,050 A | 1/1992 | Draenert |
| 5,084,051 A | 1/1992 | Tormala |
| 5,085,660 A | 2/1992 | Lin |
| 5,085,661 A | 2/1992 | Moss |
| 5,086,401 A | 2/1992 | Glassman |
| 5,090,072 A | 2/1992 | Gray |
| 5,098,433 A | 3/1992 | Freedland |
| 5,098,434 A | 3/1992 | Serbousek |
| 5,098,436 A | 3/1992 | Ferrante |
| 5,100,405 A | 3/1992 | McLaren |
| 5,100,417 A | 3/1992 | Cerier |
| 5,102,417 A | 4/1992 | Palmaz |
| 5,102,421 A | 4/1992 | Anspach |
| 5,108,399 A | 4/1992 | Eitenmuller |
| 5,120,175 A | 6/1992 | Arbegast |
| 5,123,520 A | 6/1992 | Schmid |
| 5,123,914 A | 6/1992 | Cope |
| 5,123,941 A | 6/1992 | Lauren |
| 5,133,732 A | 7/1992 | Wiktor |
| RE34,021 E | 8/1992 | Mueller |
| 5,141,520 A | 8/1992 | Goble |
| 5,147,362 A | 9/1992 | Goble |
| 5,152,765 A | 10/1992 | Ross |
| 5,154,720 A | 10/1992 | Trott |
| 5,156,613 A | 10/1992 | Sawyer |
| 5,156,616 A | 10/1992 | Meadows |
| 5,158,566 A | 10/1992 | Pianetti |
| 5,158,934 A | 10/1992 | Ammann |
| 5,163,960 A | 11/1992 | Bonutti |
| 5,171,251 A | 12/1992 | Bregen |
| 5,176,682 A | 1/1993 | Chow |
| 5,179,964 A | 1/1993 | Cook |
| 5,180,388 A | 1/1993 | DiCarlo |
| 5,183,464 A | 2/1993 | Dubrul |
| 5,192,287 A | 3/1993 | Fournier |
| 5,192,326 A | 3/1993 | Bao |
| 5,197,166 A | 3/1993 | Meier |
| 5,197,971 A | 3/1993 | Bonutti |
| 5,203,784 A | 4/1993 | Ross |
| 5,203,787 A | 4/1993 | Noblitt |
| 5,208,950 A | 5/1993 | Merritt |
| 5,209,776 A | 5/1993 | Bass |
| 5,217,486 A | 6/1993 | Rice |
| 5,217,493 A | 6/1993 | Raad |
| 5,219,359 A | 6/1993 | McQuilkin |
| 5,224,946 A | 7/1993 | Hayhurst |
| 5,226,899 A | 7/1993 | Lee |
| 5,230,352 A * | 7/1993 | Putnam et al. ................ 128/898 |
| 5,234,006 A | 8/1993 | Eaton |
| 5,234,425 A | 8/1993 | Fogarty |
| 5,236,438 A | 8/1993 | Wilk |
| 5,236,445 A | 8/1993 | Hayhurst |
| 5,242,902 A | 9/1993 | Murphy |
| 5,246,441 A | 9/1993 | Ross |
| 5,250,026 A | 10/1993 | Ehrlich |
| 5,250,055 A | 10/1993 | Moore |
| 5,254,113 A | 10/1993 | Wilk |
| 5,258,007 A | 11/1993 | Spetzler et al. |
| 5,258,015 A | 11/1993 | Li |
| 5,258,016 A | 11/1993 | DiPoto |
| 5,261,914 A | 11/1993 | Warren |
| 5,266,325 A | 11/1993 | Kuzma |
| 5,269,783 A | 12/1993 | Sander |
| 5,269,785 A | 12/1993 | Bonutti |
| 5,269,809 A | 12/1993 | Hayhurst |
| 5,281,235 A | 1/1994 | Haber et al. |
| 5,282,832 A | 2/1994 | Toso |
| 5,290,281 A | 3/1994 | Tschakaloff |
| 5,304,119 A | 4/1994 | Balaban |
| 5,306,280 A | 4/1994 | Bregen |
| 5,306,301 A | 4/1994 | Graf |
| 5,312,438 A | 5/1994 | Johnson |
| 5,315,741 A | 5/1994 | Dubberke |
| 5,318,588 A | 6/1994 | Horzewski |
| 5,320,611 A | 6/1994 | Bonutti |

(56) References Cited

U.S. PATENT DOCUMENTS

| | | | |
|---|---|---|---|
| 5,324,308 A | 6/1994 | Pierce | |
| 5,328,480 A | 7/1994 | Melker | |
| 5,329,846 A | 7/1994 | Bonutti | |
| 5,329,924 A | 7/1994 | Bonutti | |
| 5,330,468 A | 7/1994 | Burkhart | |
| 5,330,476 A | 7/1994 | Hiot | |
| 5,330,486 A | 7/1994 | Wilk | |
| 5,336,231 A | 8/1994 | Adair | |
| 5,336,240 A | 8/1994 | Metzler | |
| 5,339,799 A | 8/1994 | Kami | |
| 5,343,385 A | 8/1994 | Joskowicz | |
| 5,349,956 A | 9/1994 | Bonutti | |
| 5,352,229 A | 10/1994 | Goble | |
| 5,354,298 A | 10/1994 | Lee | |
| 5,354,302 A | 10/1994 | Ko | |
| 5,366,480 A | 11/1994 | Corriveaau | |
| 5,370,646 A | 12/1994 | Reese | |
| 5,370,660 A | 12/1994 | Weomsteom | |
| 5,372,146 A | 12/1994 | Branchy | |
| 5,374,235 A | 12/1994 | Ahrens | |
| 5,376,126 A | 12/1994 | Lin | |
| 5,382,254 A | 1/1995 | McGarry | |
| 5,383,883 A | 1/1995 | Wilk | |
| 5,383,905 A | 1/1995 | Golds | |
| 5,391,171 A | 2/1995 | Schmieding | |
| 5,391,173 A | 2/1995 | Wilk | |
| 5,395,308 A | 3/1995 | Fox | |
| 5,397,311 A | 3/1995 | Walker | |
| 5,400,805 A | 3/1995 | Warren | |
| 5,403,312 A | 4/1995 | Yates | |
| 5,403,348 A | 4/1995 | Bonutti | |
| 5,405,359 A | 4/1995 | Pierce | |
| 5,411,523 A | 5/1995 | Goble | |
| 5,413,585 A | 5/1995 | Pagedas | |
| 5,417,691 A | 5/1995 | Hayhurst | |
| 5,417,701 A | 5/1995 | Holmes | |
| 5,417,712 A | 5/1995 | Whittaker | |
| 5,423,796 A | 6/1995 | Skikhman | |
| 5,423,860 A | 6/1995 | Lizardi | |
| 5,431,670 A | 7/1995 | Holmes | |
| 5,438,746 A | 8/1995 | Demarest | |
| 5,439,470 A | 8/1995 | Li | |
| 5,441,502 A | 8/1995 | Bartlett | |
| 5,441,538 A | 8/1995 | Bonutti | |
| 5,443,512 A | 8/1995 | Parr | |
| 5,447,503 A | 9/1995 | Miller | |
| 5,449,372 A | 9/1995 | Schmaltz | |
| 5,449,382 A | 9/1995 | Dayton | |
| 5,451,235 A | 9/1995 | Lock | |
| 5,453,090 A | 9/1995 | Martinez | |
| 5,456,722 A | 10/1995 | McLeod | |
| 5,458,653 A | 10/1995 | Davison | |
| 5,462,561 A | 10/1995 | Voda | |
| 5,464,424 A | 11/1995 | O'Donnell | |
| 5,464,425 A | 11/1995 | Skiba | |
| 5,464,426 A | 11/1995 | Bonutti | |
| 5,464,427 A | 11/1995 | Curtis | |
| 5,467,911 A * | 11/1995 | Tsuruta et al. | 227/175.1 |
| 5,470,337 A | 11/1995 | Moss | |
| 5,472,444 A | 12/1995 | Huebner | |
| 5,474,554 A | 12/1995 | Ku | |
| 5,478,351 A | 12/1995 | Meade | |
| 5,478,353 A | 12/1995 | Yoon | |
| 5,480,403 A | 1/1996 | Lee | |
| 5,486,197 A | 1/1996 | Le | |
| 5,487,216 A | 1/1996 | Demarest | |
| 5,487,844 A | 1/1996 | Fujita | |
| 5,488,958 A | 2/1996 | Topel | |
| 5,496,292 A | 3/1996 | Burnham | |
| 5,496,335 A | 3/1996 | Thomason et al. | |
| 5,496,348 A | 3/1996 | Bonutti | |
| 5,500,000 A | 3/1996 | Feagin | |
| 5,501,700 A | 3/1996 | Hirata | |
| 5,504,977 A | 4/1996 | Weppner | |
| 5,505,735 A | 4/1996 | Li | |
| 5,507,754 A | 4/1996 | Green | |
| 5,514,153 A | 5/1996 | Bonutti | |
| 5,518,163 A * | 5/1996 | Hooven | 227/5 |
| 5,518,164 A | 5/1996 | Hooven | |
| 5,520,700 A | 5/1996 | Beyar | |
| 5,522,844 A | 6/1996 | Johnson | |
| 5,522,845 A | 6/1996 | Wenstrom | |
| 5,522,846 A | 6/1996 | Bonutti | |
| 5,527,341 A | 6/1996 | Gogolewski | |
| 5,527,342 A | 6/1996 | Pietrzak | |
| 5,527,343 A | 6/1996 | Bonutti | |
| 5,528,884 A | 6/1996 | Johnson | |
| 5,529,075 A | 6/1996 | Clark | |
| 5,531,759 A | 7/1996 | Kensey | |
| 5,534,012 A | 7/1996 | Bonutti | |
| 5,534,028 A | 7/1996 | Bao | |
| 5,540,703 A | 7/1996 | Barker | |
| 5,540,718 A | 7/1996 | Bartkett | |
| 5,542,423 A | 8/1996 | Bonutti | |
| 5,545,178 A | 8/1996 | Kensey | |
| 5,545,180 A | 8/1996 | Le | |
| 5,545,206 A | 8/1996 | Carson | |
| 5,549,630 A | 8/1996 | Bonutti | |
| 5,549,631 A | 8/1996 | Bonutti | |
| 5,556,402 A | 9/1996 | Xu | |
| 5,562,688 A | 10/1996 | Riza | |
| 5,569,252 A | 10/1996 | Justin | |
| 5,569,305 A | 10/1996 | Bonutti | |
| 5,569,306 A | 10/1996 | Thal | |
| 5,573,517 A | 11/1996 | Bonutti | |
| 5,573,538 A | 11/1996 | Laboureau | |
| 5,573,542 A | 11/1996 | Stevens | |
| 5,575,801 A | 11/1996 | Habermeyer | |
| 5,580,344 A | 12/1996 | Hasson | |
| 5,584,835 A | 12/1996 | Greenfield | |
| 5,584,860 A | 12/1996 | Goble | |
| 5,584,862 A | 12/1996 | Bonutti | |
| 5,591,206 A | 1/1997 | Moufarrege | |
| 5,593,422 A | 1/1997 | Muijs van de Moer | |
| 5,593,425 A | 1/1997 | Bonutti | |
| 5,593,625 A | 1/1997 | Riebel | |
| 5,601,279 A | 2/1997 | Schwartz | |
| 5,601,557 A | 2/1997 | Hayhurst | |
| 5,601,558 A | 2/1997 | Torrie | |
| 5,607,427 A | 3/1997 | Tschakaloff | |
| 5,609,595 A | 3/1997 | Pennig | |
| 5,618,314 A | 4/1997 | Harwin | |
| 5,620,461 A | 4/1997 | Muijs van de Moer | |
| 5,626,612 A | 5/1997 | Bartlett | |
| 5,626,614 A | 5/1997 | Hart | |
| 5,626,718 A | 5/1997 | Philippe | |
| 5,628,446 A * | 5/1997 | Geiste et al. | 227/175.1 |
| 5,628,751 A | 5/1997 | Sander | |
| 5,628,756 A | 5/1997 | Barker | |
| 5,630,824 A | 5/1997 | Hart | |
| 5,634,926 A | 6/1997 | Jobe | |
| 5,643,274 A | 7/1997 | Sander | |
| 5,643,293 A | 7/1997 | Kogasaka | |
| 5,643,295 A | 7/1997 | Yoon | |
| 5,643,320 A | 7/1997 | Lower | |
| 5,643,321 A | 7/1997 | McDevitt | |
| 5,645,553 A | 7/1997 | Kolesa | |
| 5,645,597 A | 7/1997 | Krapiva | |
| 5,645,599 A | 7/1997 | Samani | |
| 5,649,940 A | 7/1997 | Hart | |
| 5,649,955 A | 7/1997 | Hashimoto | |
| 5,649,963 A | 7/1997 | McDevitt | |
| 5,651,377 A | 7/1997 | O'Donnell | |
| 5,658,313 A | 8/1997 | Thal | |
| 5,660,225 A | 8/1997 | Saffran | |
| 5,662,658 A | 9/1997 | Wenstrom | |
| 5,665,089 A | 9/1997 | Dall | |
| 5,665,109 A | 9/1997 | Yoon | |
| 5,665,112 A | 9/1997 | Thal | |
| 5,667,513 A | 9/1997 | Torrie | |
| 5,669,917 A | 9/1997 | Sauer | |
| 5,674,240 A | 10/1997 | Bonutti | |
| 5,680,981 A * | 10/1997 | Mililli et al. | 227/175.1 |
| 5,681,310 A | 10/1997 | Yuan | |

(56) References Cited

U.S. PATENT DOCUMENTS

| | | | |
|---|---|---|---|
| 5,681,333 A | 10/1997 | Burkhart | |
| 5,681,351 A | 10/1997 | Jamiolkowski | |
| 5,681,352 A | 10/1997 | Clancy | |
| 5,683,401 A | 11/1997 | Schmieding | |
| 5,683,418 A | 11/1997 | Luscombe | |
| 5,685,820 A | 11/1997 | Riek | |
| 5,688,283 A | 11/1997 | Knapp | |
| 5,690,654 A | 11/1997 | Ovil | |
| 5,690,655 A | 11/1997 | Hart | |
| 5,690,674 A | 11/1997 | Diaz | |
| 5,690,676 A | 11/1997 | DiPoto | |
| 5,693,055 A | 12/1997 | Zahiri | |
| 5,697,950 A | 12/1997 | Fucci | |
| 5,702,397 A | 12/1997 | Gonle | |
| 5,702,462 A | 12/1997 | Oberlander | |
| 5,707,395 A | 1/1998 | Li | |
| 5,713,903 A | 2/1998 | Sander | |
| 5,713,921 A | 2/1998 | Bonutti | |
| 5,718,717 A | 2/1998 | Bonutti | |
| 5,720,747 A | 2/1998 | Burke | |
| 5,720,753 A | 2/1998 | Sander | |
| 5,725,529 A | 3/1998 | Nicholson | |
| 5,725,541 A | 3/1998 | Anspach | |
| 5,725,556 A | 3/1998 | Moser | |
| 5,725,582 A | 3/1998 | Bevan | |
| 5,730,747 A | 3/1998 | Ek | |
| 5,733,306 A | 3/1998 | Bonutti | |
| 5,735,875 A | 4/1998 | Bonutti | |
| 5,735,877 A | 4/1998 | Pagedas | |
| 5,735,899 A | 4/1998 | Schwartz | |
| 5,741,268 A | 4/1998 | Schutz | |
| 5,741,282 A | 4/1998 | Anspach | |
| 5,752,952 A | 5/1998 | Adamson | |
| 5,752,974 A | 5/1998 | Rhee | |
| 5,755,809 A | 5/1998 | Cohen | |
| 5,762,458 A | 6/1998 | Wang | |
| 5,766,126 A | 6/1998 | Anderson | |
| 5,766,221 A | 6/1998 | Benderev | |
| 5,769,894 A | 6/1998 | Ferragamo | |
| 5,772,672 A | 6/1998 | Toy | |
| 5,776,151 A | 7/1998 | Chan | |
| 5,779,706 A | 7/1998 | Tschakaloff | |
| 5,779,719 A | 7/1998 | Klein | |
| 5,782,862 A | 7/1998 | Bonutti | |
| 5,785,713 A | 7/1998 | Jobe | |
| 5,792,096 A | 8/1998 | Rentmeester | |
| 5,797,931 A | 8/1998 | Bito | |
| 5,797,963 A | 8/1998 | McDevitt | |
| 5,800,537 A | 9/1998 | Bell | |
| 5,807,403 A | 9/1998 | Beyar | |
| 5,810,849 A | 9/1998 | Kontos | |
| 5,810,853 A | 9/1998 | Yoon | |
| 5,810,884 A | 9/1998 | Kim | |
| 5,814,072 A | 9/1998 | Bonutti | |
| 5,814,073 A | 9/1998 | Bonutti | |
| 5,817,107 A | 10/1998 | Schaller | |
| 5,823,994 A | 10/1998 | Sharkey | |
| 5,824,009 A | 10/1998 | Fukuda et al. | |
| 5,830,125 A | 11/1998 | Scribner | |
| 5,836,897 A | 11/1998 | Sakural | |
| 5,839,899 A | 11/1998 | Robinson | |
| 5,843,178 A | 12/1998 | Vanney | |
| 5,844,142 A | 12/1998 | Blanch | |
| 5,845,645 A | 12/1998 | Bonutti | |
| 5,851,185 A | 12/1998 | Berns | |
| 5,855,583 A * | 1/1999 | Wang et al. | 606/139 |
| 5,865,728 A | 2/1999 | Moll | |
| 5,865,834 A | 2/1999 | McGuire | |
| 5,866,634 A | 2/1999 | Tokushige | |
| 5,868,749 A | 2/1999 | Reed | |
| 5,873,212 A | 2/1999 | Esteves | |
| 5,873,891 A | 2/1999 | Sohn | |
| 5,874,235 A | 2/1999 | Chan | |
| 5,876,325 A | 3/1999 | Mizuno | |
| 5,879,371 A | 3/1999 | Gardiner | |
| 5,879,372 A | 3/1999 | Bartlett | |
| 5,891,166 A | 4/1999 | Schervinsky | |
| 5,891,168 A | 4/1999 | Thal | |
| 5,893,880 A | 4/1999 | Egan | |
| 5,897,574 A | 4/1999 | Bonutti | |
| 5,899,911 A | 5/1999 | Carter | |
| 5,899,921 A | 5/1999 | Caspari | |
| 5,906,579 A | 5/1999 | Vander | |
| 5,906,625 A | 5/1999 | Bito | |
| 5,908,429 A | 6/1999 | Yoon | |
| 5,911,449 A | 6/1999 | Daniele | |
| 5,911,721 A | 6/1999 | Nicholson | |
| 5,915,751 A | 6/1999 | Esteves | |
| 5,918,604 A | 7/1999 | Whelan | |
| 5,919,193 A | 7/1999 | Slavitt | |
| 5,919,194 A | 7/1999 | Anderson | |
| 5,919,208 A | 7/1999 | Valenti | |
| 5,919,215 A | 7/1999 | Wiklund et al. | |
| 5,921,986 A | 7/1999 | Bonutti | |
| 5,924,976 A * | 7/1999 | Stelzer et al. | 600/106 |
| 5,925,064 A | 7/1999 | Meyers et al. | |
| 5,928,244 A | 7/1999 | Tovey | |
| 5,928,267 A * | 7/1999 | Bonutti et al. | 606/216 |
| 5,931,838 A | 8/1999 | Vito | |
| 5,931,869 A | 8/1999 | Boucher | |
| 5,937,504 A | 8/1999 | Esteves | |
| 5,940,942 A | 8/1999 | Fong | |
| 5,941,900 A | 8/1999 | Bonutti | |
| 5,941,901 A | 8/1999 | Egan | |
| 5,947,982 A | 9/1999 | Duran | |
| 5,948,000 A | 9/1999 | Larsen | |
| 5,948,001 A | 9/1999 | Larsen | |
| 5,948,002 A | 9/1999 | Bonutti | |
| 5,951,590 A | 9/1999 | Goldfarb | |
| 5,956,927 A | 9/1999 | Daniele | |
| 5,957,953 A | 9/1999 | DiPoto | |
| 5,961,499 A | 10/1999 | Bonutti | |
| 5,961,521 A | 10/1999 | Roger | |
| 5,961,538 A | 10/1999 | Pedlick | |
| 5,961,554 A | 10/1999 | Janson | |
| 5,964,075 A | 10/1999 | Daniele | |
| 5,964,765 A | 10/1999 | Fenton | |
| 5,964,769 A | 10/1999 | Wagner | |
| 5,967,970 A | 10/1999 | Cowan | |
| 5,968,046 A | 10/1999 | Castleman | |
| 5,968,047 A | 10/1999 | Reed | |
| 5,970,686 A | 10/1999 | Demarest | |
| 5,976,156 A | 11/1999 | Taylor | |
| 5,980,520 A | 11/1999 | Vancaillie | |
| 5,980,558 A | 11/1999 | Wiley | |
| 5,980,559 A | 11/1999 | Bonutti | |
| 5,983,601 A | 11/1999 | Blanch | |
| 5,984,929 A | 11/1999 | Bashiri | |
| 5,987,848 A | 11/1999 | Blanch | |
| 5,989,282 A | 11/1999 | Bonutti | |
| 5,993,458 A | 11/1999 | Vaitekunas | |
| 5,993,477 A | 11/1999 | Vaitekunas | |
| 6,007,567 A | 12/1999 | Bonutti | |
| 6,007,580 A | 12/1999 | Lehto | |
| 6,010,525 A | 1/2000 | Bonutti | |
| 6,010,526 A | 1/2000 | Sandstrom | |
| 6,012,216 A | 1/2000 | Esteves | |
| 6,014,851 A | 1/2000 | Daniele | |
| 6,017,321 A | 1/2000 | Boone | |
| 6,032,343 A | 3/2000 | Blanch | |
| 6,033,415 A | 3/2000 | Mittelstadt | |
| 6,033,429 A | 3/2000 | Magovern | |
| 6,033,430 A | 3/2000 | Bonutti | |
| 6,045,551 A | 4/2000 | Bonutti | |
| 6,050,998 A | 4/2000 | Fletcher | |
| 6,056,751 A | 5/2000 | Fenton | |
| 6,056,772 A | 5/2000 | Bonutti | |
| 6,056,773 A | 5/2000 | Bonutti | |
| 6,059,797 A | 5/2000 | Mears | |
| 6,059,817 A | 5/2000 | Bonutti | |
| 6,059,827 A | 5/2000 | Fenton | |
| 6,063,095 A | 5/2000 | Wang | |
| 6,066,151 A | 5/2000 | Miyawaki | |
| 6,066,160 A | 5/2000 | Colvin | |

(56) References Cited

U.S. PATENT DOCUMENTS

| | | |
|---|---|---|
| 6,066,166 A | 5/2000 | Bischoff |
| 6,068,637 A | 5/2000 | Popov |
| 6,068,648 A | 5/2000 | Cole |
| 6,074,409 A | 6/2000 | Goldfarb |
| 6,077,277 A | 6/2000 | Mollenauer |
| 6,077,292 A | 6/2000 | Bonutti |
| 6,080,161 A | 6/2000 | Eaves |
| 6,081,981 A | 7/2000 | Demarest |
| 6,083,244 A | 7/2000 | Lubbers |
| 6,083,522 A | 7/2000 | Chu |
| 6,086,593 A | 7/2000 | Bonutti |
| 6,086,608 A | 7/2000 | Ek |
| 6,090,072 A | 7/2000 | Kratoska |
| 6,099,531 A | 8/2000 | Bonutti |
| 6,099,537 A | 8/2000 | Sugai |
| 6,099,547 A | 8/2000 | Gellman |
| 6,099,550 A | 8/2000 | Yoon |
| 6,099,552 A | 8/2000 | Adams |
| 6,102,850 A | 8/2000 | Wang |
| 6,106,545 A | 8/2000 | Egan |
| 6,117,160 A | 9/2000 | Bonutti |
| 6,120,536 A | 9/2000 | Ding |
| 6,125,574 A | 10/2000 | Ganaja |
| 6,126,677 A | 10/2000 | Ganaja |
| 6,132,368 A * | 10/2000 | Cooper ............ 600/102 |
| 6,139,320 A | 10/2000 | Hahn |
| RE36,974 E | 11/2000 | Bonutti |
| 6,149,658 A | 11/2000 | Gardiner |
| 6,149,669 A | 11/2000 | Li |
| 6,152,949 A | 11/2000 | Bonutti |
| 6,155,756 A | 12/2000 | Mericle |
| 6,159,224 A | 12/2000 | Yoon |
| 6,159,234 A | 12/2000 | Bonutti |
| 6,171,307 B1 | 1/2001 | Orlich |
| 6,174,324 B1 | 1/2001 | Egan |
| 6,179,840 B1 | 1/2001 | Bowman |
| 6,179,850 B1 | 1/2001 | Goradia |
| 6,187,008 B1 | 2/2001 | Hamman |
| 6,190,400 B1 | 2/2001 | van de Moer |
| 6,190,401 B1 | 2/2001 | Green |
| 6,200,322 B1 | 3/2001 | Branch |
| 6,200,329 B1 | 3/2001 | Fung |
| 6,205,748 B1 | 3/2001 | Daniele |
| 6,217,591 B1 | 4/2001 | Egan |
| 6,224,593 B1 | 5/2001 | Ryan |
| 6,224,630 B1 | 5/2001 | Bao |
| 6,228,086 B1 | 5/2001 | Wahl |
| 6,231,565 B1 | 5/2001 | Tovey |
| 6,231,592 B1 | 5/2001 | Bonutti et al. |
| 6,238,395 B1 | 5/2001 | Bonutti |
| 6,241,749 B1 | 6/2001 | Rayhanabad |
| 6,246,200 B1 * | 6/2001 | Blumenkranz et al. .. 318/568.11 |
| 6,258,091 B1 | 7/2001 | Sevrain |
| 6,263,558 B1 | 7/2001 | Blanch |
| 6,264,675 B1 | 7/2001 | Brotz |
| 6,267,761 B1 | 7/2001 | Ryan |
| 6,273,717 B1 | 8/2001 | Hahn |
| 6,280,474 B1 | 8/2001 | Cassidy |
| 6,286,746 B1 | 9/2001 | Egan |
| 6,287,325 B1 | 9/2001 | Bonutti |
| 6,293,961 B2 | 9/2001 | Schwartz |
| 6,306,159 B1 | 10/2001 | Schwartz |
| 6,309,405 B1 | 10/2001 | Bonutti |
| 6,312,448 B1 | 11/2001 | Bonutti |
| 6,319,252 B1 | 11/2001 | McDevitt |
| 6,319,271 B1 | 11/2001 | Schwartz |
| 6,331,181 B1 * | 12/2001 | Tierney et al. ............ 606/130 |
| 6,338,730 B1 | 1/2002 | Bonutti |
| 6,340,365 B2 | 1/2002 | Dittrich et al. |
| 6,348,056 B1 | 2/2002 | Bates |
| 6,358,271 B1 | 3/2002 | Egan |
| 6,364,897 B1 | 4/2002 | Bonutti |
| 6,368,325 B1 | 4/2002 | McKinley |
| 6,368,326 B1 | 4/2002 | Dakin |
| 6,368,343 B1 | 4/2002 | Bonutti |
| 6,371,957 B1 | 4/2002 | Amrein |
| 6,409,742 B1 | 6/2002 | Fulton |
| 6,409,743 B1 | 6/2002 | Fenton |
| 6,419,704 B1 | 7/2002 | Ferree |
| 6,423,072 B1 * | 7/2002 | Zappala ............ 606/104 |
| 6,423,088 B1 | 7/2002 | Fenton |
| 6,425,919 B1 | 7/2002 | Lambrect |
| 6,428,562 B2 | 8/2002 | Bonutti |
| 6,432,115 B1 | 8/2002 | Mollenauer |
| 6,436,107 B1 | 8/2002 | Wang |
| 6,447,516 B1 | 9/2002 | Bonutti |
| 6,450,985 B1 | 9/2002 | Schoelling |
| 6,451,027 B1 * | 9/2002 | Cooper et al. ............ 606/130 |
| 6,461,360 B1 | 10/2002 | Adams |
| 6,468,265 B1 | 10/2002 | Evans |
| 6,468,293 B2 | 10/2002 | Bonutti |
| 6,471,715 B1 | 10/2002 | Weiss |
| 6,475,230 B1 | 11/2002 | Bonutti |
| 6,488,196 B1 * | 12/2002 | Fenton, Jr. ............ 227/175.1 |
| 6,500,195 B2 | 12/2002 | Bonutti |
| 6,503,259 B2 | 1/2003 | Huxel |
| 6,527,774 B2 | 3/2003 | Lieberman |
| 6,530,933 B1 | 3/2003 | Yeung |
| 6,533,157 B1 * | 3/2003 | Whitman ............ 227/175.1 |
| 6,535,764 B2 | 3/2003 | Imran |
| 6,544,267 B1 | 4/2003 | Cole |
| 6,545,390 B1 | 4/2003 | Hahn |
| 6,547,792 B1 | 4/2003 | Tsuji |
| 6,551,304 B1 | 4/2003 | Whalen |
| 6,554,852 B1 | 4/2003 | Oberlander |
| 6,557,426 B2 | 5/2003 | Reinemann |
| 6,558,390 B2 | 5/2003 | Cragg |
| 6,562,043 B1 | 5/2003 | Chan |
| 6,565,554 B1 * | 5/2003 | Niemeyer ............ 606/1 |
| 6,568,313 B2 | 5/2003 | Fukui |
| 6,569,167 B1 | 5/2003 | Bobechko |
| 6,569,187 B1 | 5/2003 | Bonutti |
| 6,572,635 B1 | 6/2003 | Bonutti |
| D477,776 S | 7/2003 | Pontaoe |
| 6,585,746 B2 | 7/2003 | Gildenberg |
| 6,585,750 B2 | 7/2003 | Bonutti |
| 6,585,764 B2 | 7/2003 | Wright |
| 6,592,609 B1 | 7/2003 | Bonutti |
| 6,594,517 B1 | 7/2003 | Nevo |
| 6,605,090 B1 | 8/2003 | Trieu |
| 6,610,080 B2 | 8/2003 | Morgan |
| 6,618,910 B1 | 9/2003 | Pontaoe |
| 6,623,486 B1 | 9/2003 | Weaver |
| 6,623,487 B1 | 9/2003 | Goshert |
| 6,626,944 B1 | 9/2003 | Taylor |
| 6,632,245 B2 | 10/2003 | Kim |
| 6,635,073 B2 | 10/2003 | Bonutti |
| 6,638,279 B2 | 10/2003 | Bonutti |
| 6,641,592 B1 | 11/2003 | Sauer |
| 6,645,227 B2 | 11/2003 | Fallin |
| 6,666,877 B2 | 12/2003 | Morgan |
| 6,669,705 B2 | 12/2003 | Westhaver |
| 6,676,669 B2 | 1/2004 | Charles |
| 6,679,888 B2 | 1/2004 | Green |
| 6,685,750 B1 | 2/2004 | Plos |
| 6,699,177 B1 | 3/2004 | Wang et al. |
| 6,699,240 B2 | 3/2004 | Francischelli |
| 6,702,821 B2 | 3/2004 | Bonutti |
| 6,705,179 B1 | 3/2004 | Mohtasham |
| 6,709,457 B1 | 3/2004 | Otte |
| 6,712,828 B2 * | 3/2004 | Schraft et al. ............ 606/144 |
| 6,719,765 B2 | 4/2004 | Bonutti |
| 6,719,797 B1 | 4/2004 | Ferree |
| 6,722,552 B2 | 4/2004 | Fenton |
| 6,731,988 B1 | 5/2004 | Green |
| 6,733,506 B1 | 5/2004 | McDevitt |
| 6,733,531 B1 | 5/2004 | Trieu |
| 6,764,514 B1 | 7/2004 | Li |
| 6,770,078 B2 | 8/2004 | Bonutti |
| 6,780,198 B1 | 8/2004 | Gregoire |
| 6,786,989 B2 | 9/2004 | Torriani |
| 6,796,003 B1 | 9/2004 | Marvel |
| 6,818,010 B2 | 11/2004 | Eichhorn |
| 6,823,871 B2 | 11/2004 | Schmieding |

(56) References Cited

U.S. PATENT DOCUMENTS

| | | | |
|---|---|---|---|
| 6,827,712 B2 | 12/2004 | Tovey | |
| 6,837,892 B2 | 1/2005 | Shoham | |
| 6,840,938 B1* | 1/2005 | Morley et al. | 606/51 |
| 6,843,403 B2* | 1/2005 | Whitman | 227/176.1 |
| 6,860,878 B2* | 3/2005 | Brock | 606/1 |
| 6,860,885 B2 | 3/2005 | Bonutti | |
| 6,869,437 B1* | 3/2005 | Hausen et al. | 606/153 |
| 6,878,167 B2 | 4/2005 | Ferree | |
| 6,884,264 B2 | 4/2005 | Spiegelberg | |
| 6,890,334 B2 | 5/2005 | Brace | |
| 6,893,434 B2 | 5/2005 | Fenton | |
| 6,899,722 B2 | 5/2005 | Bonutti | |
| 6,913,666 B1 | 7/2005 | Aesclimann | |
| 6,916,321 B2 | 7/2005 | TenHuisen | |
| 6,921,264 B2 | 7/2005 | Mayer | |
| 6,923,824 B2 | 8/2005 | Morgan | |
| 6,932,835 B2 | 8/2005 | Bonutti | |
| 6,942,684 B2 | 9/2005 | Bonutti | |
| 6,944,111 B2 | 9/2005 | Nakamura | |
| 6,955,540 B2 | 10/2005 | Mayer | |
| 6,955,683 B2 | 10/2005 | Bonutti | |
| 6,958,077 B2 | 10/2005 | Suddaby | |
| 6,981,983 B1 | 1/2006 | Rosenblatt | |
| 6,997,940 B2 | 2/2006 | Bonutti | |
| 7,001,411 B1 | 2/2006 | Dean | |
| 7,004,959 B2 | 2/2006 | Bonutti | |
| 7,008,226 B2 | 3/2006 | Mayer | |
| 7,018,380 B2 | 3/2006 | Cole | |
| 7,033,379 B2 | 4/2006 | Peterson | |
| 7,048,755 B2 | 5/2006 | Bonutti | |
| 7,066,960 B1 | 6/2006 | Dickman | |
| 7,087,073 B2 | 8/2006 | Bonutti | |
| 7,090,111 B2 | 8/2006 | Egan | |
| 7,090,683 B2 | 8/2006 | Brock | |
| 7,094,251 B2 | 8/2006 | Bonutti | |
| 7,104,996 B2 | 9/2006 | Bonutti | |
| 7,128,763 B1 | 10/2006 | Blatt | |
| 7,147,652 B2 | 12/2006 | Bonutti | |
| 7,153,312 B1 | 12/2006 | Torrie | |
| 7,160,405 B2 | 1/2007 | Aesclimann | |
| 7,179,259 B1 | 2/2007 | Gibbs | |
| 7,192,448 B2 | 3/2007 | Ferree | |
| 7,217,279 B2 | 5/2007 | Reese | |
| 7,217,290 B2 | 5/2007 | Bonutti | |
| 7,241,297 B2 | 7/2007 | Shaolian | |
| 7,250,051 B2 | 7/2007 | Francischelli | |
| 7,252,685 B2 | 8/2007 | Bindseil | |
| 7,273,497 B2 | 9/2007 | Ferree | |
| 7,297,142 B2 | 11/2007 | Brock | |
| 7,329,263 B2 | 2/2008 | Bonutti | |
| 7,335,205 B2 | 2/2008 | Aeschlimann | |
| 7,429,266 B2 | 9/2008 | Bonutti | |
| 7,445,634 B2 | 11/2008 | Trieu | |
| 7,481,825 B2 | 1/2009 | Bonutti | |
| 7,481,831 B2 | 1/2009 | Bonutti | |
| 7,510,895 B2 | 3/2009 | Raterman | |
| 7,854,750 B2 | 12/2010 | Bonutti | |
| 7,879,072 B2 | 2/2011 | Bonutti | |
| 7,891,691 B2 | 2/2011 | Bearey | |
| 7,967,820 B2 | 6/2011 | Bonutti | |
| 8,128,669 B2 | 3/2012 | Bonutti | |
| 8,140,982 B2 | 3/2012 | Hamilton | |
| 8,147,514 B2 | 4/2012 | Bonutti | |
| 8,162,977 B2 | 4/2012 | Bonutti | |
| 8,702,732 B2 | 4/2014 | Woodard | |
| 2001/0002440 A1 | 5/2001 | Bonutti | |
| 2001/0005975 A1* | 7/2001 | Golightly | 53/528 |
| 2001/0009250 A1 | 7/2001 | Herman | |
| 2001/0041916 A1 | 11/2001 | Bonutti | |
| 2002/0016593 A1 | 2/2002 | Hearn | |
| 2002/0016633 A1 | 2/2002 | Lin | |
| 2002/0019649 A1 | 2/2002 | Sikora | |
| 2002/0026244 A1 | 2/2002 | Trieu | |
| 2002/0029083 A1 | 3/2002 | Zucherman | |
| 2002/0029084 A1 | 3/2002 | Paul | |
| 2002/0045888 A1* | 4/2002 | Ramans et al. | 606/1 |
| 2002/0045902 A1 | 4/2002 | Bonutti | |
| 2002/0062136 A1* | 5/2002 | Hillstead et al. | 606/205 |
| 2002/0062153 A1 | 5/2002 | Paul | |
| 2002/0082612 A1* | 6/2002 | Moll et al. | 606/130 |
| 2002/0087048 A1* | 7/2002 | Brock et al. | 600/114 |
| 2002/0087049 A1* | 7/2002 | Brock et al. | 600/114 |
| 2002/0087148 A1* | 7/2002 | Brock et al. | 606/1 |
| 2002/0087166 A1* | 7/2002 | Brock et al. | 606/130 |
| 2002/0087169 A1* | 7/2002 | Brock et al. | 606/139 |
| 2002/0095175 A1* | 7/2002 | Brock et al. | 606/205 |
| 2002/0103495 A1 | 8/2002 | Cole | |
| 2002/0120252 A1* | 8/2002 | Brock et al. | 606/1 |
| 2002/0123750 A1 | 9/2002 | Eisermann | |
| 2002/0128633 A1 | 9/2002 | Brock | |
| 2002/0128661 A1* | 9/2002 | Brock et al. | 606/130 |
| 2002/0128662 A1* | 9/2002 | Brock et al. | 606/130 |
| 2002/0133173 A1* | 9/2002 | Brock et al. | 606/130 |
| 2002/0133174 A1* | 9/2002 | Charles et al. | 606/130 |
| 2002/0138082 A1* | 9/2002 | Brock et al. | 606/130 |
| 2002/0138109 A1* | 9/2002 | Keogh et al. | 607/9 |
| 2002/0143319 A1* | 10/2002 | Brock | 606/1 |
| 2002/0183762 A1 | 12/2002 | Anderson | |
| 2002/0188301 A1 | 12/2002 | Dallara | |
| 2003/0014064 A1* | 1/2003 | Blatter | 606/153 |
| 2003/0039196 A1 | 2/2003 | Nakamura | |
| 2003/0040758 A1 | 2/2003 | Wang | |
| 2003/0045900 A1* | 3/2003 | Hahnen et al. | 606/205 |
| 2003/0055409 A1* | 3/2003 | Brock | 606/1 |
| 2003/0060927 A1* | 3/2003 | Gerbi et al. | 700/245 |
| 2003/0065361 A1 | 4/2003 | Dreyfuss | |
| 2003/0105474 A1 | 6/2003 | Bonutti | |
| 2003/0118518 A1 | 6/2003 | Hahn | |
| 2003/0135204 A1* | 7/2003 | Lee et al. | 606/1 |
| 2003/0158582 A1 | 8/2003 | Bonutti | |
| 2003/0167072 A1 | 9/2003 | Oberlander | |
| 2003/0181800 A1 | 9/2003 | Bonutti | |
| 2003/0195530 A1 | 10/2003 | Thill | |
| 2003/0195565 A1 | 10/2003 | Bonutti | |
| 2003/0204204 A1 | 10/2003 | Bonutti | |
| 2003/0216742 A1 | 11/2003 | Wetzler | |
| 2003/0225438 A1 | 12/2003 | Bonutti | |
| 2003/0229361 A1 | 12/2003 | Jackson | |
| 2004/0010287 A1 | 1/2004 | Bonutti | |
| 2004/0030341 A1 | 2/2004 | Aeschlimann | |
| 2004/0034357 A1 | 2/2004 | Beane | |
| 2004/0097939 A1 | 5/2004 | Bonutti | |
| 2004/0098050 A1 | 5/2004 | Foerster | |
| 2004/0102804 A1* | 5/2004 | Chin | 606/190 |
| 2004/0138703 A1 | 7/2004 | Alleyne | |
| 2004/0143334 A1 | 7/2004 | Ferree | |
| 2004/0167548 A1 | 8/2004 | Bonutti | |
| 2004/0220616 A1 | 11/2004 | Bonutti | |
| 2004/0225325 A1 | 11/2004 | Bonutti | |
| 2004/0230223 A1 | 11/2004 | Bonutti | |
| 2004/0236374 A1 | 11/2004 | Bonutti | |
| 2004/0243109 A1 | 12/2004 | Tovey | |
| 2005/0033366 A1 | 2/2005 | Cole | |
| 2005/0038514 A1 | 2/2005 | Helm | |
| 2005/0043796 A1 | 2/2005 | Grant | |
| 2005/0071012 A1 | 3/2005 | Serhan | |
| 2005/0090827 A1 | 4/2005 | Gedebou | |
| 2005/0090840 A1* | 4/2005 | Gerbino et al. | 606/148 |
| 2005/0096699 A1 | 5/2005 | Wixey | |
| 2005/0113928 A1 | 5/2005 | Cragg | |
| 2005/0126680 A1 | 6/2005 | Aeschlimann | |
| 2005/0143826 A1 | 6/2005 | Zucherman | |
| 2005/0149024 A1 | 7/2005 | Ferrante | |
| 2005/0149029 A1 | 7/2005 | Bonutti | |
| 2005/0203521 A1 | 9/2005 | Bonutti | |
| 2005/0216059 A1 | 9/2005 | Bonutti | |
| 2005/0216087 A1 | 9/2005 | Zucherman | |
| 2005/0222620 A1 | 10/2005 | Bonutti | |
| 2005/0240190 A1 | 10/2005 | Gall | |
| 2005/0240227 A1 | 10/2005 | Bonutti | |
| 2005/0246021 A1 | 11/2005 | Ringelsen | |
| 2005/0261684 A1 | 11/2005 | Shaolian | |
| 2005/0267481 A1 | 12/2005 | Carl | |
| 2005/0267534 A1 | 12/2005 | Bonutti | |

(56) References Cited

U.S. PATENT DOCUMENTS

| | | | |
|---|---|---|---|
| 2006/0009855 A1 | 1/2006 | Goble | |
| 2006/0015101 A1 | 1/2006 | Warburton | |
| 2006/0015108 A1 | 1/2006 | Bonutti | |
| 2006/0024357 A1 | 2/2006 | Carpenter | |
| 2006/0026244 A1 | 2/2006 | Watson | |
| 2006/0064095 A1 | 3/2006 | Senn | |
| 2006/0089646 A1 | 4/2006 | Bonutti | |
| 2006/0122600 A1 | 6/2006 | Cole | |
| 2006/0122704 A1 | 6/2006 | Vresilovic | |
| 2006/0142657 A1* | 6/2006 | Quaid et al. | 600/424 |
| 2006/0142799 A1 | 6/2006 | Bonutti | |
| 2006/0161136 A1* | 7/2006 | Anderson et al. | 606/1 |
| 2006/0167495 A1 | 7/2006 | Bonutti | |
| 2006/0200199 A1 | 9/2006 | Bonutti | |
| 2006/0212073 A1 | 9/2006 | Bonutti | |
| 2006/0217765 A1 | 9/2006 | Bonutti | |
| 2006/0229623 A1 | 10/2006 | Bonutti | |
| 2006/0235470 A1 | 10/2006 | Bonutti | |
| 2006/0241695 A1 | 10/2006 | Bonutti | |
| 2006/0265009 A1 | 11/2006 | Bonutti | |
| 2006/0265011 A1 | 11/2006 | Bonutti | |
| 2007/0032825 A1 | 2/2007 | Bonutti | |
| 2007/0088340 A1* | 4/2007 | Brock et al. | 606/1 |
| 2007/0088362 A1 | 4/2007 | Bonutti | |
| 2007/0118129 A1 | 5/2007 | Fraser | |
| 2007/0198555 A1 | 8/2007 | Friedman | |
| 2007/0265561 A1 | 11/2007 | Yeung | |
| 2007/0270833 A1 | 11/2007 | Bonutti | |
| 2007/0287889 A1 | 12/2007 | Mohr | |
| 2008/0021474 A1 | 1/2008 | Bonutti | |
| 2008/0039845 A1 | 2/2008 | Bonutti | |
| 2008/0039873 A1 | 2/2008 | Bonutti | |
| 2008/0046090 A1 | 2/2008 | Paul | |
| 2008/0097448 A1 | 4/2008 | Binder | |
| 2008/0108897 A1 | 5/2008 | Bonutti | |
| 2008/0108916 A1 | 5/2008 | Bonutti | |
| 2008/0114399 A1 | 5/2008 | Bonutti | |
| 2008/0132950 A1 | 6/2008 | Lange | |
| 2008/0140088 A1* | 6/2008 | Orban, III | 606/130 |
| 2008/0140116 A1 | 6/2008 | Bonutti | |
| 2008/0140117 A1 | 6/2008 | Bonutti | |
| 2008/0195145 A1 | 8/2008 | Bonutti | |
| 2008/0269753 A1 | 10/2008 | Cannestra | |
| 2008/0269808 A1 | 10/2008 | Gall | |
| 2009/0024161 A1 | 1/2009 | Bonutti | |
| 2009/0093684 A1 | 4/2009 | Schorer | |
| 2009/0138014 A1 | 5/2009 | Bonutti | |
| 2009/0194969 A1 | 8/2009 | Bearey | |
| 2010/0211120 A1 | 8/2010 | Bonutti | |
| 2011/0060375 A1 | 3/2011 | Bonutti | |
| 2011/0144661 A1* | 6/2011 | Houser et al. | 606/142 |
| 2011/0295253 A1 | 12/2011 | Bonutti et al. | |
| 2012/0165841 A1 | 6/2012 | Bonutti | |
| 2012/0191140 A1 | 7/2012 | Bonutti | |
| 2012/0215233 A1 | 8/2012 | Bonutti | |

FOREIGN PATENT DOCUMENTS

| | | |
|---|---|---|
| CA | 2698057 | 3/2009 |
| DE | 1903016 U | 10/1964 |
| DE | 1903316 | 10/1964 |
| DE | 1903016 A1 | 8/1970 |
| DE | 3517204 | 11/1986 |
| DE | 3722538 | 1/1991 |
| DE | 9002844 U1 | 1/1991 |
| EP | 784454 | 5/1996 |
| EP | 773004 | 5/1997 |
| EP | 1614525 | 1/2006 |
| EP | 1988837 | 8/2007 |
| EP | 2134294 | 12/2009 |
| FR | 2717368 | 3/1994 |
| FR | 2696338 | 4/1994 |
| FR | 2728779 | 1/1995 |
| FR | 2736257 | 7/1995 |
| FR | 2750031 | 6/1996 |
| FR | 2771621 | 11/1997 |
| FR | 2785171 | 10/1998 |
| GB | 2093701 A | 9/1982 |
| GB | 2306110 A | 4/1997 |
| JP | 8140982 | 6/1996 |
| SU | 184396 | 7/1966 |
| WO | 9112779 | 9/1991 |
| WO | 9323094 | 11/1993 |
| WO | 9408642 | 4/1994 |
| WO | 9516398 | 6/1995 |
| WO | 9531941 | 11/1995 |
| WO | 9614802 | 5/1996 |
| WO | 9712779 | 4/1997 |
| WO | 9749347 | 12/1997 |
| WO | 9811838 | 3/1998 |
| WO | WO 98/26720 | 6/1998 |
| WO | 2002053011 | 7/2002 |
| WO | 2007092869 | 8/2007 |
| WO | 2008116203 | 9/2008 |
| WO | 2009029908 | 3/2009 |
| WO | 2010099222 | 2/2010 |

OTHER PUBLICATIONS

Declaration of Steve Jordan for USP 5921986, from IPR 2013-00632, dated Sep. 24, 2013 (exhibit 1010).
Declaration of Steve Jordan for USP 5921986, from IPR 2013-00633, dated Sep. 24, 2013 (exhibit 1007).
Declaration of Dr. Steve E. Jordan for USP 8, 147,514, from IPR 2013-00631, dated Sep. 23, 2013.
The Search for the Holy Grail: A Century of Anterior Cruciate Ligament Reconstruction, R. John Naranja, American Journal of Orthopedics, Nov. 1997.
Femoral Bone Plug Recession in Endoscope Anterior Cruciate Ligament Reconstruction, David E Taylor, Arthroscopy: The Journal of Arthroscopic and Related Surgery, Aug. 1996.
Meniscus Replacement with Bone Anchors: A Surgical Technique, Arthroscopy: The Journal of Arthroscopic and Related Surgery, 1994.
Problem Solving Report Question No. 1014984.066, Ultrasonic Welding, (c) 1999.
Guide to Ultrasound Plastic Assembly, Ultrasonic Division Publication, (c) 1995.
Branson, Polymers: Characteristics and Compatibility for Ultrasonic Assembly, Applied Technologies Group, Publication unknown.
Enabling Local Drug Delivery-Implant Device Combination Therapies, Surmodics, Inc., (c) 2003.
Stent Based Delivery of Sirolimus Reduces Neointimal Formation in a Porcine Coronary Model, Takeshi Suzuki, American Heart Association, Inc. (c) 2001.
Why Tie a Knot When You Can Use Y-Knot?, Innovasive Devices Inc., (c) 1998.
Ask Oxford, compact Oxford English dictionary: projection, Mar. 30, 2009.
Ask Oxford, compact Oxford English dictionary: slit, Mar. 30, 2009.
Textured Surface Technology, Branson Technology, Branson Ultrasonics Corp., (c) 1992.
Arthrex, Protect your graft, Am J Sports Med, vol. 22, No. 4, Jul.-Aug. 1994.
Barrett et al, T-Fix endoscopic meniscal repair: technique and approach to different types of tears, Apr. 95, Arthroscopy vol. 11 No. 2 pp. 245-51.
Cope, Suture Anchor for Visceral Drainage, AJR, vol. 148 pp. 160-162, Jan. 1986.
Gabriel, Arthroscopic Fixation Devices, Wiley Enc. of Biomed Eng., 2006.
Innovasive, We've got you covered, Am J Sports Med, vol. 26, No. 1, Jan.-Feb. 1998.
510k—TranSet Fracture Fixation System, Feb. 24, 2004.
510k—Linvatec Biomaterials modification of Duet and impact Suture Anchor, Nov. 19, 2004.
510k, arthrex pushlock, Jun. 29, 2005.
510k, mitek micro anchor, Nov. 6, 1996.
510k, Multitak Suture System, Jan. 10, 1997.

(56) References Cited

OTHER PUBLICATIONS

510k, Modified Mitek 3.5mm Absorbable Suture Anchor System, Jun. 9, 1997.
510K, Summary for Arthrex Inc.'s Bio-Interference Screw, Jul. 9, 1997.
510k, Surgicraft Bone Tie, Sep. 25, 1998.
Karlsson et al, Repair of Bankart lesions with a suture anchor in recurrent dislocation of the shoulder, Scand. j. Of Med & Science in Sports, 1995, 5:170-174.
Madjar et al, Minimally Invasive Pervaginam Procedures, for the Treatment of Female Stress Incontinence . . ., Artificial Organs, 22 (10) 879-885, 1998.
Nowak et al, Comparative Study of Fixation Techniques in the Open Bankart Operation Using Either A Cannulated Screw or Suture-Anchors, Acta Orthopcedica Belgica, vol. 64—2—1998.
Packer et al, Repair of Acute Scapho-Lunate Dissociation Facilitated by the "Tag"* Suture Anchor, Journal of Hand Surgery (British and European Volume, 1994) 19B: 5: 563-564.
Richmond, Modification of the Bankart reconstruction with a suture anchor, Am J Sports Med, vol. 19, No. 4, pp. 343-346, 1991.
Shea et al, Technical Note: Arthroscopic Rotator Cuff Repair Using a Transhumeral Approach to Fixation, Arthroscopy: The Journal of Arthroscopic and Related Surgery, vol. 14, No. 1 (Jan.-Feb.),1998: pp. 118-122.
Tfix, Acufexjust tied the knot .. ., Am. J. Sports Med., vol. 22, No. 3, May-Jun. 1994.
Wong et al, Case Report: Proper Insertion Angle Is Essential to Prevent Intra-Articular Protrusion of a Knotless Suture Anchor in Shoulder Rotator Cuff Repair, Arthroscopy: The Journal of Arthroscopic and Related Surgery, vol. 26, No. 2 (Feb.), 2010: pp. 286-290.
Cobb et al, Late Correction of Malunited Intercondylar Humeral Fractures Intra-Articular Osteotomy and Tricortical Bone Grafting, J BoneJointSurg [Br] 1994; 76-B:622-6.
Fellinger. et al, Radial avulsion of the triangular fibrocartilage complex in acute wrist trauma: a new technique for arthroscopic repair, Jun.-97, Arthroscopy vol. 13 No. 3 p. 370-4.
Hecker et al , Pull-out strength of suture anchors for rotator cuff and Bankart lesion repairs, Nov.-Dec. 1993, The American Journal of Sports Medicine, vol. 21 No. 6 p. 874-9.
Hernigou et al, Proximal Tibial Osteotomy for Osteoarthritis with Varus Deformity a Ten to Thirteen-Year Follow-Up Study, J Bone Joint Surg, vol. 69-A, No. 3. Mar. 1987, pp. 332-354.
Ibarra et al, Glenoid Replacement in Total Shoulder Arthroplasty, The Orthopedic Clinics of North America: Total Shoulder Arthroplasty, vol. 29 No. 3, Jul. 1998 pp. 403-413.
Mosca et al, Calcaneal Lengthening for Valgus Deformity of the Hindfoot: Results in Children Who Had Severe, Symptomatic Flatfoot and Skewfoot, J Bone Joint Surg,, 1195- pp. 499-512, 1995.
Murphy al, Radial Opening Wedge Osteotomy in Madelung's Deformity, J. Hand Surg, vol. 21 A No. 6 Nov. 1996, p. 1035-44.
Biomet, Stanmore Modular Hip, J. Bone Joint Surg., vol. 76-B : No. Two, Mar. 1994.
Petition for Inter Partes Review of U.S. Pat. No. 5,980,559, IPR 2013-00603, Filing Date Sep. 24, 2013.
Declaration of David Kaplan. Ph.D. Regarding U.S. Pat. No. 5.980,559, IPR 2013-00603, Sep. 24, 2013.
Petition for Inter Partes Review of U.S. Pat. No. 7,087,073, IPR 2013-00604, Filing Date Sep. 24, 2013.
Declaration of Wayne J. Sebastianelli, MD Regarding U.S. Pat. No. 7,087,073, Sept 24, 2013, IPR 2013-00604.
Declaration of Dr. Philip Hardy in Support of Petition for Inter Partes Review of U.S. Pat. No. 6,500, 195, IPR 2013-00624, Sep. 25, 2013.
Declaration of Dr. Philip Hardy in Support of Petition for Inter Partes Review of U.S. Pat. No. 6,500,195, IPR 2013-00624, Sep. 25, 2013.
Petition for Inter Partes Review of U.S. Pat. No. 5,527,343, IPR 2013-00628, Filing Date Sep. 26, 2013, Sep. 25, 2013.
Declaration of Dr. Philip Hardy in Support of Petition for Inter Partes Review of U.S. Pat. No. 5,527,343, IPR 2013-00628, Sep. 25, 2013.
Corrected Petition for Inter Partes Review of U.S. Pat. No. 5,921,986, IPR 2013-00631, Filing Date Sep. 27, 2013.
Expert Declaration of Steve E. Jordan, MD, for Inter Partes Review of U.S. Pat. No. 5,921,986, IPR 2013-00631, Sep. 24, 2013.
Corrected Petition for Inter Partes Review of U.S. Pat. No. 8,147,514, IPR 2013-00632, Filing Date Sep. 27, 2013.
Declaration of Steve Jordan for USP 8, 147,514, from IPR 2013-00632, dated Sep. 23, 2013 (exhibit 1009).
Corrected Petition for Inter Partes Review of U.S. Pat. No. 8,147,514, IPR 2013-00633, Filing Date Sep. 27, 2013.
Declaration of Steve Jordan for USP 8,147,514, from IPR 2013-00633, dated Sep. 23, 2013 (exhibit 1006).
Flory, Principles of Polymer Chemistry, 1953, selected pages (cited in IPR 2013-00603, exhibit 1012).
Grizzi, Hydrolytic degradation of devices based on poly(DL-lactic acid) size-dependence, Biomaterials, 1995, vol. 16, No. 4, p. 305-11 (cited in IPR 2013-00603, exhibit 1006).
Gopferich, Mechanisms of polymer degradation and erosion, Biomaterials, 1996, vol. 17, No. 2, pp. 103-114 (cited in IPR 2013-00603, exhibit 1013).
Gao et el, Swelling of Hydroxypropyl Methylcellulose Matrix Tablets . . . , J. Of Pharmaceutical Sciences, vol. 85, No. 7, Jul. 1996, pp. 732-740 (cited in IPR 2013-00603, exhibit 1014).
Linvatec, Impact Suture Anchor brochure, 2004 (cited in IPR 2013-00628, exhibit 1010).
Seitz et al, Repair of the Tibiofibular Syndesmosis with a Flexible Implant, J. Of Orthopaedic Trauma, vol. 5, No. 1, pp. 78-82, 1991 (cited in IPR 2013-00631, exhibit 1007) (cited in 2013-00632).
Translation of FR2696338 with translators certificate dated Sep. 17, 2013 (cited in IPR 2013-00631, 2013-00632).

* cited by examiner

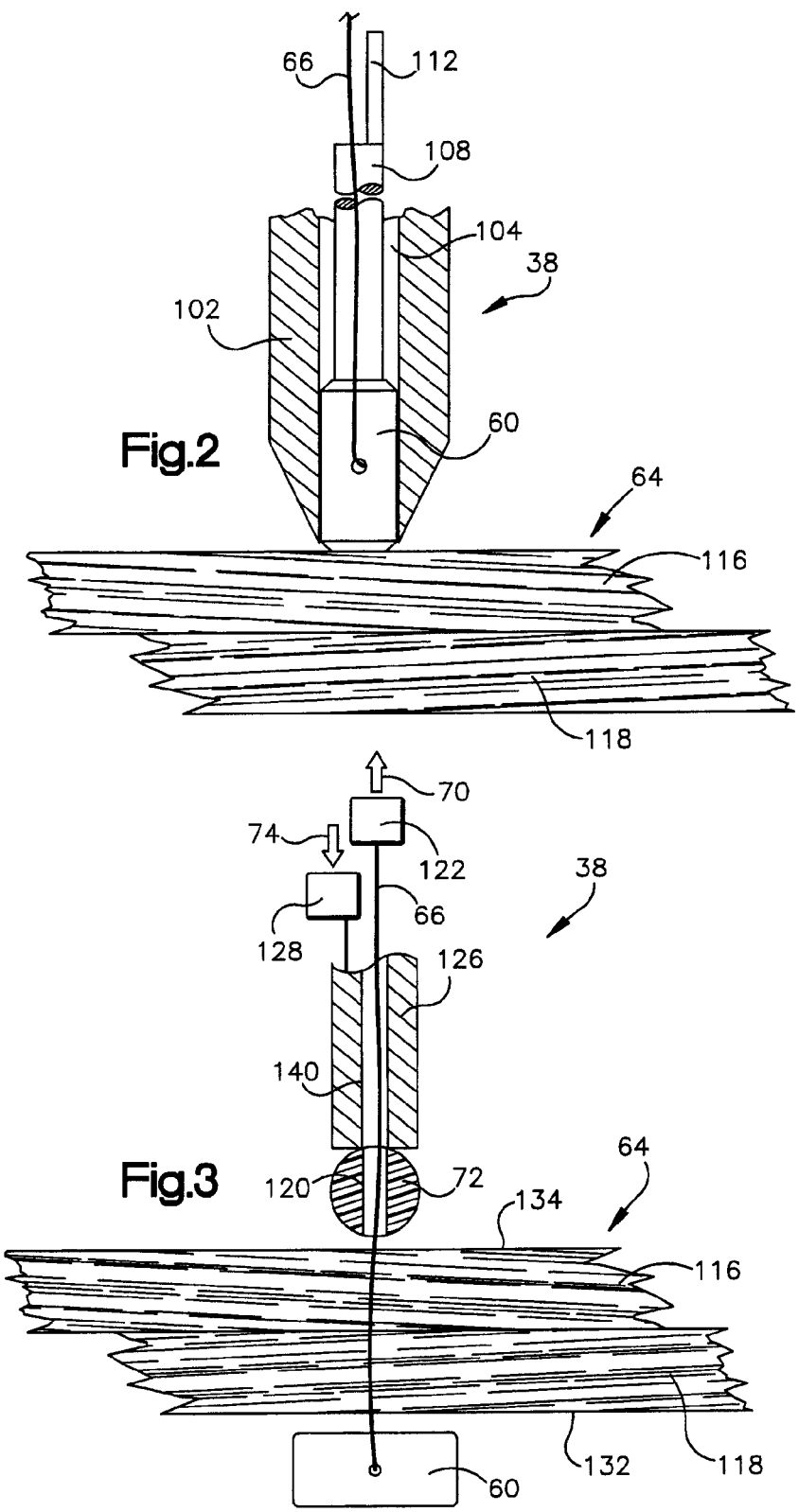

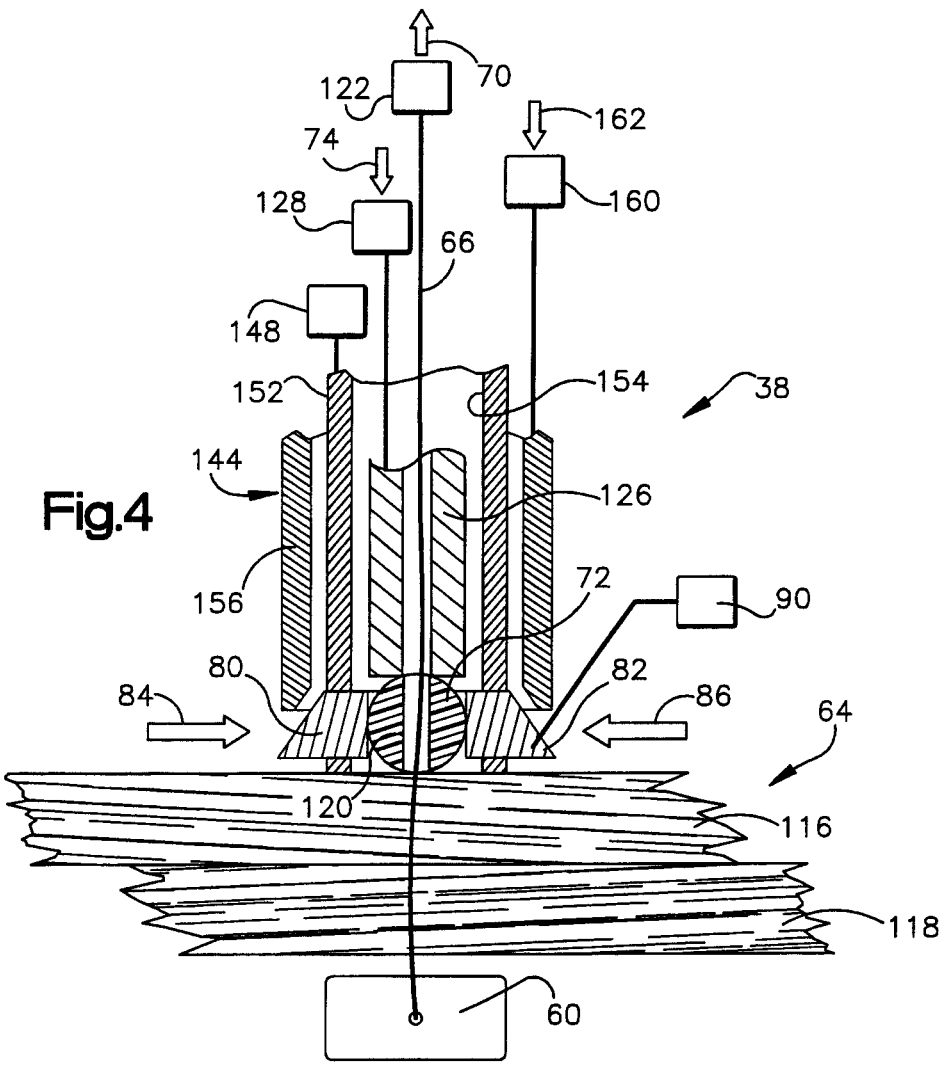

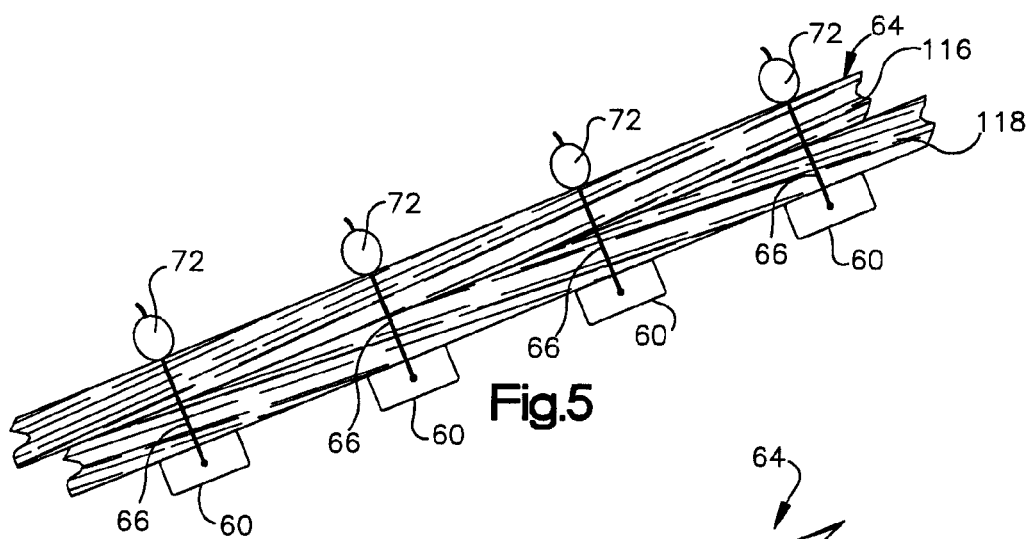
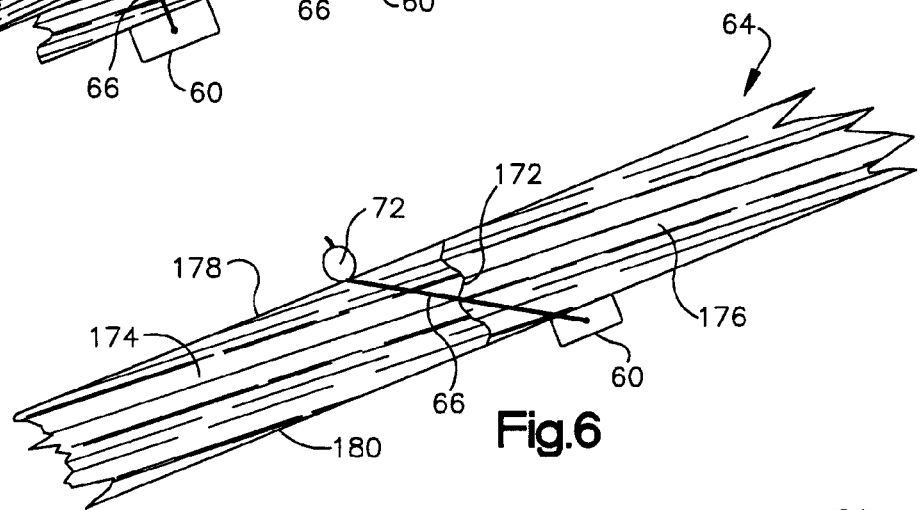
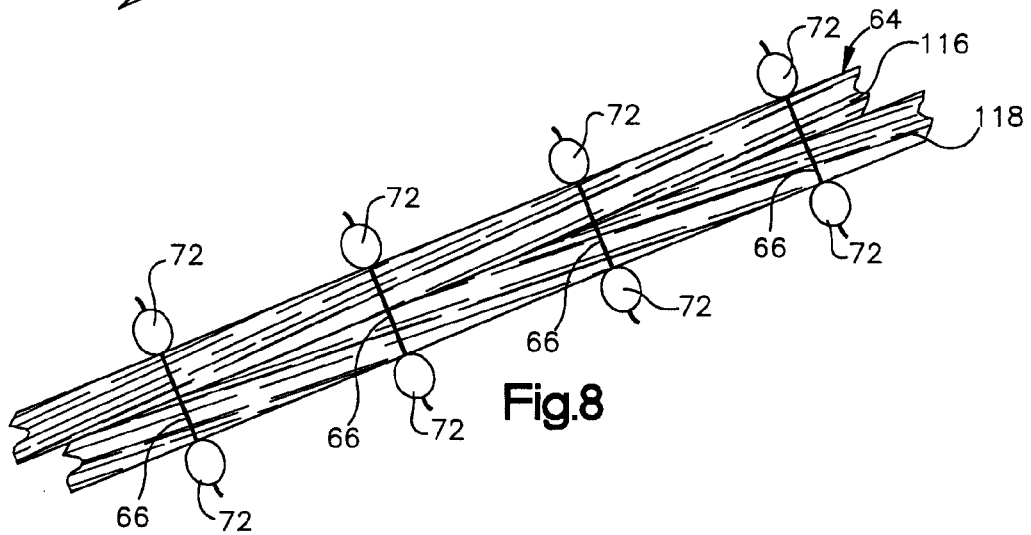

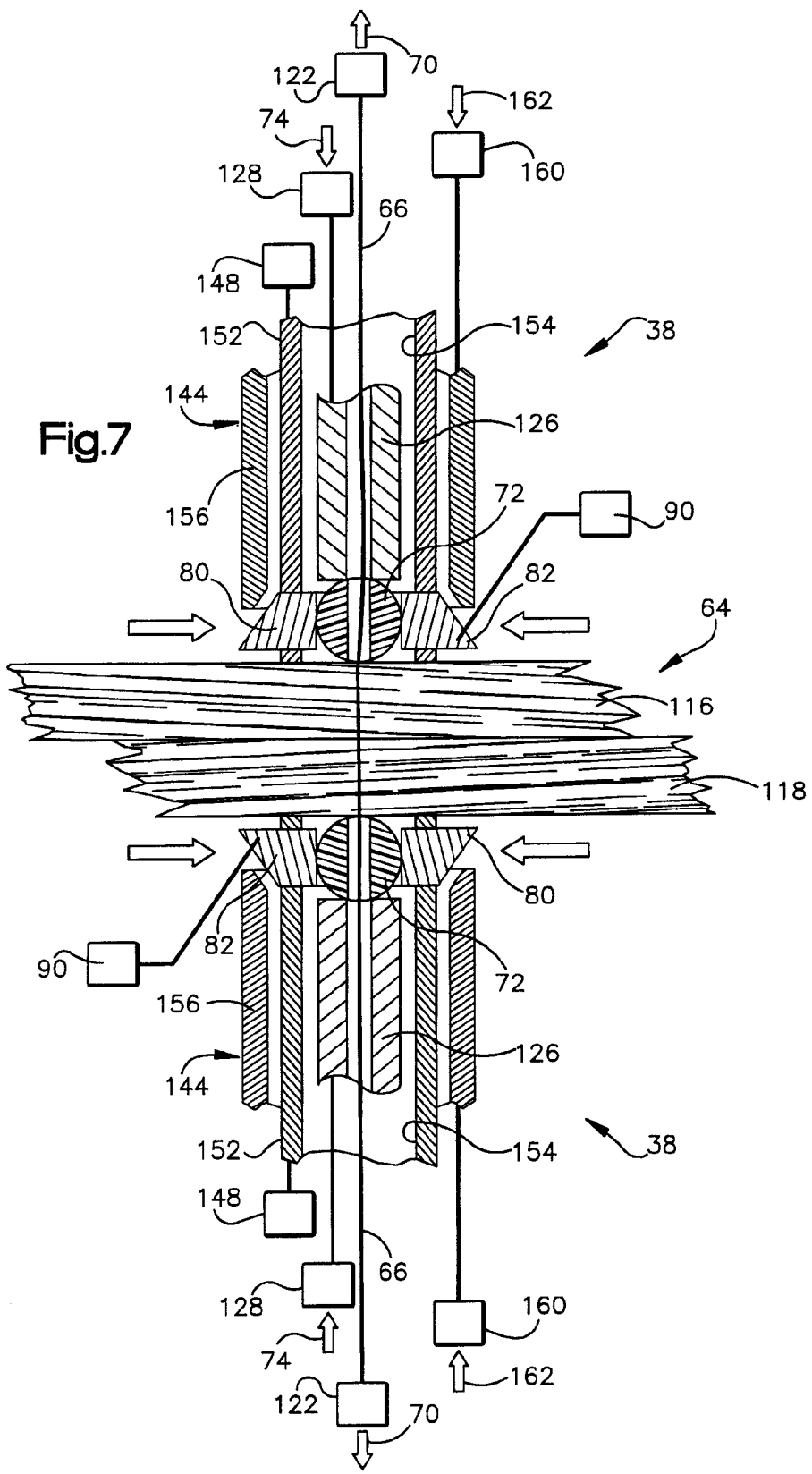

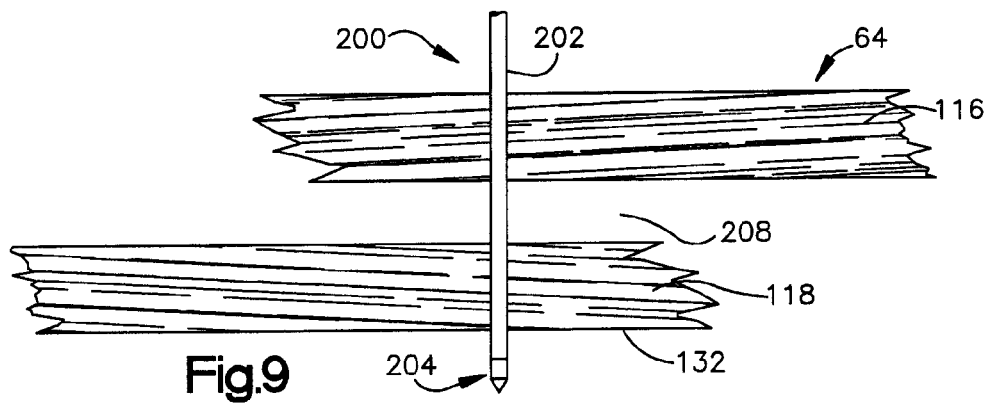
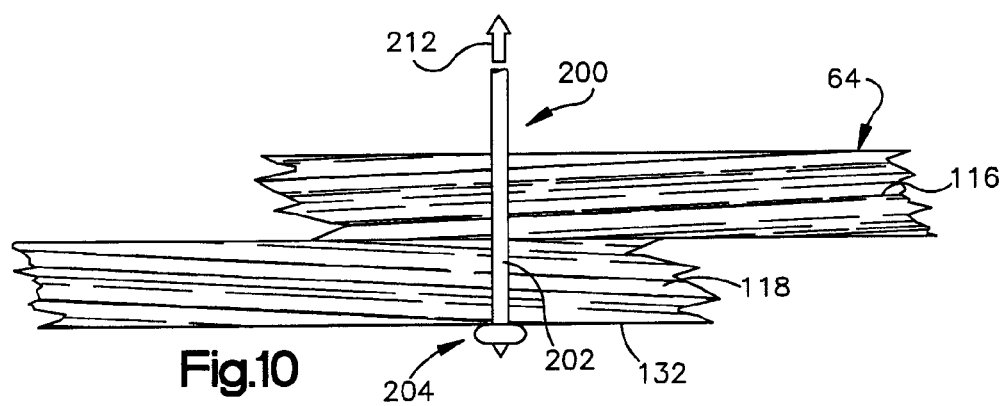
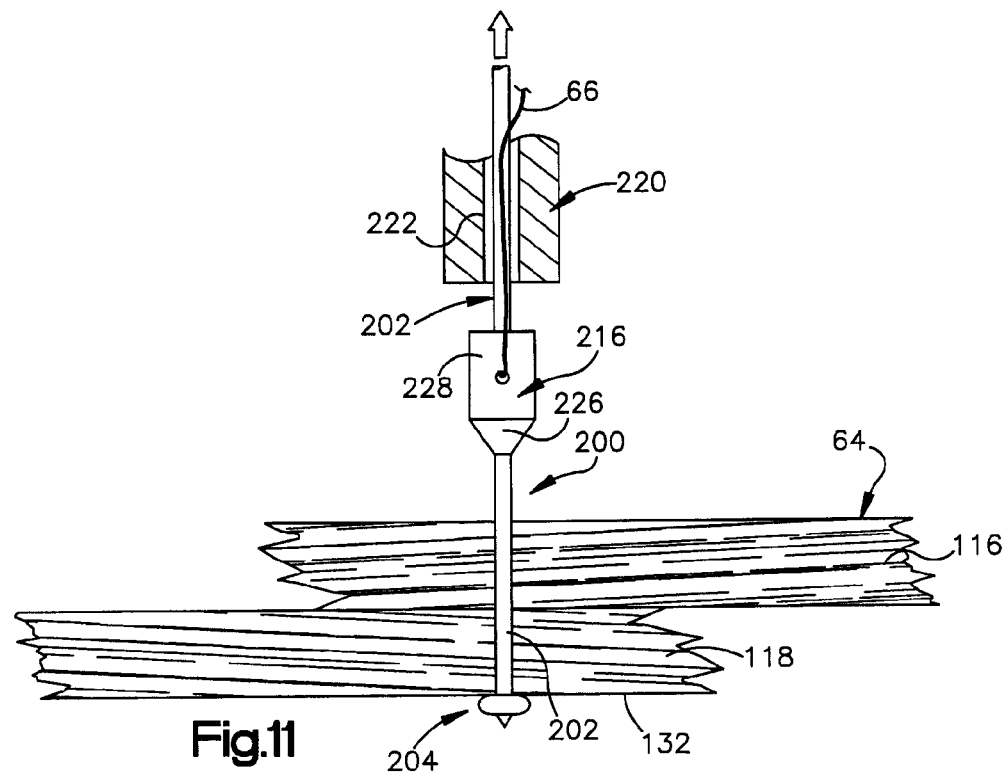

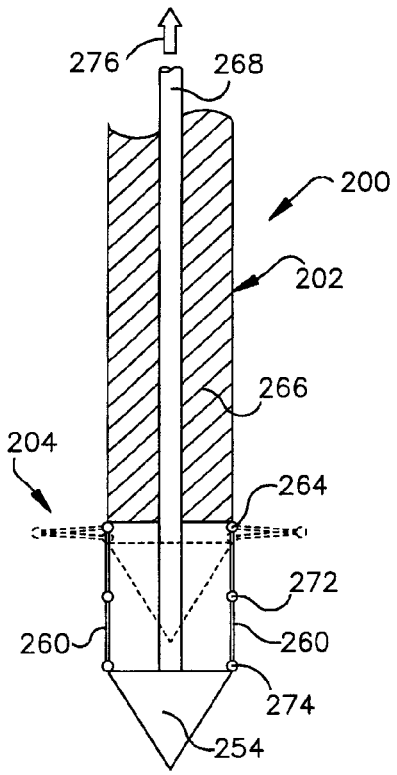
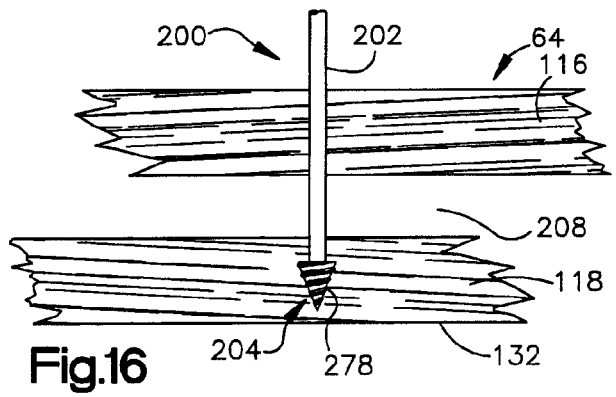
Fig.16
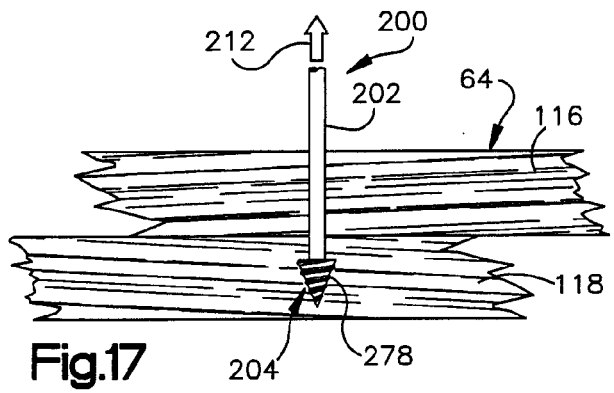
Fig.17
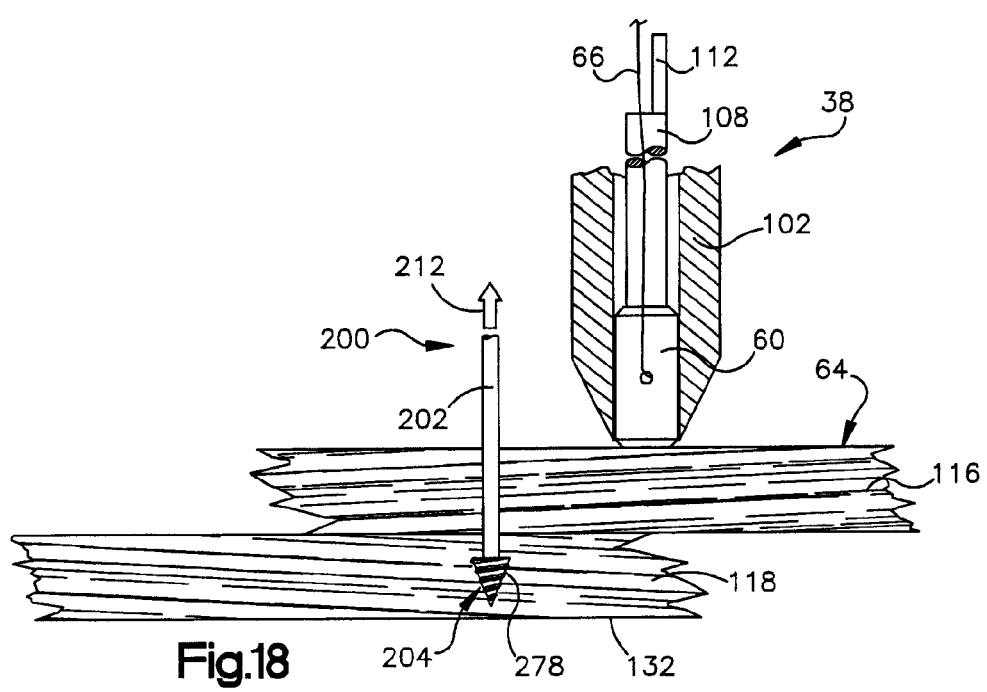
Fig.15
Fig.18

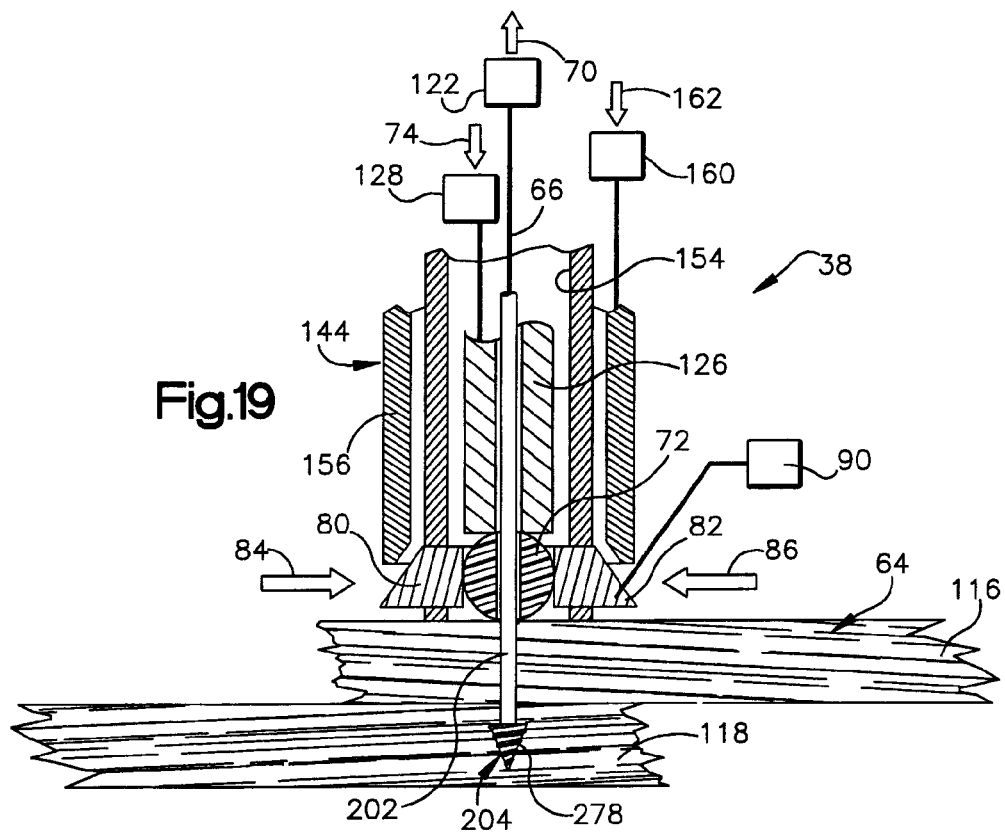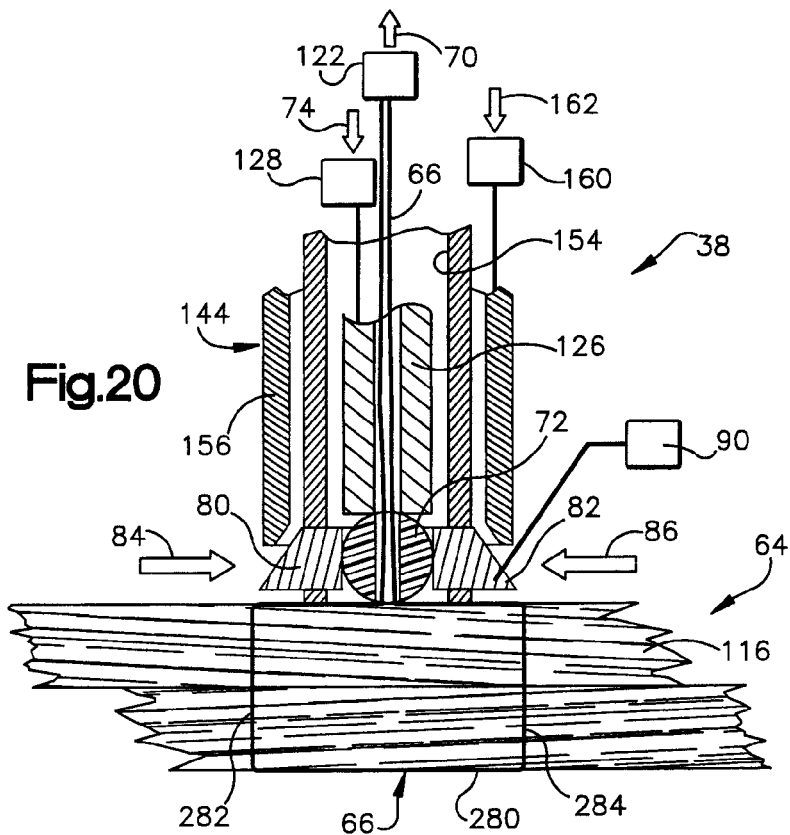

ROBOTIC FASTENING SYSTEM

CROSS REFERENCE TO RELATED APPLICATIONS

This application is a continuation of U.S. patent application Ser. No. 10/102,413 filed Mar. 20, 2002, which is hereby incorporated by reference in its entirety.

BACKGROUND

The present invention relates to the securing of body tissue.

Body tissue has previously been secured utilizing sutures, staples, pegs, screws, and/or other fasteners. When one or more of these known devices is to be utilized to secure body tissue, the device may be concealed from view within a patient's body. Of course, this makes the securing of the body tissue more difficult. The manner in which a suture may be utilized to secure body tissue is disclosed in U.S. Pat. No. 6,159,234. The manner in which a staple may be utilized in association with body tissue is disclosed in U.S. Pat. No. 5,289,963. It has previously been suggested that a robotic mechanism may be utilized to assist in the performance of surgery. Various known robotic mechanisms are disclosed in U.S. Pat. Nos. 5,078,140; 5,572,999; 5,791,231; 6,063,095; 6,231,565; and 6,325,808.

SUMMARY

The present invention relates to a method of securing either hard or soft body tissue. A robotic mechanism or manual effort may be used to position a fastener relative to the body tissue. The fastener may be a suture, staple, screw, or other known device.

The fastener may be a suture which is tensioned with a predetermined force by a robotic mechanism or manual effort. The robotic mechanism or manual effort may also be used to urge a retainer toward body tissue with a predetermined force. The suture may be gripped with the retainer while the suture is tensioned with a predetermined force and while the retainer is urged toward the body tissue with a predetermined force.

Alternatively, the fastener may be a staple. A robotic mechanism or manual effort may be utilized to position the staple relative to body tissue. The robotic mechanism or manual effort may effect a bending of the staple to move legs of the staple into engagement with each other. The legs of the staple may be bonded together at a location where the legs of the staple are disposed in engagement.

Regardless of what type of fastener is utilized, a positioning apparatus may be used to position the body tissue before and/or during securing with a fastener. The positioning apparatus may include a long thin member which transmits force to the body tissue. Force may be transmitted from an expanded end portion of the long thin member to the body tissue. A second member may cooperate with the long thin member to grip the body tissue. The long thin member may be positioned relative to the body tissue by a robotic mechanism or manual effort.

Various imaging devices may be utilized to assist in positioning a fastener, such as a rivet suture or staple, relative to body tissue. Under certain circumstances at least, it may be desirable to utilize two or more different types of imaging devices. Thus, an endoscope and a magnetic resonance imaging apparatus (MRI) may be utilized to provide an image. Alternatively, an endoscope and a fluoroscopic device may be utilized. If desired, ultrasonic imaging devices may be utilized in association with another imaging device, such as an endoscope or magnetic resonance imaging device. One or more markers may be provided on fasteners to facilitate location of the fasteners in an image.

A fastener may be utilized to secure a scaffold containing viable tissue components in place on body tissue. The tissue components may be stem cells, fetal cells, mesenchymal cells, and/or any desired type of precursor cells. It is contemplated that the scaffold with one or more different types of tissue components may be positioned at any desired location within a patient's body, such as within an organ, by the robotic mechanism. For example, the scaffold could be positioned in the pancreas or liver of a patient. Alternatively, the scaffold could be connected with a bone in the patient's body. The scaffold may be positioned relative to the body tissue by the robotic mechanism or manual effort. One or more markers may be provided on the scaffold to facilitate location of the scaffold in an image.

It is contemplated that the robotic mechanism may advantageously be utilized to position surgical implants other than fasteners in a patient's body. For example, the robotic mechanism may be utilized to position a prosthesis in a patient's body. If desired, the robotic mechanism may be utilized to position a screw type fastener at a specific location in a patient's body. The robotic mechanism may be used to position a scaffold containing viable tissue components relative to body tissue.

BRIEF DESCRIPTION OF THE DRAWINGS

The foregoing and other features of the invention will become more apparent upon a consideration of the following description taken in connection with the accompanying drawings wherein:

FIG. 2 is a schematic illustration depicting the manner in which the robotic mechanism of FIG. 1 is utilized to move a suture anchor into a patient's body;

FIG. 3 is a schematic illustration depicting the manner in which the robotic mechanism of FIG. 1 is utilized to tension a suture with a predetermined force and urge a suture retainer toward body tissue with a predetermined force;

FIG. 4 is a schematic illustration depicting the manner in which the robotic mechanism of FIG. 1 is utilized to grip the suture with a suture retainer while the suture is tensioned with a predetermined force and the retainer is urged toward body tissue with a predetermined force;

FIG. 5 is a schematic illustration depicting the linear apposition of body tissue with sutures, anchors and retainers which were positioned by the robotic mechanism of FIG. 1 in the same manner as illustrated in FIGS. 2-4;

FIG. 6 is a schematic illustration depicting an alternative manner in which body tissue may be secured by the robotic mechanism of FIG. 1 using an anchor, suture and retainer;

FIG. 7 (on sheet 5 of the drawings) is a schematic illustration, similar to FIG. 4, illustrating the manner in which a pair of suture retainers are connected with a suture by the robotic mechanism of FIG. 1 to secure body tissue;

FIG. 8 is a schematic illustration, similar to FIG. 5, illustrating the linear apposition of body tissue with a fastener which includes a suture and plurality of suture retainers which are positioned by the robotic mechanism of FIG. 1 in the manner illustrated in FIG. 7;

FIG. 9 is a schematic illustration depicting the manner in which a long thin member of a tissue positioning assembly is moved into body tissue by the robotic mechanism of FIG. 1;

FIG. 10 is a schematic illustration of a manner in which a leading end portion of the long thin member of FIG. 9 is expanded by the robotic mechanism of FIG. 1 and transmits force from the robotic mechanism to body tissue;

FIG. 11 is a schematic illustration depicting the manner in which an anchor is moved along the long thin member of FIG. 10 into body tissue by the robotic mechanism of FIG. 1;

FIG. 15 is an enlarged, fragmentary sectional view depicting another manner in which the leading end portion of the long thin member of FIG. 9 may be expanded by the robotic mechanism of FIG. 1;

FIG. 16 is a schematic illustration depicting the manner in which a long thin member of an alternative embodiment of the tissue positioning assembly is moved into body tissue by the robotic mechanism of FIG. 1;

FIG. 17 is a schematic illustration depicting how a space between upper and lower body tissues of FIG. 16 is closed by movement of the tissue positioning assembly by the robotic mechanism of FIG. 1;

FIG. 18 is a schematic illustration depicting the manner in which a fastener is moved into the body tissue of FIG. 16 by the robotic mechanism of FIG. 1 while the body tissue is positioned in the manner illustrated in FIG. 17;

FIG. 19 is a schematic illustration depicting the manner in which a retainer may be connected with the long thin member of the tissue positioning assembly of FIGS. 16 and 17 by the robotic mechanism of FIG. 1 utilizing the apparatus of FIGS. 4 and 7;

FIG. 20 is a schematic illustration depicting an alternative manner of utilizing the robotic mechanism of FIG. 1 to secure body tissue with a suture and retainer;

FIG. 27 or FIG. 28 are connected with body tissue by staples in the manner illustrated in FIGS. 24-26 by operation of the robotic mechanism of FIG. 1;

DETAILED DESCRIPTION

Robotic Securing of Tissue

Figure 1:
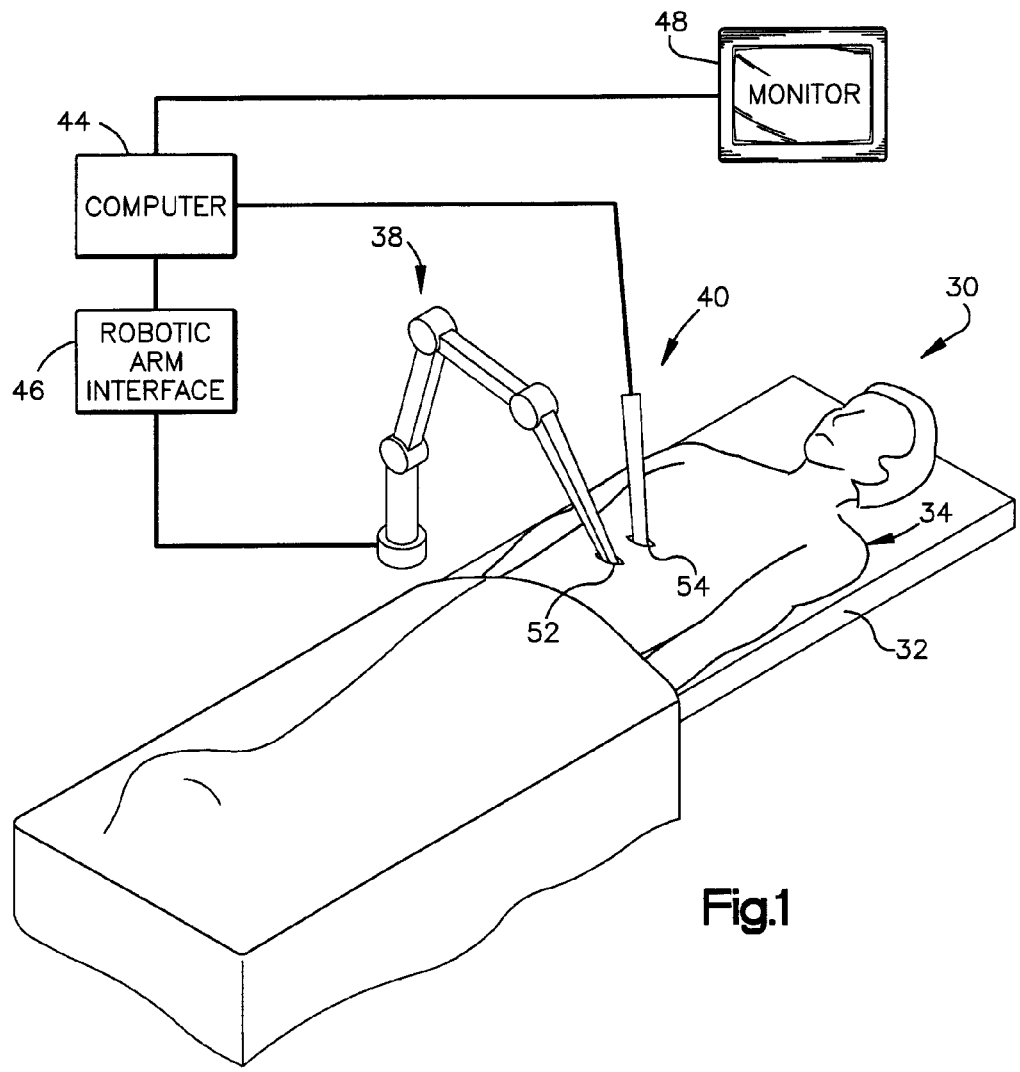
FIG. 1 is a schematic illustration depicting the manner in which a robotic mechanism and an imaging device are positioned relative to a patient's body.

An apparatus 30 for use in securing tissue in a patient's body is illustrated schematically in FIG. 1. Although the apparatus 30 will be described herein as being used to secure tissue, it is contemplated that the apparatus 30 may be used for other surgical procedures if desired.

The apparatus 30 includes an operating table 32 which is disposed in a sterile operating room environment. A patient 34 may be covered by a known sterile drapery system. Alternatively, the patient 34 may be covered by a drapery system which is connected with a surgeon so as to maintain a sterile field between the surgeon and the patient in the manner disclosed in U.S. patent application Ser. No. 09/941,185 Filed Aug. 28, 2001 by Peter M. Bonutti. Of course, any desired sterile drapery system may be provided to cover the patient 34.

A robotic mechanism 38 is provided to position a tissue securing device, fastener, or other apparatus at a desired location within the patient during performance of a surgical procedure. An imaging device 40 is operable to provide an image of a location where the robotic mechanism 38 is securing the body tissue with a fastener or performing other steps in a surgical procedure. A programmable computer 44 is connected with the robotic mechanism 38 through a robotic arm interface 46. In addition, the computer 44 is connected with the imaging device 40 and a monitor or display 48. The monitor or display 48 is visible to a surgeon operating the apparatus 30 and provides an image of the location where the robotic mechanism 38 is being utilized in the performance of a surgical procedure on the patient 34.

The robotic mechanism 38 is guided by automatic controls which include the computer 44 and robotic arm interface 46. The robotic mechanism 38 may have a construction which is different than the illustrated construction and may include one or more adaptive arms. The robotic mechanism 38 is a reprogrammable, multifunctional manipulator designed to move through various programmed motions for the performance of a surgical procedure. The robotic mechanism 38 may have manually operable controls which provide for interaction between the surgeon and the robotic mechanism. The robotic mechanism 38 is utilized in the securing of a patient's body tissue. However, it is contemplated that the robotic mechanism 38 will be utilized during the performance of other surgical steps in addition to the securing of body tissue.

The robotic mechanism 38 may have many different constructions, including constructions similar to those disclosed in U.S. Pat. Nos. 5,078,140; 5,572,999; 5,791,231; 6,063,095; 6,231,565; and/or U.S. Pat. No. 6,325,808. The specific robotic mechanism 38 illustrated in FIG. 1 has a construction and mode of operation generally similar to that disclosed in U.S. Pat. No. 5,876,325. However, it should be understood that the robotic mechanism 38 could have any desired construction. The robotic mechanism 38 may have one or more known adaptive arms.

The use of the robotic mechanism 38 and imaging device 40 enables the size of incisions 52 and 54 in the patient's body to be minimized. Of course, minimizing the size of the incisions 52 and 54 tends to reduce patient discomfort and recovery time. It contemplated that the robotic mechanism 38 and imaging device 40 will be utilized during the performance of many different surgical procedures.

During the performances of these surgical procedures, the robotic mechanism 38 may be utilized to secure body tissue. The robotic mechanism 38 may be used to position a suture anchor 60 (FIG. 2) relative to body tissue 64 in the patient 32 during the performance of any one of many known surgical procedures. The body tissue 64 may be hard and/or soft body tissue.

Once the anchor 60 has been positioned relative to the body tissue 64, the robotic mechanism 38 is operated to tension a suture 66 connected with the anchor 60 with a predetermined force, in the manner indicated schematically by an arrow 70 in FIG. 3. At the same time, the robotic mechanism 38 of FIG. 1 presses a suture retainer 72 against the body tissue 64 with a predetermined force, indicated schematically by an arrow 74 in FIG. 3. The force 74 may be equal to, greater than, or less than the force 70 with which the suture 66 is tensioned.

The anchor 60, suture 66, and suture retainer 72 may be formed of any desired material. The illustrated anchor 60, suture 66 and suture retainer 77 are all formed of a polymeric material. The anchor 60, suture 66, and suture retainer 72 may all be formed of a biodegradable polymeric material. However, the anchor 60, suture 66, and/or suture retainer 72 could be formed of metal or other known materials if desired.

The suture 55 is a monofilament. However, the suture 66 could be formed by a plurality of filaments and could have a braided construction. The suture 66 could have a construction similar to the construction of a rope or cable if desired.

While the suture 66 is tensioned with the predetermined force 70 and while the suture retainer 72 is pressed against the body tissue 64 with a force 74, the robotic mechanism 38 plastically deforms the polymeric material of the suture retainer 72 in the manner illustrated schematically in FIG. 4. The plastic deformation of the suture retainer 72 by the robotic mechanism 38 may take place at a temperature which is either below or in the transition temperature range for the polymeric material of the suture retainer 72. Thus, the suture retainer 72 may be plastically deformed by cold flowing material of the suture retainer.

Alternatively, the suture retainer 72 may be deformed by transmitting force from the robotic mechanism 38 to the retainer after the polymeric material of the retainer has been heated into a transition temperature range of the material of the suture retainer. When the material of the suture retainer 72 has been heated into its transition temperature range, the material can be readily plastically deformed with a viscous flow or movement of the material. It is believed that it may be preferred to maintain the material of the suture 66 at a temperature which is below the transition temperature range for the material of the suture. The suture retainer 72 may be formed of the materials disclosed in U.S. Pat. No. 6,203,565 and heated in the manner disclosed in the patent.

It is contemplated that the anchor 60, suture 66, and suture retainer 72 may all be formed of biodegradable polymeric materials. However, it is believed that it may be desired to form the suture retainer 72 of a biodegradable material having a lower transition temperature range than the transition temperature range for the material of the suture 66. This would facilitate operation of the robotic mechanism 38 to heat the suture retainer 72 into its transition temperature range without heating the material of the suture 66 into the transition temperature of the material of the suture. This would minimize damage to or deformation of the suture 66 when the suture retainer 72 is deformed by operation of the robotic mechanism 38. Of course, the anchor 60, suture 66 and suture retainer 72 could all be formed of the same biodegradable material if desired.

It is contemplated that, in some circumstances at least, it may be desired to heat both the polymeric material of the suture 66 and the polymeric material of the retainer 72 into their transition temperature ranges. If this is done, the material of the suture 66 and the retainer 72 could be fused together. This would result in a blending of the material of the suture 66 and suture retainer 72 in the area where they are disposed in engagement.

During operation of the robotic mechanism 38, the suture retainer 72 is bonded to the suture 66 without significant deformation of the suture. When the polymeric material of the suture retainer 72 is heated into its transition temperature range, the material of the suture retainer softens and loses some of its rigidity. By applying force against the heated material of the suture retainer 72, the robotic mechanism 38 can be operated to cause the material of the suture retainer to plastically deform and flow around and into engagement with the suture 66.

When the material of the suture retainer 72 cools, a secure bond is formed between the material of the suture retainer and the suture 66. This bond may be formed in the manner disclosed in the aforementioned U.S. Pat. No. 6,203,565. However, it is contemplated that the material of the suture retainer 72 could be plastically deformed and bonded without heating, in the manner disclosed in U.S. Pat. No. 6,010,525.

It is contemplated that the suture retainer 72 may be plastically deformed by operating the robotic mechanism 38 to press the force transmitting members 80 and 82 against opposite sides of the suture retainer 72 in the manner indicated by arrows 84 and 86 in FIG. 4. The force transmitting members 80 and 82 may be pressed against opposite sides of the suture retainer 72 with sufficient force to plastically deform the material of the suture retainer. The resulting cold flowing of the material in the suture retainer 72 would result in the suture retainer bonding to the suture 66.

It is contemplated that the suture retainer 72 may be heated by the robotic mechanism into the transition temperature range of the material of the suture retainer in many different ways. For example, the suture retainer 72 may be heated into its transition temperature range by the application of ultrasonic vibratory energy to the suture retainer. If this is to be done, the force transmitting member 80 functions as an anvil and the force transmitting member 82 functions as a horn. To enable the force transmitting member 82 to function as a horn, the force transmitting member is connected with a source 90 of ultrasonic vibratory energy by the robotic mechanism 58. One commercially available source of ultrasonic vibratory energy is provided by Dukane Corporation Ultrasonics Division, 2900 Dukane Drive, St. Charles, Ill. Of course, there are other sources of apparatus which can be utilized to provide ultrasonic vibratory energy.

When the ultrasonic vibratory energy is to be applied to the suture retainer 72 by the robotic mechanism, the force transmitting member or horn 82 is vibrated at a rate in excess of 20 kilohertz. Although the horn or force transmitting member 82 may be vibrated at any desired frequency within a range of 20 kilohertz to 70 kilohertz, it is believed that it may be desirable to vibrate the force transmitting member or horn 82 at a rate which is close to or greater than 70 kilohertz. The force transmitting member or horn 82 is vibrated for a dwell time which is sufficient to transmit enough ultrasonic vibratory energy to the suture retainer 72 to heat at least a portion of the material of the suture retainer into its transition temperature range.

The frictional heat created by the ultrasonic vibratory energy transmitted to the suture retainer 72 is sufficient to heat the material of the suture retainer at locations adjacent to the suture 66, into the transition temperature range of the material of the suture retainer. As this occurs, the softened material of the suture retainer 72 is plastically deformed by force applied against the suture retainer by the anvil or force transmitting member 80 and the horn or force transmitting member 82. After interruption of the transmission of ultrasonic vibratory energy to the suture retainer 72, the material of the suture retainer cools and bonds to the suture 66.

The general manner in which ultrasonic vibratory energy is applied to the suture retainer 72 and in which the suture retainer is plastically deformed to grip the suture 66 is the same as disclosed in U.S. patent application Ser. No. 09/524, 397 Filed Mar. 13, 2000 by Peter M. Bonutti, et al. and entitled Method of Using Ultrasonic Vibration to Secure Body Tissue. However, it is contemplated that the material of the suture retainer 72 could be heated in ways other than the application of ultrasonic vibratory energy. For example, the suture retainer 72 could be heated by an electrical resistance heater element or by a laser.

It is contemplated that the robotic mechanism 38 may be operated to secure the body tissue 64 in many different ways utilizing the anchor 60, suture 66, and suture retainer 72. One way in which the body tissue 64 may be secured is by linear apposition in the manner illustrated schematically in FIG. 5. A plurality of sutures 66 have a linear configuration and extend between anchors 60 disposed on one side of the body tissue 64 and retainers 72 disposed on the opposite side of the body tissue.

The sutures 66 are connected with openings which extend diametrically across the cylindrical anchors 60. However, it is contemplated that the sutures 66 could be connected with the anchors 60 in a different manner by operation of the robotic mechanism 38. For example, it is contemplated that the sutures 66 could be connected with the anchors 60 in any one of the ways disclosed in U.S. Pat. No. 5,534,012; 5,713,921; 5,718,717; or 5,845,645. It is also contemplated that the anchors could have the same construction and/or be formed of materials disclosed in any one of the aforementioned U.S. Patents.

In the embodiment illustrated in FIG. 5, the body tissue 64 is formed by a pair of layers 116 and 118 of soft tissue which are held in flat abutting engagement by forces transmitted between the suture anchors 60 and retainers 72 through the sutures 66. However, the suture anchors 60, sutures 66, and retainers 72 could be utilized to secure many different types of body tissue. For example, the anchors 60 could be disposed in a bone and the sutures 66 and retainers 72 utilized to secure soft tissue, such as a tendon or ligament with the bone. The suture anchors 60, sutures 66 and retainers 72 may be utilized for rotator cuff repairs or meniscus repairs.

The suture anchor 60, suture 66 and retainer 72 form a fastener assembly which is used by surgeon controlling operation of the robotic mechanism 38 to secure body tissues together or with surgical implants. The robotic mechanism 38 may be used with many different types of fastener assemblies during performance of surgical procedures at many different locations in a patient's body. The fastener assembly positioned by the robotic mechanism 38 may be a bonded rivet of the type disclosed in the aforementioned U.S. Pat. No. 6,203, 565. However, it should be understood that the fastener assembly may have any desired construction.

The fastener assembly utilized with the robotic mechanism 38 may be used to secure soft body tissues to each other and/or to secure soft body tissues with hard body tissues. The fastener assembly utilized with the robotic mechanism 38 may be used to secure hard body tissues together. The robotic mechanism 38 may be used to secure a surgical implant, such as a prosthesis, with hard and/or soft body tissue.

Anchor, Suture and Retainer Assembly

In the embodiment invention illustrated in FIGS. 1-5, the body tissue 64 is secured with a fastener assembly formed by the anchor 60, suture 66 and retainer 72. The fastener assembly is positioned relative to body tissue 64 by the robotic mechanism 38, that may include one or more adaptive arms having a known construction.

The use of the robotic mechanism 38 to position the anchor 60, suture 66 and retainer 72 enables tension force in the suture 66 and force applied against the body tissue by the anchor 60 and retainer 72 to be accurately controlled. By using the imaging device 40 in association with the robotic mechanism 38, a surgeon can view the monitor 48 and be certain that the anchor 60, suture 66 and retainer 72 are being positioned in the desired manner in the patient's body. This enables the surgeon to minimize the size of the incisions 52 and 54 and still have visual assurance that the surgical procedure is being properly performed in the patient's body by the robotic mechanism. When the robotic mechanism 38 includes adaptive arms, input by the surgeon in response to an image on the monitor 48 is facilitated.

The robotic mechanism 38 includes a cylindrical tubular inserter member 102 (FIG. 2). The inserter member 102 has a cylindrical passage 104 which extends through the inserter member 102. The cylindrical passage 104 has a diameter which is slightly greater than the diameter of the cylindrical anchor 60.

Although the cylindrical anchor 60 has been illustrated in FIG. 2 as having a blunt leading end portion, it is contemplated that the cylindrical anchor 60 could have a pointed leading end portion in the manner disclosed in U.S. Pat. No. 5,718,717. Alternatively, the anchor could be constructed as disclosed in U.S. patent application Ser. No. 09/556,458 filed May 3, 2000 by Peter M. Bonutti and entitled Method and Apparatus for Securing Tissue and have a pointed leading end portion.

The anchor 60 may be formed of a material which absorbs body liquid while the pointed leading end portion of the anchor is formed of a different material that is relatively rigid and capable of piercing the imperforate body tissue 64. When the body of the anchor 60 absorbs body liquid, the anchor expands in all directions and forms an interlock with the body tissue 64 in the manner disclosed in U.S. Pat. No. 5,718,717. Of course the pointed end portion of the anchor could be omitted in the manner also disclosed in the aforementioned U.S. Pat. No. 5,718,717.

When the anchor 60 is to be inserted into the body tissue by the robotic mechanism, a cylindrical pusher member 108 is pressed against the trailing end of the anchor 60. The pusher member 108 is telescopically moved along the passage 104 by a suitable drive assembly in the robotic mechanism 38. When the pusher member 108 has moved the anchor to a desired position relative to the body tissues 64, the robotic mechanism 38 is operated to extend a push rod 112 from the pusher member 108. The push rod 112 applies a force to the anchor 60 at a location offset from a central axis of the anchor. The resulting torque on the anchor 60 causes the anchor to pivot relative to the body tissue 64 and change orientation relative to the body tissue.

The manner in which the pusher member 108 is moved along the passage 104 in the inserter member 102 by the robotic mechanism 38 may be the same as is disclosed in U.S. patent application Ser. No. 09/789,621 filed Feb. 21, 2001 by Peter M. Bonutti and entitled Method of Securing Body Tissue. The manner in which the anchor 60 pivots relative to the body tissue 64 when the push rod 112 is extended from the pusher member 108 may be the same as is disclosed in U.S. Pat. No. 5,814,072. However, the anchor 60 may be pivoted relative to the body tissue 64 in a different manner if desired. For example, the anchor 60 could be pivoted relative to the body tissue 64 in the manner disclosed in U.S. Pat. No. 5,782,862.

In the embodiment invention illustrated in FIG. 2, the body tissue 64 includes an upper or first layer or segment 116 and a lower or second layer or segment 118. The two layers 116 and 118 are soft body tissues through which the anchor 60 is pushed by the pusher member 80. As the anchor 60 emerges from lower layer 118 of the body tissue 64, the push rod 112 is extended to cause the anchor 60 to pivot or toggle relative to the lower layer 118 of body tissue.

In the embodiment invention illustrated in FIG. 2, the anchor 60 is pushed through the two layers 116 and 118 of body tissue. However, it is contemplated that the anchor 60 could be pushed through only the upper layer 116 of body tissue. The anchor would be moved into the lower layer 118 of body tissue and pivoted or toggled by extension of the push rod 112 from the pusher member 108. This would position the anchor in the lower layer 118 of body tissue. It is contemplated that lower portion 118 of the body tissue could be relatively thick, compared to the upper layer 116.

If desired, the anchor 60 may not be moved through the upper layer 116 of body tissue. The anchor 60 may be moved into and/or through only the layer 118 of body tissue. Once this has been done, the suture 66 may be moved through the layer 116 of body tissue.

It is also contemplated that the anchor could be positioned in hard body tissue. For example, the anchor 60 could be positioned in bone in the manner disclosed in U.S. Pat. No. 6,033,430. When the anchor 60 is positioned in bone, the suture 66 may be used to secure a tendon or ligament to the bone in the manner disclosed in U.S. Pat. No. 6,152,949. Regardless of whether the anchor 60 is positioned in hard body tissue or soft body tissue, the anchor may be formed of any one of the materials and/or constructed in any one of the ways disclosed in the aforementioned U.S. Pat. No. 6,152,949.

Once the anchor 60 has been moved to the desired orientation relative to the body tissue (FIG. 3), the retainer 72 is positioned relative to the suture 66 and body tissues. The retainer 72 has a spherical configuration with a diametrically extending central passage 120. However, the retainer 72 may have any desired construction, for example, any one of the constructions disclosed in U.S. Pat. No. 6,159,234. Alternatively, the retainer 72 may have any one of the constructions disclosed in U.S. patent application Ser. No. 09/524,397 filed Mar. 13, 2000 by Peter M. Bonutti et al. and entitled Method of Using Ultrasonic Vibration to Secure Body Tissue.

The suture retainer 72 and suture 66 are both preferably formed of a biodegradable polymer, such as polycaperlactone. Alternatively, the suture 66 and/or suture retainer 72 could be formed of polyethylene oxide terephthalate or polybutylene terephthalate. It is contemplated that other biodegradable or bioerodible copolymers could be utilized if desired. The suture anchor 60 may be formed of the same material as the suture 66 and/or retainer 72. Also, the suture 66 and/or retainer 72 could be formed of an acetyl resin, such as "Delrin" (Trademark). Alternatively, the suture 66 and/or suture retainer 72 could be formed of a pora-dimethylamino-benzenediazo sodium sulfonate, such as "Dexon" (Trademark). The suture 66 may also be a monofilament or formed of a plurality of interconnected filaments.

Although it may be desired to form the anchor 60 of the same material as the suture 66 and/or retainer 72, the anchor could be formed of a different material if desired. For example, the anchor 60 may be formed of body tissue, such as bone or other dense connective tissue. The anchor 60 may be formed of many different materials containing collagen. The anchor 60 may be formed of natural or synthetic materials which absorb body fluid and expand when positioned in a patient's body. As the anchor expands in the patient's body, a solid interlock is obtained with adjacent tissue in the patient's body. The anchor 60 may be formed of any of the materials disclosed in the aforementioned U.S. Pat. No. 5,713,921 and/or U.S. Pat. No. 5,718,717.

Once the anchor 60 has been moved to the position illustrated in FIG. 3 by operation of the robotic mechanism 38, the suture 66 is tensioned with a predetermined force in the manner illustrated schematically by the arrow 70. To tension the suture 66, the robotic mechanism 38 (FIG. 1) includes a tensioner 122 (FIG. 3). The tensioner 122 determines when a predetermined tension force has been applied to the suture. The tensioner 122 is then effective to maintain the predetermined tension force.

The tensioner 122 and computer 44 may be set to limit the magnitude of the tension applied to the suture 66 to a preselected magnitude. Alternatively, the tensioner 122 and computer 44 may have a visual readout which enables a surgeon to determine the magnitude of the tension in the suture 66 and to maintain the tension in the suture at a desired magnitude. The image provided at the monitor 48 facilitates control of the tension in the suture 66 by the surgeon. If this is done, the tensioner 122 may be set to limit the tension in the suture to a desired maximum.

The tensioner 122 may include a gripper which grips the suture 66. A drive mechanism is operable to move to the gripper to tension the suture 66. The drive mechanism includes a pezielectric cell which detects when the tension transmitted from the gripper to the suture 66 has reached the predetermined magnitude. The drive mechanism may move the gripper to maintain the tension in the suture at the predetermined magnitude. Alternatively, the drive mechanism may respond to inputs from the surgeon.

Of course, the tensioner 122 could have a different construction if desired. For example, the tensioner 122 could include a spring, deflected through a predetermined distance to maintain a predetermined tension on the suture 66. The tensioner 122 could also have a construction similar to construction disclosed in U.S. patent application Ser. No. 09/556, 458 Filed May 3, 2000 by Peter M. Bonutti and entitled Method and Apparatus for Securing Tissue.

While the suture 66 is tensioned with a predetermined force by the tensioner 122, a retainer pusher member 126 is pressed against the retainer 72 with a predetermined force indicated schematically by an arrow 74 in FIG. 3. The retainer pusher member 126 is pressed against the retainer 72 by a pusher assembly 128 disposed in the robotic mechanism 38 (FIG. 1). The pusher assembly 128 includes a drive assembly which applies a predetermined force to the retainer pusher member 126. This force presses the retainer 72 against the upper layer 116 of body tissue 64.

While the retainer 72 is being pressed against the body tissue 64 with a predetermined force, the suture 66 is tensioned with a predetermined force by the tensioner 122. The force transmitted through the suture 66 presses the anchor 60 against the lower layer 118 of body tissue with a predetermined force. The force with which the anchor 60 is pressed against the body tissue 118 may be the same as, less than, or greater than the force with which the retainer is pressed against the tissue 116. This results in the two layers 116 and 118 of body tissue being clamped between the suture 60 and retainer 72 with a predetermined force.

The anchor 60 is pulled against a bottom surface 132 of the lower layer 118 of body tissue and the retainer 72 is pressed upper against the surface 134 of the upper layer 116 of body tissue. This results in the two layers 116 and 118 of body tissue being gripped between the retainer 72 and anchor 60 with a predetermined compressive force. This compressive force is a function of the sum of the tension force 70 transmitted to suture 66 by the tensioner 122 and the force 74 transmitted to the retainer pusher member 126 by the pusher assembly 128. A force distribution member, such as a button, may be provided between the anchor 60 and surface 132 of the body tissue 118. Another force distribution member may be provided between the retainer 120 and the surface 134 of the body tissue 116.

The pusher assembly 128 may have any desired construction, including for example, a hydraulically actuated piston and cylinder type motor in which the fluid pressure determines the magnitude of the force 74. Alternatively, an electric motor could be associated with a screw type drive and a force measurement device to apply the force 74 to the retainer pusher member 126. The force measurement device may be a piezoelectric cell or a spring assembly to control energization of the electric motor.

While anchor 60 and retainer 72 are being pressed against their respective body tissues, the robotic mechanism 38 is effective to plastically deform the retainer 72 to grip the suture 66. A retainer deformation assembly 144 (FIG. 4) in the robotic mechanism 38 is moved along the retainer pusher member 126 and suture 66 into engagement with the upper layer 116 of body tissue. A drive assembly 148 in the robotic mechanism 38 is effective to press the retainer deformation assembly 144 against the upper layer 116 of body tissue with a predetermined force. The force with which the retainer deformation assembly 144 is pressed against the upper layer 116 of body tissue may be of the same magnitude or less than the force 74 with which the retainer 72 is pressed against the upper layer 116 of body tissue by the robotic mechanism 38.

The retainer deformation assembly 144 includes a tubular cylindrical inner member 152 having a central cylindrical passage 154 in which the retainer pusher member 126 is telescopically received. A cylindrical outer member 156 extends around the cylindrical inner member 152 and is disposed in a coaxial relationship with the inner member 152 and retainer pusher member 126.

The force transmitting members 80 and 82 are carried by the inner member 152. When the inner member 152 is pressed against the upper layer 116 body tissue, the force transmitting members 80 and 82 are aligned with the suture retainer 72. At this time, the force transmitting members 80 and 82 are disposed below (as viewed in FIG. 4) a lower end of the pusher member 126 and are disposed radially outward from the spherical retainer 72.

When the retainer 72 is to be plastically deformed to grip the suture 66, the outer member 156 is moved downward (as viewed in FIG. 4) toward the upper layer 116 of body tissue by a drive assembly 160 disposed in the robotic mechanism 38. The drive assembly 160 presses the lower (as viewed FIG. 4) end of the outer member 156 against the force transmitting member 84 and 86 with a predetermined force, indicated schematically at 162 in FIG. 4. This force cams the force transmitting members 80 and 82 radially inward against the suture retainer 72.

The camming force 162 transmitted from the outer member 156 to the force transmitting members 80 and 82 causes the force transmitting members to move inward toward the suture retainer 72, as indicated by arrows 84 and 86. The force indicated by the arrows 84 and 86 causes the passage 120 (FIG. 3) to collapse and the material of the suture retainer 72 to move into engagement with and grip the suture 66. The manner in which the material of the retainer 72 is plastically deformed by the force transmitting members 80 and 82 may be the same as is disclosed in U.S. Pat. No. 6,159,234.

In order to facilitate deformation of the retainer 72, the material of the suture retainer may be heated. Heating of the material of the retainer 72 results in the material becoming soft and malleable under the influence of forces 84 and 86 applied by the force transmitting members 80 and 82. Ultrasonic vibratory energy is transmitted to the force transmitting member 82 from a source or generator 90 of ultrasonic vibratory energy. The force transmitting member 82 functions as a horn and applies the ultrasonic vibratory energy to the retainer 72. The force transmitting member 80 acts as an anvil which presses against the opposite side of the retainer 72.

As ultrasonic vibratory energy is transmitted to the retainer 72 and the temperature of the retainer increases, the material of the retainer is heated into its transition temperature range and softens. As the material of the retainer 72 softens, the forces 84 and 86 applied against the retainer by the force transmitting members 80 and 82 cause the material of the suture retainer to flow or ooze around and engage the suture 66.

The softened material of the retainer 72 engages the suture and bonds to the suture without significant deformation of the suture. Materials of the suture 66 and retainer 70 are chemically compatible so that a molecular bond can be established between the retainer and the suture. Like materials, that is materials having chemical properties which are the same or very similar, usually bond together. However, dissimilar materials may bond if their melt temperatures are reasonably close and they are of like molecular structure. Generally speaking, amorphous polymers are readily bonded to each other.

While it is preferable to heat the material of the retainer 72 by the application of energy, such as ultrasonic vibratory energy, other sources of energy could be used. For example, the retainer 72 could be heated by a laser or resistance wire. Regardless of whether or not the material of the retainer 72 is heated, the suture 66 is tensioned with the predetermined force 70. At the same time, the retainer 72 is urged toward the body tissue 64 of the predetermined force 74 when the retainer 72 is plastically deformed to grip the suture 66.

The anchor 60 could be formed out of body tissue in the manner disclosed in the aforementioned U.S. Pat. No. 5,713,921. The body tissue may be bone. If the anchor is formed of bone, the anchor may be formed with either the configuration illustrated in FIGS. 2-4 or may have a configuration similar to that disclosed in U.S. patent application Ser. No. 09/556,458 Filed May 3, 2000, by Peter M. Bonutti and entitled Method And Apparatus For Securing Tissue. Alternatively, the anchor could have any one of the constructions disclosed in U.S. Pat. Nos. 5,527,343; 5,534,012 and 5,718,717.

The inserter member 102 could have a construction different from the construction illustrated in FIG. 2. For example, the inserter member 102 could have a construction similar to any one of the constructions disclosed in U.S. Pat. No. 6,033,430.

Linear Apposition

The robotic mechanism 38 may be operated to place the layers 116 and 118 of body tissue in a side-by-side relationship, in the manner illustrated schematically in FIG. 5. When the layers of body tissue have been placed in the side-by-side relationship by the robotic mechanism 38, the pusher member 108 and inserter member 102 are utilized to move each of the anchors 60 in turn through the two layers 116 and 118 of body tissue in the manner previously discussed in connection with FIGS. 2-4 herein. While each of the sutures 66 in turn is tensioned, the retainer 72 is plastically deformed to securely grip the suture. Although each of the anchors 60, sutures 66 and retainers 72 of FIG. 5 was positioned relative to the body tissue 64 by the robotic mechanism 38 in turn, the robotic mechanism could be constructed so as to position a plurality of the anchor 60, suture 66 and retainers 72 relative to the body tissue 64 at one time.

Regardless of how the anchor 60, suture 66 and retainers 72 are positioned relative to the body tissue 64, each of the sutures 66 is tensioned so that it extends in a straight line between an anchor 60 and retainer 72 in the manner illustrated in FIG. 5. The anchors 60, sutures 66 and retainers 72 are spaced a desired distance apart along the edges of the body tissue 64 to secure the body tissue in linear apposition, as illustrated in FIG. 5. It is also possible that the layers 116 and 118 could be interconnected in a different manner if desired. For example, the robotic mechanism 38 could be operated to connect the layers 116 and 188 of body tissue in the manner disclosed in U.S. Pat. No. 5,549,631.

Under certain circumstances, body tissues are preferably joined in end-to-end relationship rather than the side-by-side relationship illustrated schematically in FIG. 5. For example, a break 172 may be formed between portions 174 and 176 of body tissue 64 (FIG. 6) by operation of the robotic mechanism 38. When the portions 174 and 176 of the body tissue are to be secure in this orientation, the suture anchor inserter member 102 and pusher number 108 (FIG. 2) are skewed at an acute angle relative to an upper (as viewed in FIG. 6) side surface 178 and to a lower side surface 180 of the portions 174 and 176 of the body tissue 64. Of course, the retainer deformation assembly 144 would also be skewed at a similar angle relative to the side surfaces 178 and 180 of the body tissue 64. This would allow the sutures 66 to be tensioned across the joint 172 between the two portions 174 and 176 of the body tissue 64. This would be particularly advantageous to provide the sutures 66 with the orientation illustrated in FIG. 6 when the portions 174 and 176 of body tissue to be interconnected are formed of bone.

A plurality of anchors 60, sutures 66 and retainer 72 may be provided across the break 172 between the portions 174 and 176 of a bone to be interconnected in the manner disclosed U.S. Pat. No. 6,117,160. It should be understood that the suture 66 could be utilized to connect soft body tissue with the portions 174 and 176 of bone in much the same manner as is disclosed in U.S. Pat. No. 6,117,160 and/or U.S. Pat. No. 6,152,949. The anchor 60, suture 66, and retainer 72 may be utilized to interconnect bone fragments in a manner similar to that disclosed in U.S. Pat. No. 6,117,160.

Plural Retainers

In the embodiments of the invention illustrated in FIGS. 2-6, an anchor 66 and retainer 72 have been connected with a suture. However, it is contemplated that a plurality of retainers 72 could be connected with a single suture. This could result in the suture 66 being tensioned between a pair of retainers 72 in the manner illustrated in FIG. 7 by operation of the robotic mechanism 38.

The two layers 116 and 118 of body tissue 64 (FIG. 7) are moved into a side-by-side relationship by operation of the robotic mechanism 38. The robotic mechanism 38 then utilizes a needle or other suture passer to move the suture 66 through the two layers of body tissue. The suture 66 may be moved through the body tissue 64 in the manner disclosed in U.S. patent application Ser. No. 10/005,652 filed Dec. 3, 2001, by Peter M. Bonutti for Magnetic Suturing System and Method. Of course, other known methods could be utilized in association with the robotic mechanism 38 to move the suture through the body tissue 64.

The retainers 72, (FIG. 7) are moved into engagement with the suture 66. The suture 66 is tensioned between upper and lower tensioners 122. While the suture 66 is tensioned by a pair of tensioners 122 (FIG. 7), a pair of retainer pusher members 126 press the retainers 72 against the upper and lower layers 116 and 118 of body tissue with predetermined forces, indicated by arrows 74 in FIG. 7. This results in the layers 116 and 118 of body tissue being firmly gripped between the upper and lower retainers 72 with a predetermined force.

While the suture 66 is being tensioned with a predetermined force and while the retainers 72 are being pressed against the layers 116 and 118 with a predetermined force, the pair of retainer deformation assemblies 144 are pressed against opposite sides of the body tissue 64 by drive assemblies 148. The retainer deformation assemblies 144 are pressed against the body tissue with a predetermined force which may be the same as the force with which the retainers 72 are pressed against the two layers 116 and 118 of body tissue.

The force transmitting members 80 and 82 are moved radially inward against spherical outer side surfaces of the upper and lower retainers 72. To press the force transmitting members 80 and 82 against the retainers 72 with a predetermined force, an upper tubular cylindrical outer member 156 is moved downward toward the upper layer 116 of body tissue 64 by a drive assembly 160. At the same time, a lower tubular cylindrical outer member 156 is moved upward toward the lower layer 118 of body tissue by a drive assembly 160, causing the upper and lower force transmitting members 80 and 82 to be jammed radially inward toward the retainers 72 to plastically deform the retainers and securely grip the suture 66.

As it was previously described in conjunction with the embodiment of the invention illustrated in FIG. 4 ultrasonic vibratory energy can be transmitted from a generator 90 connected with the upper force transmitting member 82 and from a generator 90 connected with the lower force transmitting member 82 to effect a heating of the material of the suture retainers 72. Of course, heat energy could be transmitted to the retainers 72 in a different manner if desired. Also, the retainers 72 could be plastically deformed without being heated.

Once the two retainers 72 have gripped the suture 66, the robotic mechanism 38 is operated to withdraw the retainer deformation assemblies 144 and pusher members 126, suitable cutters are then utilized to trim the suture 66. This may be accomplished in the manner disclosed in the aforementioned U.S. patent application Ser. No. 09/556,458 filed May 3, 2000.

A plurality of retainer and suture assemblies may be utilized to effect the linear apposition of body tissue in the manner illustrated in FIG. 8. The sutures 66 are tensioned and connected in a straight line relationship between retainers 72. This enables the sutures 66 and retainers 72 to hold the two layers 116 and 118 of body tissue in a side-by-side relationship with each other.

The linear apposition of the layers 116 and 118 of body tissue in the manner illustrated in FIGS. 5 and 8 and the linear interconnection of portions 174 and 176 of body tissue 64 in FIG. 6 result in a spot weld effect between separate pieces of body tissue at the locations where the sutures 66 extend through the of body tissue. The straight line connection provided by the suture 66 extending between either an anchor 60 and retainer 72 or two retainers 72, holds the portions 116 and 118 of body tissue against movement relative to each other when the patient's body moves. If the portions of body tissue were interconnected with a looped suture, the pieces of body tissue could shift relative to each other when the patient moves.

Although only a single suture 66 has been illustrated in FIG. 6, it should be understood that a plurality of sutures are disposed in a linear array along the joint 172. Although the suture 66 has been illustrated in FIG. 6 as being connected between an anchor 60 and retainer 72, the suture 66 could be connected a plurality of retainers 72 in the same manner as illustrated in FIG. 8.

In FIGS. 5 through 8, the anchors 60, sutures 66 and retainers 72 are preferably all formed of the same biodegradable polymeric material. However, it is contemplated that the anchors 60, sutures 66, and/or retainers 72 could be formed of different materials if desired. For example, the anchors 60 and/or retainers 72 could be formed of collagen. Alternatively, the anchors 60 and/or retainers 72 could be formed of body tissue, such as bone, in the manner disclosed in U.S. Pat. No. 5,713,921 and/or U.S. patent application Ser. No. 09/556,458 Filed May 3, 2000 and entitled Method and Apparatus For Securing Tissue.

Although it is preferred to utilize the robotic mechanism 38 to position the anchors 60, sutures 66 and retainers 72, they could be manually positioned in the body tissue if desired. For example, the anchors could be positioned in either hard or soft body tissue in the manner disclosed in U.S. Pat. No. 5,527,343 or U.S. Pat. No. 6,033,430. However, it is preferred to utilized the robotic mechanism 38 to position the anchors 60, sutures 66 and retainers 72 in the manner previously described in order to facilitate accurate positioning and tensioning of the sutures with minimally invasive surgery.

Tissue Positioning Assembly

A tissue positioning assembly 200 (FIGS. 9-15) forms part of the robotic mechanism 38 (FIG. 1), but may be manually operated separately. Although the tissue positioning assembly 200 is advantageously utilized in conjunction with the robotic mechanism 38, it may be utilized without the robotic mechanism 38. Thus, the tissue positioning assembly may advantageously be utilized when body tissue 64 is to be manually secured utilizing prior art methods.

The tissue positioning assembly 200 includes a long thin member 202 connected with and moved by the robotic mechanism 38. The long thin member 202 has a leading end portion 204 which is utilized to pierce the layers 116 and 118 of body tissue 64. The leading end portion 204 of the long thin member 202 is pointed to facilitate piercing imperforate surface areas on the layers 116 and 118 of body tissue 64.

The long thin member 202 is illustrated in FIG. 9 as being moved through the layers 116 and 118 of body tissue while there is a space 208 between the layers of body tissue. Although it is believed that the long thin member 202 may advantageously pierce imperforate surfaces on the layers 116 and 118 of body tissue 64 while they are spaced apart in the manner illustrated schematically in FIG. 9, the long thin member 202 may be utilized to pierce the layers 116 and 118 of body tissue while they are disposed in engagement with each other. The long thin member 202 pierces the layers 116 and 118 of body tissue under the influence of force transmitted to the long thin member from the robotic mechanism 38, but may be moved manually.

The tissue positioning assembly 200 may be utilized in association with two or more pieces of bone. Thus, the long thin member 202 could be moved across a fracture or break in a bone or could extend through a main portion of a bone and a bone fragment during interconnection of the separate portions of the bone in a manner similar to that disclosed in U.S. Pat. No. 6,045,551. Similarly, the tissue positioning assembly 200 may be used with both hard and soft body tissue, as disclosed in U.S. Pat. No. 5,527,343 and/or U.S. patent application Ser. No. 09/789,621 filed Feb. 21, 2001, by Peter M. Bonutti and entitled Method of Securing Body Tissue.

The leading end portion 204 of the long thin member 202 is expandable from the contracted condition of FIG. 9 to the expanded condition of FIG. 10 after the long thin member 202 has been inserted through the two layers 116 and 118 of body tissue and while the space 208 is present between the two layers of body tissue. Once the leading end portion 204 of the long thin member 202 has been expanded, a force indicated schematically in 212 in FIG. 10, is applied to the long thin member 202. The axial force applied to the long thin member 202 pulls the long thin member upward (as viewed in FIGS. 9 and 10).

As the long thin member 202 is pulled upward, the expanded leading end portion 204 (FIG. 10) moves into abutting engagement with a surface on the lower layer 118 of body tissue 64. The force 212 is transmitted from the expanded leading end portion 204 to the lower (as viewed in FIG. 10) surface 132 of the layer 118 of body tissue. The force 212 is transmitted to the long thin member 202 from the robotic mechanism 38. However, the force 212 could be manually applied to the long thin member if desired.

The force on the lower layer 118 of body tissue pulls the lower layer of body tissue upward toward the upper layer 116 of body tissue, eliminating space 208 (FIG. 9) between the layers 116 and 118 of body tissue. Therefore, an upper surface of the layer 118 of body tissue moves into engagement with a lower surface of the layer 116 of body tissue.

The tissue positioning assembly 200 may be used to move the layers 116 and 118 of body tissue together to a desired position in a patient's body. Thus, after the upper and lower layers 116 and 118 of body tissue 64 have been moved into engagement (FIG. 10), they may be moved sidewardly in the patient's body. This may be accomplished by applying, to the long thin member 202, a force which extends transverse to central axis of the long thin member. This transverse force moves the long thin member 202 and the layers 116 and 118 of body tissue to either the left or the right as viewed in FIG. 10. The transverse force can be transmitted from the robotic mechanism or manually applied.

If desired, a cannulated anchor 216 (FIG. 11) may be moved along the long thin member 202 into the body tissue 64. The anchor 216 is moved under the influence of force applied against the trailing end of the anchor 216 by a tubular cylindrical pusher member 220 (FIG. 11). The pusher member 220 has a cylindrical central passage 222 through which the long thin member 202 and suture 66 extend. The suture 66 is connected to the cannulated anchor 216.

The pusher member 220 applies an axial force to the cannulated anchor 216. This force slides the anchor 216 along the long thin member 200 to move the anchor 216 through the upper (as viewed in FIG. 11) layer 116 of body tissue into the lower layer 118 of body tissue.

As the anchor 216 moves through the lower layer 118 of body tissue to a position adjacent to the expanded leading end portion 204, the leading end portion 204 is returned to the contracted condition of FIG. 9. The anchor 216 is then pushed downward (as viewed in FIG. 11) through the lower layer 118 of body tissue, becoming disengaged from the long thin member 202. Thus, the cannulated anchor 216 is pushed or slid off of the contracted leading end portion 204.

The long thin member 202 is then withdrawn from the body tissue 64 and, contemporaneously with withdrawal of the long thin member 202, the anchor 216 is pivoted or toggled to the orientation of the anchor 60 in FIG. 3. Once this has been accomplished, tensioning of the suture 66 is effective to press the anchor 216 firmly against the surface 132 of the lower (as viewed in FIG. 11) layer 118 of body tissue.

A retainer 72 is then pressed against the upper layer 116 of body tissue by a retainer pusher member, corresponding to the retainer pusher member 126 of FIG. 3. While the retainer is pressed against the body tissue with a predetermined force and the suture 66 is tensioned with a predetermined force, the suture retainer is deformed to grip the suture 66 in the same manner as previously described in conjunction with FIG. 4.

The cannulated anchor 216 has been illustrated as having a fustro conical leading end 226 which is connected with a cylindrical body 228. The conical configuration of the leading end 226 of the anchor facilitates movement of the anchor through the body tissue 64 under the influence of force applied against the trailing end of the anchor by the pusher member 220. However, the anchor 216 could have a different configuration, for example, a configuration corresponding to the configuration of the anchors FIGS. 2 and 3 herein.

The long thin member 202 is moved into the body tissue 64, the leading end portion 204 expanded, and the long thin member pulled upward, as viewed in FIG. 10, under the control of the robotic mechanism 38. However, these steps could all be performed apart from the robotic mechanism 38 if desired. For example, these steps could be performed by a mechanism which is separate from the robotic mechanism 38. Alternatively, these steps could be performed manually.

In the embodiment illustrated in FIG. 11 the anchor 216 is moved along the long thin member 202 with a central axis of the anchor coincident with a central axis of the long thin member. In the embodiment illustrated in FIG. 12, the anchor 60 is moved along the long thin member with the anchor offset to one side of the long thin member. As the anchor 60 transmits a downwardly directed (as viewed in FIG. 12) force from the pusher member 108 to the body tissue 64, the long thin member 202 transmits an upwardly directed force 212 to the body tissue. As was previously mentioned, the long thin member 202 may also apply a sideward force, that is, a force transverse to the central axis of the long thin member, to the body tissue 64. The results in the body tissue 64 being maintained in a desired position during movement of the anchor 60 through the layer 116 of body tissue into the layer 118 of body tissue.

Figure 12:
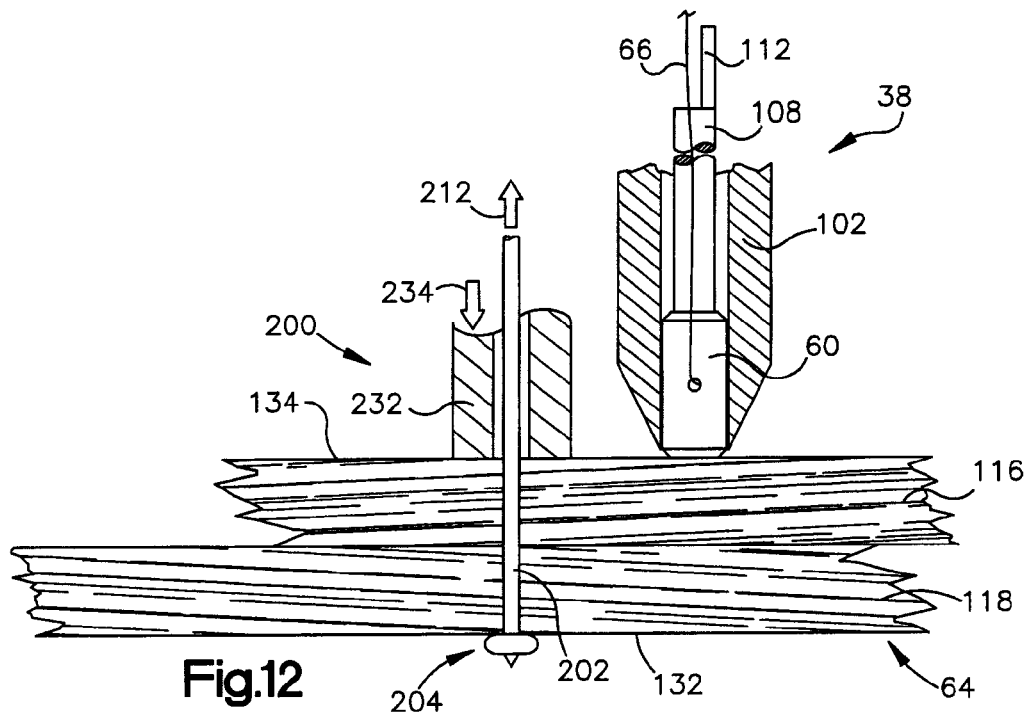
FIG. 12 is a schematic illustration depicting the manner in which a gripper member is moved along the long thin member of FIG. 10 by the robotic mechanism of FIG. 1 to grip body tissue and an alternative manner in which a fastener is moved into the gripped body tissue by the robotic mechanism.

The anchor 60 may be pivoted or toggled in the layer of body tissue 118 in response to axially downward movement of the push rod 112 (FIG. 12). As the push rod 112 is pressed downward against the anchor 60 by the robotic mechanism 38, a torque is applied to the anchor 60. This torque causes the anchor 60 to pivot and deflect body tissue 118 in the manner disclosed in U.S. Pat. No. 6,033,430. Once the anchor 60 has pivoted to the orientation shown in FIG. 3 with the anchor enclosed by the body tissue 118, tension forces in the suture 66 are transmitted through the anchor 60 to the body tissue 118. Downward forces applied to the body tissue 64 by the anchor 60 during pivoting of the anchor are offset by upward force transmitted through the thin elongated member 202 to the body tissue.

After the anchor 60 has been pivoted to the desired orientation in the body tissue 118, the long thin member 202 is withdrawn from the two layers 116 and 118 of body tissue 64. Before this can be done, the leading end portion 204 of the long thin member 202 is operated from the expanded condition of FIG. 12 to the contracted condition of FIG. 9. The long thin member 202 can then be pulled from the body tissue 64 by either operation of the robotic mechanism 38 or the application of manual force to the long thin member.

Although the anchor 60 has been described above as moving only part way through the lower layer 118 of body tissue, the anchor 60 could be moved completely through the lower layer 118 of body tissue and into the orientation shown in FIG. 3. Tensioning the suture 66 would then result in force being transmitted from the anchor 60 to the lower (as viewed in FIG. 12) surface 132 of the layer 118 of body tissue.

It is contemplated that it may be desired to grip the two layers 116 and 118 of body tissue with a clamping action. When this is to be done, a tubular cylindrical gripper member 232 is pressed against the surface 134 on the upper (as viewed in FIG. 12) layer 116 of body tissue 64. This clamps the two layers 116 and 118 of body tissue between the gripper member 232 and the expanded leading end portion 204 of the long thin member 202. Thus, the long thin member 202 is pulled upward (as viewed in FIG. 12) with the force 212 to press the expanded leading end portion 204 of the long thin member against the lower surface 132 of the layer 118 of body tissue.

At the same time, the gripper member 232 is pressed against the upper surface of the layer 116 of body tissue with a force indicated at 234 in FIG. 12.

The anchor 60 is moved along the long thin member 202 into the body tissue 64 at a location offset to one side of and disposed adjacent to the long thin member 202. The tissue positioning assembly 200 (FIG. 12) is effective to grip the body tissue 64 between the gripper member 232 and the expanded end portion 204 of the long thin member 202. The tissue positioning assembly 200 is effective to hold the gripped body tissue 64 in any desired position in the patient's body.

The gripped body tissue 64 can be moved to any desired position in the patient's body by moving the long thin member 202 and gripper member 232. Thus, the long thin member 202 and gripper member 232 can be moved upward, downward, and/or sideward while gripping the body tissue 64. The long thin member 202 and gripper member 232 can be moved manually or by the robotic mechanism 38 to move the body tissue 64 to a desired location in a patient's body.

While the anchor 60 is pushed through the two layers 116 and 118 of body tissue by the pusher member 108 as previously described in conjunction with FIG. 2 herein, the body tissue is gripped by the long thin member 202 and gripper member 232. Since the body tissue 64 is securely held, the body tissue does not move under the influence of force transmitted from the pusher member 108 through the anchor 60 to the body tissue as the anchor moves through the body tissue. Thus, when the anchor 60 moves into the body tissue, the anchor applies a force which urges the body tissue to move downward (as viewed in FIG. 12). The upward (as viewed in FIG. 12) force 212 transmitted to the leading end portion 204 of the long thin member 202 through the body tissue 64 holds the body tissue in a desired position as the anchor 60 moves into the body tissue. In addition, the long thin member 202 is effective to hold the body tissue against sideways movement during insertion of the anchor 60 into the body tissue.

Once the anchor 60 has been moved to a desired position relative to the body tissue 64, the long thin member 202 and gripper member 232 (FIG. 12) hold the gripped body tissue in a desired position against the influence of force transmitted through the suture 66. This enables the suture 66 to be tensioned without moving the body tissue 64. After the suture 66 has been connected in any desired manner, the long thin member 202 and gripper member 232 are disengaged from the body tissue 64.

It is preferred to have the tissue positioning assembly 200, the inserter member 102, and the pusher member 108 be part of the robotic mechanism 38. The force transmitted from the robotic mechanism to the inserter member 102 and pusher member 108 enables the anchor 60 to be pushed into the body tissue 64 with a desired force. However, it should be understood that the tissue positioning assembly 200, the inserter member 102, and the pusher member 108 could be separate from the robotic mechanism 38 and could be manually operated.

The tissue positioning assembly 200 may also be utilized to indicate the depth to which the anchor 60 must be moved into the body tissue 64 by the pusher member 108. The leading ending portion 204 of the long thin member 202 (FIG. 12) is disposed at a known depth relative to the body tissue. By moving the anchor 60 to a depth which slightly exceeds the depth of the leading end portion 204 of the long thin member 202, the anchor 60 is pushed to a known depth relative to the body tissue.

An encoder connected with a drive assembly in the robotic mechanism 38 may be utilized to indicate the depth to which the long thin member 202 is moved into the patient's body. By comparing the depth of the thin member 202 in the patient's body with the depth to which the gripper member 232 is moved into the patient's body, the thickness of the body tissue 64 can be determined. This enables the robotic mechanism 38 to move the inserter member 102 to a position in engagement with the upper surface 134 of the layer 116 of body tissue 64. It also enables the robotic mechanism 38 to be operated to move the pusher member 108 through a distance sufficient to push the anchor 60 through both the upper layer 116 of body tissue and the lower layer 118 of body tissue to the position corresponding to the position illustrated in FIG. 3. If desired, the anchor 60 may be moved to a position in the lower layer 118 of body tissue.

When the tissue positioning assembly 200, inserter member 102, and pusher member 108 are to be manually moved relative to the body tissue 64, indicia to indicate the depth of movement of the various members may be provided on the outside of various members. The indicia may be numerical indicia indicating the depth of insertion of a member into the body tissue. Alternatively, the indicia may be colored bands or other markings. If the indica is to be colored bands, the indicia may be similar to the indicia disclosed in U.S. Pat. No. 6,056,772.

Once the anchor 60 (FIG. 12) has been moved through layers 116 and 118 of the body tissue 64 while the tissue positioning assembly 200 grips the body tissue and holds it into a desired position, the suture 66 is tensioned with a predetermined force and a retainer is deformed to grip the suture. The retainer may have the same construction as the retainer 72 of FIG. 4. Alternatively, the suture retainer may have any one of the constructions disclosed in U.S. Pat. No. 6,159,234.

A retainer deformation assembly having the same construction as the retainer deformation assembly 144 (FIG. 4) may be utilized to deform the retainer to grip the suture 66 of FIG. 12. This results in the body tissue 64 being clamped or gripped between the anchor 60 and a retainer 72 which grips the suture 66. This holding or gripping action would be the same as was previously described in conjunction with FIGS. 2-4 herein. Of course, other known retainer deformation assemblies could be utilized if desired, as noted above.

Once the body tissue has been gripped between the anchor 60 and the retainer 72 and the retainer secured to the suture 66, the tissue positioning assembly 200 is disengaged from the body tissue as noted above.

Figure 13:
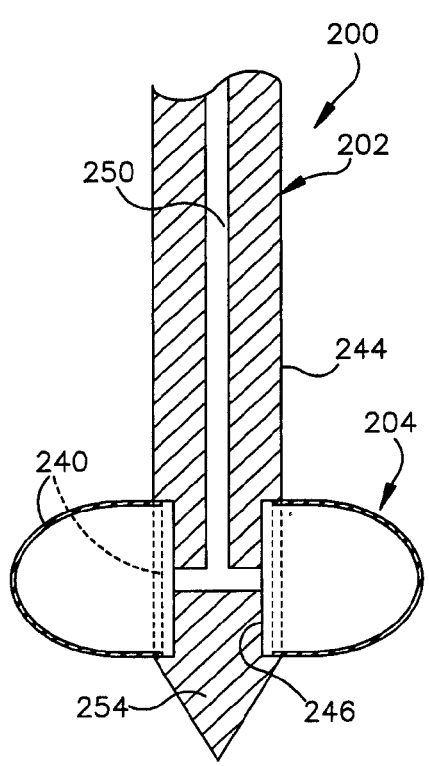
FIG. 13 is an enlarged, fragmentary sectional view further depicting the manner in which the leading end portion of the long thin member of FIG. 9 is expanded by the robotic mechanism of FIG. 1.

It is contemplated that the leading end portion 204 of the long thin member 202 may include a resilient panel 240 (FIG. 13). The panel 240 is moved from a contracted condition, shown in dashed lines in FIG. 13, to the expanded condition of FIGS. 10, 11, 12 and 13 with fluid pressure. When the leading end portion 204 of the long thin member 202 is in the contracted condition of FIG. 9, the resilient panel collapses radially inward from the expanded condition to the contracted condition under the influence of its own natural resilience. When the panel 240 is in the contracted condition, a cylindrical outer side surface of the resilient panel 240 is aligned with a cylindrical outer side surface 244 of the long thin member 202. At this time, the resilient panel 240 is disposed in an annular recess 246 formed in the leading end portion 204 of the long thin member 202.

When the leading end portion 204 of the long thin member 202 is to be expanded, fluid under pressure is conducted through a passage 250 in the long thin member to the annular recess 246 in the leading end portion of the long thin member. This fluid pressure is applied against an inner side surface of the resilient panel 240. The fluid pressure forces the resilient panel 240 to expand outward to the annular configuration illustrated in solid lines in FIG. 13. The fluid pressure applied against the inner side of the panel 240 could be either a liquid or gas pressure. Thus, the robotic mechanism 38 is operable force either a gas or a liquid through the passage 250.

When relatively large forces are to be transmitted from the leading end portion 204 of the long thin member 202 to the body tissue 64, it may be preferred to utilize a liquid to effect radial expansion of the panel 240. When somewhat smaller forces are to be transmitted from the long thin member 202 to the body tissue 64, the resilient panel 240 may be expanded under the influence of gas pressure.

The long thin member 202 has a pointed end 254 which is utilized to pierce imperforate areas on upper and lower surfaces of the upper layer 116 of body tissue and on upper and lower surfaces of the lower layer 118 of body tissue. The pointed end 254 of the long thin member 202 is coaxial with the longitudinal central axis of the long thin member and has a conical configuration. The pointed end 254 of the long thin member 202 is immediately ahead of and coaxial with the resilient panel 240.

The resilient panel on the leading end portion 204 of the long thin member may be formed of any desired resilient material which can be expanded under the influence of fluid pressure. It is contemplated that the resilient panel 240 will be formed of a polymeric material. The remainder of the long thin member 202 may be formed of either metal or a polymeric material.

Figure 14:
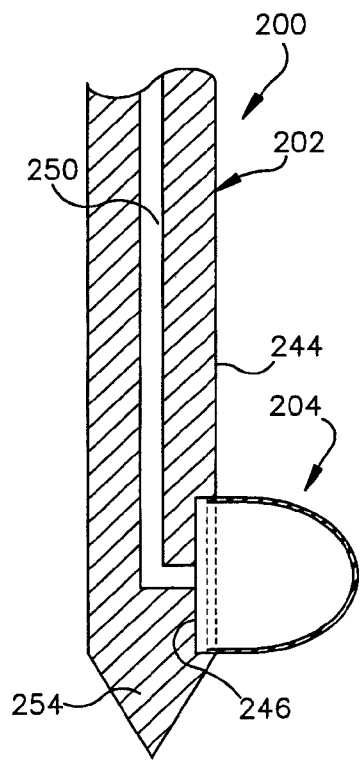
FIG. 14 is an enlarged, fragmentary sectional view depicting another manner in which the leading end portion of the long thin member of FIG. 9 may be expanded by the robotic mechanism of FIG. 1.

An alternative embodiment of the long thin member 202 is illustrated in FIG. 14. In this embodiment, the resilient panel 240 is formed as a portion of a circle. This results in the resilient panel bulging outward from one side of the long thin member 202 when fluid pressure is connected through the passage 250 to a recess 246 in the leading end portion 204 of the long thin member 202. The recess 246 has a configuration corresponding to a portion of a cylinder.

When the leading end portion 204 is in the contracted condition, the resilient panel 240 is disposed in the position indicated in dash lines in FIG. 14. At this time, the resilient panel 240 is disposed within the recess 246. When fluid pressure is conducted through the passage 250 to the recess 246, the resilient panel 240 is expanded radially outward from the long thin member 202 to the position shown in solid lines in FIG. 14. Other than the configuration of the resilient panel 240, the long thin member 202 of FIG. 14 has the same construction as the long thin member 202 of FIG. 13.

In the embodiment of the long thin member 202 illustrated in FIG. 15, a plurality of longitudinally extending elements 260 are disposed in a cylindrical array on the leading end portion 204 of the long thin member 202. The longitudinally extending elements 260 are spaced apart from each other and have longitudinal central axes extending parallel to a longitudinal central axis of the long thin member 202. The longitudinally extending elements 260 are pivotally connected at 264 to a cylindrical main portion 266 of the long thin member 202. A pointed end 254 of the long thin member 202 is connected with a cylindrical actuator rod 268 which extends through the main portion 266 of the long thin member to the pointed end 254. By pulling upwards (as viewed in FIG. 15) on the long thin member, the longitudinally extending elements 260 are bent at central pivots 272. The long thin elements are connected with the pointed end 254 at pivots 274.

Pulling upward, in the manner indicated by an arrow 276 in FIG. 15 transmits force through the actuator rod 268 to the pointed end 254 of the long thin member 202. This moves the pointed end 254 of the long thin member toward the main portion 266 of the long thin member. As this occurs, the longitudinally extending elements 260 are bent at the pivot connections 264, 272 and 274 and move radially outward away from a longitudinal central axis of the long thin member 202. This results in the longitudinally extending elements performing an annular projection which extends around the long thin member 202. This annular projection is pressed against body tissue by pulling upward on the main portion 266 of the long thin member 202.

The longitudinally extending elements 260 of FIG. 15 are formed separately from the main portion 266 of the long thin member 202. However, the longitudinally extending elements 260 may be integrally formed as one piece with the main portion 266 of the long thin member 202. If this was done, the longitudinally extending elements 260 would be resiliently deflected radially outward from the contracted condition to the expanded condition. This may be accomplished in the manner disclosed in U.S. Pat. No. 5,667,520.

Although the long thin member 202 has been illustrated in FIGS. 9-12 in association with layers 116 and 118 of soft body tissue 64, it is contemplated that the long thin member 202 could be utilized with hard body tissue if desired. For example, the pointed leading end 254 of the long thin member 202 could be forced through a hard cortical outer layer of a portion of a bone in a patient's body. Alternatively, the leading end portion 204 could be moved into the bone through a drilled passage.

The leading end portion 204 of the long thin member 202 would then be expanded in the bone, under the influence of fluid pressure and/or force transmitted through the long thin member. Expansion of the leading end portion 204 of the long thin member 202 would deflect the relatively soft consellous bone enclosed by the hard cortical outer layer of bone. This would result in the long thin member being secured with the bone.

After the leading end portion 204 of the long thin member 202 has been expanded in a bone, the gripper member 232 (FIG. 12) may be moved axially along the long thin member 202 to press soft body tissue, such as the layer 116 of soft body tissue, against the bone. This would result in the soft body tissue and the hard cortical outer layer of the bone being gripped between the leading end portion 204 of the long thin member 202 and the gripper member 232 in the same manner as in which the layers 116 and 118 of soft body tissue are clamped between the gripper member 232 and the expanded leading end portion 204 of the long thin member 202 in FIG. 12.

In the embodiment illustrated in FIGS. 9-12, the leading end portion 204 of the long thin member 202 is moved through the body tissue and is effective to apply force against an outer surface 132 of the lower layer 118 of body tissue. However, it is contemplated that the long thin member may be moved only part way through the layer 118 of body tissue. This would result in the leading end portion 204 of the long thin member being operated from the contracted condition of FIG. 9 to the expanded condition of FIGS. 11 and 12 while the leading end portion of the long thin member is disposed in the layer 118 of body tissue. As the leading end portion 204 of the long thin member is expanded in the layer 118 of body tissue, the outer side surface of the resilient panel 240 applies force against the soft tissue of the layer 118 to move the tissue sufficiently to accommodate expansion of the leading end portion 204 of the long thin member 202.

When the tissue positioning assembly 200 is to be used in association with a fractured bone or bone fragments, the long thin member 202 is moved through portions of the bone while the leading end portion 204 of the long thin member is in the contracted condition. Once the leading end portion 204 of the long thin member 202 has moved through portions of the bone separated by a fracture or break, the leading end portion of the long thin member may be expanded. The expanded leading end portion 204 of the long thin member 202 would engage an outer surface of a portion of a bone in the same manner as in which the expanded leading end portion engages an outer surface of the tissue layer 118 in FIGS. 10-12.

A gripper member, corresponding to the gripper member 232 of FIG. 12, is then moved axially along the long thin member 202 to press the portion of the bone disposed on one side of the fracture against a portion of the bone disposed on the opposite side of the fracture. In this instance, the leading end portion 204 of the long thin member 202 is expanded at a location outside of the bone. However, in other situations, it may be advantageous to expand the leading end portion 204 of the long thin member 202 in the bone. The relatively soft cancellous bone can be deflected by expansion of the leading end portion 204 of the long thin member 202 in a bone.

In the embodiment of the tissue positioning assembly 200 illustrated in FIGS. 16-19, the long thin member 202 has a leading end portion 204 with an external thread convolution 278. When the long thin member 202 is rotated about its longitudinal central axis, the external thread convolution 278 engages body tissue. This enables force to be transmitted from the long thin member 202 to the body tissue engaged by the external thread convolution 278. The body tissue 64 can then be moved to and held in a desired position in a patient's body.

When the tissue positioning assembly 200 is to be utilized to position the layers 116 and 118 of the body tissue 64 relative to each other, the long thin member 202 is extended through the upper (as viewed in FIG. 16) layer 116 of body tissue. This may be done by forcing the long thin member 202 to move axially through the layer 116 of body tissue with a piercing action. Alternatively, the long thin member 202 may be rotated about its longitudinal central axis. As the long thin member 202 is rotated, force is transmitted between the body tissue 116 and the external thread convolution 278. This force is effective to pull the long thin member 202 through the body tissue 116. In order to minimize damage to the body tissue 116, the long thin member 202 should rotate about its longitudinal central axis so that the external thread convolution 278 engages the body tissue 116 and is effective to pull the long thin member 202 through the body tissue.

Once the long thin member 202 (FIG. 16) has moved through the upper layer 116 of body tissue, the external thread convolution 278 on the leading end portion 204 of the long thin member 202 moves into engagement with an upper side surface of the layer 118 of body tissue. When this happens, the long thin member 202 is again rotated about its longitudinal central axis. This causes the external thread convolution 278 to engage the lower layer 118 of body tissue with a screw action. The screw action between the thread convolution 278 and lower layer 118 of body tissue is effective to pull the long thin member 202 into the lower layer 118 body tissue. When the external thread convolution 278 has been screwed into the lower layer 118 of body tissue to a desired depth, rotation of the long thin member 202 about its longitudinal central axis is interrupted.

In order to close a space 208 between the upper layer 116 and the lower layer 118 body tissue 64, the long thin member is pulled upward as indicated by the arrow 212 in FIG. 17. The upward force 212 applied to the long thin member is transmitted through the external thread convolution 278 to the lower layer 118 of body tissue. This pulls the lower layer 118 of body tissue upwards (as viewed in FIGS. 16 and 17) into engagement with the upper layer 116 of body tissue. If desired, the gripper member 232 (FIG. 12) may be used with the long thin member 202 of FIGS. 17 and 18 to grip body tissue in the manner previously explained.

Once the two layers 116 and 118 of body tissue have been moved to a desired position in the patient's body by the tissue positioning assembly 200, the anchor 60 (FIG. 18) may be moved into the body tissues 116 and 118 by the robotic mechanism 38 in the same manner as previously discussed in conjunction with FIGS. 2 and 3. Thus, the inserter member 102 may be moved into engagement with the upper layer 116 of body tissue. The pusher member 108 then applies force against the anchor 60 to push the anchor through the lower layer 116 of body tissue and into the lower layer 118 of body tissue. As was previously mentioned, the anchor 60 may be pushed through the lower layer 118 of body tissue or have its movement into the lower layer interrupted when it is midway between upper and lower side surfaces of the lower layer 118 of body tissue.

While the anchor 60 is being pushed into the body tissue 116 and the body tissue 118, an upwards force 212 is transmitted from the long thin member 202 through the external thread convolution 278 to the lower layer 118 of body tissue. This force holds the lower layer of body tissue in engagement with the upper layer 116 of body tissue in the manner illustrated schematically in FIG. 18.

It is contemplated that the long thin member 202 may be utilized as part of a fastener to interconnect the two layers 116 and 118 of body tissue in the manner illustrated schematically in FIG. 19. When this is to be done, a retainer 72 is positioned along the long thin member 202 with the long thin member extending through the retainer (FIG. 19). The retainer pusher member 126 is then effective to press the retainer 72 against the upper layer 116 of body tissue.

The retainer deformation assembly 144 can then be utilized to deform the retainer 72 in the manner previously discussed in conjunction with FIG. 4. As force is applied against the retainer 72 by the force transmitting members 80 and 82, the retainer 72 is deformed and grips the long thin member 202 to establish an interconnection between the retainer and the long thin member. This interconnection results in force being transmitted through the long thin member 202 between the external thread convolution 278 which engages the lower layer 118 of body tissue and the retainer 72 which engages the upper layer 116 of body tissue. After the retainer 72 has gripped the long thin member 202, the retainer pusher member 126 and retainer deformation assembly 144 are removed from the patient's body. This results in the long thin member 202 and the retainer 72 functioning as a fastener to interconnect the two layers 116 and 118 of body tissue.

The long thin member 202, the external thread convolution 278, and the retainer 72 may be formed of either biodegradable or non-biodegradable material. When the long thin member 202, external thread convolution 278 and retainer 72 are formed of biodegradable material, they will degrade and be absorbed by the patient's body with passage of time. However, when the long thin member 202, external thread convolution, and retainer 72 are formed of non-biodegradable material, they are effective to maintain the two layers 116 and 118 of body tissue in engagement with each other, in the manner illustrated in FIG. 19, for a long period of time.

The long thin member 202 and external thread convolution 278 are illustrated in FIG. 19 in association with soft body tissue. However, it is contemplated that the long thin member 202 and external thread convolution may be utilized in association with hard body tissue, such as bone. When this is to be done, the external thread convolution 278 of the long thin member 202 may be screwed into the bone. Alternatively, the long thin member 202 and external thread convolution 278 may be moved through a passage drilled in the bone and into a layer of soft tissue. This would enable force to be transmitted from the external thread convolution 278 to the layer of soft tissue to pull the layer of soft tissue into engagement with the bone.

It is believed that it may be particularly advantageous to utilize the external thread convolution 278 in association with the long thin member 202 when pieces of bone are to be positioned relative to each other. Thus, the long thin member 202 may be moved through a passage drilled or formed in another manner, in one piece of bone and the external thread convolution moved into engagement with a second piece of bone. The long thin member 202 would then be rotated about its central axis to screw the external thread convolution 278 into the second piece of bone. Force applied to the long thin member 202 could then be utilized to pull the second piece of bone into engagement with the first piece of bone.

It is also contemplated that the long thin member 202 and external thread convolution 278 may be advantageously utilized to close a fracture or break in a bone. This is because the thread convolution 278 may engage one portion of the bone to enable it to be pulled into engagement with another portion of the bone. Once the two portions of the bone have been pulled into engagement with each other, they may be interconnected in the manner disclosed in U.S. Pat. No. 6,117,160. Alternatively, they may be interconnected by securing a retainer 72 to the long thin member 202 in the manner previously discussed herein.

Securing with Suture and Retainer

In the embodiments of the invention illustrated in FIGS. 2-8 the suture 66 extends in a straight line between an anchor 60 and a retainer 72 or in a straight line between two retainers. However, under certain circumstances at least, it may be desired to form the suture 66 into a loop which extends through body tissue 64 in the manner illustrated in FIG. 20.

The suture 66 is sewn through the two layers 116 and 118 of body tissue using a needle or other known device. The suture is moved through the body tissue 64 by the robotic mechanism 38. It is contemplated that the magnetic suturing system and method disclosed in the aforementioned U.S. patent application Ser. No. 10/005,652, will be used by the robotic mechanism 38. Alternatively, the needle could be manually moved through the two layers 116 and 118 of body tissue 64.

The suture 66 has a connector section 280 (FIG. 20) which extends between a pair of a leg sections 282 and 284. The leg sections 282 and 284 extend through the layers 116 and 118 of tissue 64 to the retainer 72. The leg sections 282 and 284 extend through the retainer 72 and are tensioned by a tensioner 122 which applies a predetermined force 70 to the two leg sections 282 and 284 of the suture 66.

While the suture 66 is being tensioned with the predetermined force 70, the retainer 72 is pressed against the body tissue 64 by the retainer pusher member 126. The retainer pusher member 126 is pressed against the retainer 72 by the pusher drive assembly 128. The pusher drive assembly 128 causes the retainer pusher member 126 to press the retainer 72 against the body tissue 64 with a predetermined force indicated at 74 in FIG. 16. This results in the retainer member 72 being pressed against the body tissue 64 with a predetermined force while the leg sections 282 and 284 and connector section 280 of the suture 66 are tensioned with a predetermined force.

While the retainer 72 is pressed against the body tissue, the retainer deformation assembly 144 deforms a retainer 72 to grip the two leg sections 282 and 284 of the suture 66. Thus, the outer member 156 is moved axially downward, as viewed in FIG. 20, to move the force transmitting members 80 and 82 radially inward toward the spherical retainer 72. The force applied to the retainer 72 by the force transmitting members 80 and 82 deforms the retainer so that it grips the sutures 66. As was previously explained, the force transmitting members 80 and 82 may be utilized to cause a cold flow of the material of the retainer 72 to grip the two legs 282 and 284 of the suture 66. Alternatively, ultrasonic vibratory energy from a source 90 may be transmitted to the force transmitting member 82 and the retainer 72 to heat the retainer.

Although the retainer has been illustrated in FIG. 16 as having a spherical configuration, it is contemplated that the retainer 72 could have a different configuration if desired. For example, the retainer 72 could have any one of the configurations disclosed in U.S. Pat. No. 6,159,234. The manner in which the retainer 72 is plastically deformed to grip the two legs 282 and 284 of the suture 66 may also be the same as is disclosed in the aforementioned U.S. Pat. No. 6,159,234. Alternatively, the retainer 72 may be heated and then deformed in the manner disclosed in the aforementioned U.S. patent application Ser. No. 09/524,397 or in U.S. Pat. No. 6,203,565.

In order to facilitate positioning of the suture 66 (FIG. 20) relative to the body tissue 64, iron particles may be embedded in the suture throughout the length of the suture. To move the suture 66 to a desired position in the patient's body, a magnet is positioned close enough to the suture 66 to attract the iron particles in the suture. The magnet is then moved relative to the body tissue to move the suture 66 relative to the body tissue. The magnet may be positioned inside the patient's body or outside the patient's body. The magnet may be electromagnet or a permanent magnet.

Similarly, iron particles may be embedded in the suture retainer 72. To move the suture retainer 72 to a desired position in the patient's body, a magnet is positioned close enough to the retainer to attract the iron particles in the retainer. The magnet is then moved relative to the body tissue to move the suture retainer 72 relative to the body tissue. The magnet may be positioned inside the patient's body or outside the patient's body. The magnet may be an electromagnet or a permanent magnet.

When iron particles are to be provided in the suture 66 and/or retainer 72, the suture and/or retainer may advantageously be formed of a biodegradable material. As the biodegradable material of the suture 66 and/or retainer 72 degrades in the patient's body, the iron particles also degrade. The iron particles are subsequently absorbed by the patient's body.

Staple-Bonded
Leg Ends

In the embodiments of the invention illustrated in FIGS. 2-8, the robotic mechanism 38 is utilized to secure body tissue with a suture 66. However, it is contemplated that a staple 300 (FIGS. 21 and 22) may be utilized to secure the body tissue 64. When the staple 300 is utilized to secure the body tissue, end portions 302 and 304 of legs 306 of the staple are moved into engagement (FIG. 22) and bonded together. By bonding the end portions 302 and 304 of the legs 306 and 308 of the staple 300 together, the staple is locked into the tissue 64. Any tendency for the resilient legs 306 and 308 to spring back to their original positions (FIG. 21) is prevented by the interconnected the end portions 302 and 304 of the legs.

When the upper and lower layers 116 and 118 of the body tissue 64 are to be interconnected, the long thin member 202 (FIGS. 9-12) is inserted through the layers 116 and 118 of body tissue. The leading end portion 204 of the long thin member 202 is then expanded. The gripper member 232 (FIG. 12) may then be moved along the long thin member 202 to clamp the layers 116 and 118 of body tissue as illustrated in FIG. 12. It is preferable to clamp the layers 116 and 118 of body tissue, but use of the gripper member may be eliminated. If desired, use of the entire tissue positioning assembly 200 could be eliminated.

Figure 21:
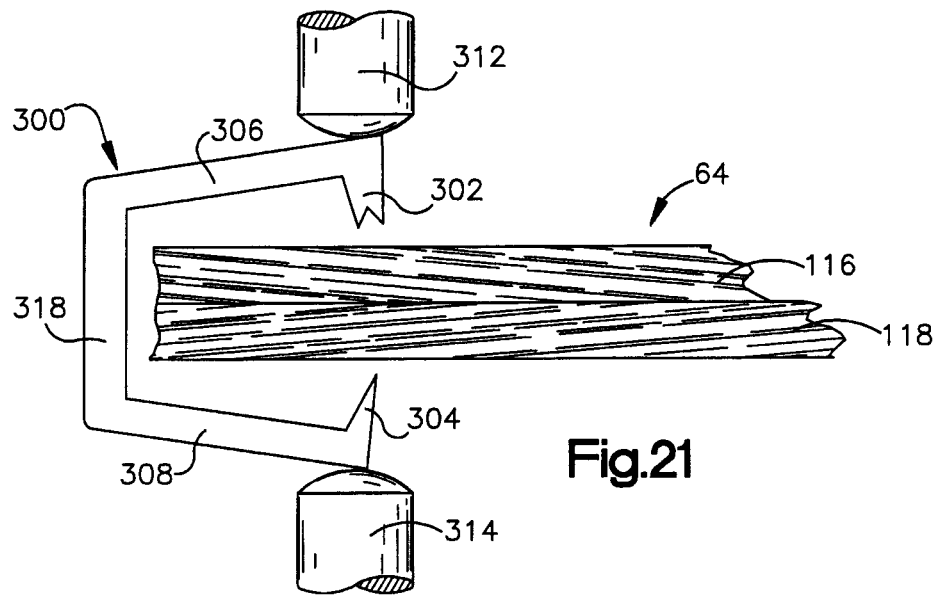
FIG. 21 is a schematic illustration depicting the manner in which a staple is positioned relative to body tissue by the robotic mechanism of FIG. 1.

Once the layers 116 and 118 of body tissue 64 have been gripped as illustrated schematically in FIG. 12, the two layers 116 and 118 of body tissue are moved to a desired position in the patient's body and are held there by the tissue positioning assembly 200. The robotic mechanism 38 is then operated to move the staple 300 to a desired position relative to the body tissue 64 (FIG. 21). At this time, the legs 306 and 308 of the staple 300 are in their initial or relaxed condition illustrated in FIG. 21. The end portions 302 and 304 of the staple legs are spaced apart. This enables the staple 300 to be moved by the robotic mechanism 38 to a position in which body tissue 64 is disposed between the end portions 302 and 304 of the staple legs 306 and 308 (FIG. 21).

Force transmitting members 312 and 314 (FIG. 21) are then moved by the robotic mechanism 38 to deflect the staple legs 306 and 308. The staple legs 306 and 308 are deflected from their initial or unrestrained positioned illustrated in FIG. 21 to a bent or deflected position, illustrated in FIG. 22. As the staple legs 306 and 308 are bent under the influence of force applied against the legs by the force transmitting members 312 and 314, the end portions 302 and 304 of the legs move into engagement (FIG. 22) in the body tissue 64. Although the force transmitting members 312 and 314 are moved by the robotic mechanism 38, it is contemplated that the force transmitting members 312 and 314 could be moved manually if desired.

While the end portions 302 and 304 of the staple legs 306 and 308 are pressed together, ultrasonic vibratory energy is transmitted to the staple 300 to effect the heating of the end portions 302 and 304 of the staple legs 306 and 308 and a bonding of the staple legs together. To this end, ultrasonic vibratory energy is transmitted from the force transmitting member 312 to the staple legs 306 and 308. This results in the force transmitting member 312 functioning as a horn for ultrasonic vibratory energy. The force transmitting member 314 functions as an anvil.

The apparatus for transmitting ultrasonic vibratory energy to the staple legs 306 and 308 may have a construction and mode of operation which is similar to the construction and mode of operation of the apparatus disclosed in U.S. Pat. Nos. 5,836,897 and 5,906,625 and in U.S. patent application Ser. No. 09/524,397. However, it should be understood that the staple legs 306 and 308 could be heated with devices other than sources of ultrasonic vibratory energy. For example, a laser and/or resistance wire could be used to heat the staple legs 306 and 308.

The staple 300 is formed of a biodegradable polymeric material. However, staple 300 may be formed of any one of many different type of materials, including polymers of lactic acid, lactides, l-lactides, and isomers of lactic acids and/or lactides. Although it is believed that it may be desired to form the staple 300 of polycaperlactone, other known biodegradable or non-biodegradable polymers may be utilized to form the staple 300.

To effect a bonding of the end portions 302 and 304 of the staple legs 306 and 308 together, the material of the end portions of the staple legs is heated to a temperature in its transition temperature range by the application of ultrasonic vibratory energy to the end portions 302 and 304 of the staple legs 306 and 308. This results in the polymeric material of the end portions 302 and 304 of the staple legs 306 and 308 changing from a rigid solid condition in which it has a fixed form to a soft or viscous condition. The material of the staple legs 306 and 308 adjacent to the end portions 302 and 304 is not heated into its transition temperature range and maintains its original configuration.

Figure 22:
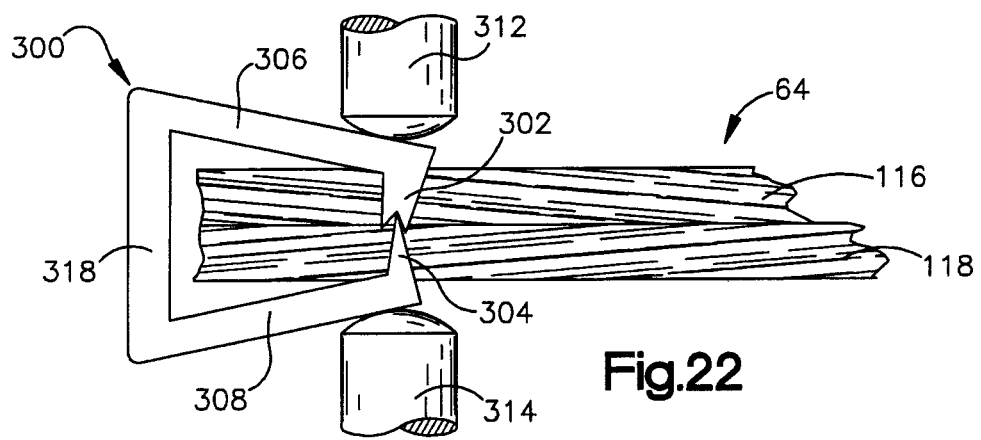
FIG. 22 is a schematic illustration depicting the manner in which the staple of FIG. 21 is bent and end portions of the staple are bonded together by the robotic mechanism of FIG. 1.

After the material the end portions 302 and 304 of the staple leg 306 and 308 has been heated into the transition temperature range and has a soft moldable condition, the material moves under the influence of the force applied against the staple legs 306 and 308 by the force transmitting members 312 and 314. The heated material of the staple legs 306 and 308 molds itself together and blends at the end portions 302 and 304 of the suture legs 306 and 308. The staple leg end portions 302 and 304 are cooled to a temperature below the transition temperature range of the material of the staple 300 and a secure bond is obtained between the polymeric material of the end portion 302 and the end portion 304 of the staple legs. This secure bond prevents a springing back of the resilient staple legs 306 and 308 toward their initial positions (FIG. 21) relative to each other. Therefore, a portion of the body tissue 64 is gripped between the end portions 302 and 304 of the staple legs 306 and 308 and a connector or bight portion 318 of the staple 300 (FIG. 22). The grip obtained by the staple 300 on the body tissue 64 holds the layers 116 and 118 in secure engagement with each other.

Although only a single staple 300 has been illustrated in FIG. 21 a linear array of staples is provided along the ends of the side-by-side layers 116 and 118 of body tissue 64. This results in linear apposition of the layers 116 and 118 of body tissue 64. The two layers 116 and 118 are interconnected in a side-by-side relationship by a plurality of staples in much the same manner as in which the layers 116 and 118 of body tissue are interconnected in FIG. 5.

One or more of the staples 300 and/or the anchors 60, sutures 66 and retainers 72 may be used for purposes other than the interconnecting of layers 116 and 118 of body tissue. They may be used in association with the repair of cartilage, pancreas, kidney, a stomach, a colon, etc. They may also be utilized in open or endoscopic surgery and may be applied by a robotic mechanism, similar to the robotic mechanism 38, or may be manually applied. Additionally, they may be utilized for many different purposes, including rotator cuff repair, meniscus repair, the attachment of soft tissue, such as a ligament or tendon to bone, interconnection of various soft tissues to each other, and interconnections of portions of bone, or with many different types of surgical implants, such as a prosthesis in a patient's body.

In the embodiment of FIGS. 21 and 22, the staple 300 forms a loop which extends around a portion of the body tissue disposed between the end portions 302 and 304 of the staple legs 306 and 308 and the connector or bight portion 318 of the staple (FIG. 22). However, it is contemplated that the staple 300 may be embedded in body tissue at a location spaced from edge portions of the body tissue. For example, the staple may be utilized to connect a layer of body tissue or other material with a relatively large portion of body tissue which forms an organ or gland or muscle in a patient's body, such as a pancreas or kidney. The staple 300 (FIGS. 21 and 22) and/or suture connections of FIGS. 5, 6 and 8 may be utilized in association with components of a patient's body cardiovascular system including the heart and/or blood vessels.

The tissue positioning assembly 200 of FIGS. 9-19 may be utilized to position body tissue at any location where a staple 300 or suture connection of FIG. 5 is utilized. It should be understood that the components of the tissue positioning assembly 200 will vary depending upon the location where the staple or suture connection is to be positioned. Thus, the tissue positioning assembly 200 may include only the long thin member 202. Alternatively, the tissue positioning assembly 200 may include both the long thin member 202 and the gripper member 232 (FIG. 12). The leading end portion 204 of the long thin member 202 may be expanded at a location where expansion of the end portion 204 deflects body tissue. Alternatively, the leading end portion 204 of the long thin member 202 may be expanded at a location where the expansion does not deflect body tissue (FIG. 10). It is believed that the tissue positioning assembly 200 will be particularly advantageous in holding body tissue during the application of a staple 300 or a suture connection. However, the tissue positioning assembly 200 may be used during many other surgical procedures on many different types of body tissue.

Staple-Bonded
Leg Sides

Figure 25:
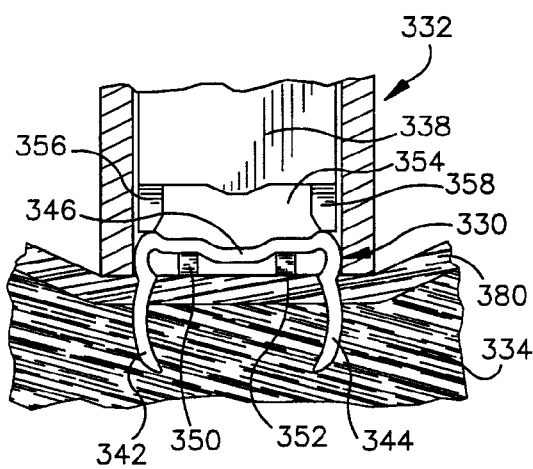
FIG. 25 is a schematic illustration depicting the manner in which the staple of FIG. 24 is inserted into body tissue by operation of the stapling mechanism by the robotic mechanism of FIG. 1.
Figure 26:
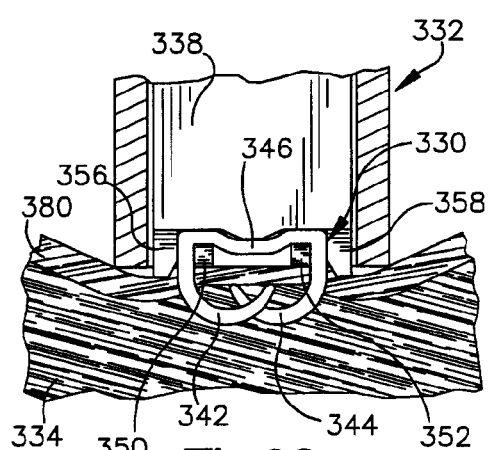
FIG. 26 is a schematic illustration depicting the manner in which the staple of FIG. 25 is bent and legs of the staple are bonded together by operation of the robotic mechanism of FIG. 1.

The sides of legs of a staple 330 (FIGS. 23-26) are bonded together to hold the staple in the closed condition of FIG. 26. The staple 330 is formed of a polymeric material which may be either biodegradable or nonbiodegradable.

Figure 23:
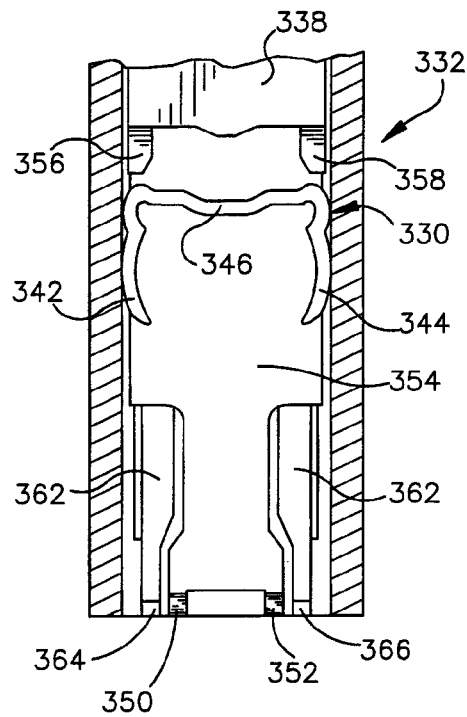
FIG. 23 is a schematic illustration depicting the relationship of a staple to a portion of a stapling mechanism prior to insertion of the staple into body tissue during operation of the robotic mechanism of FIG. 1.
Figure 24:
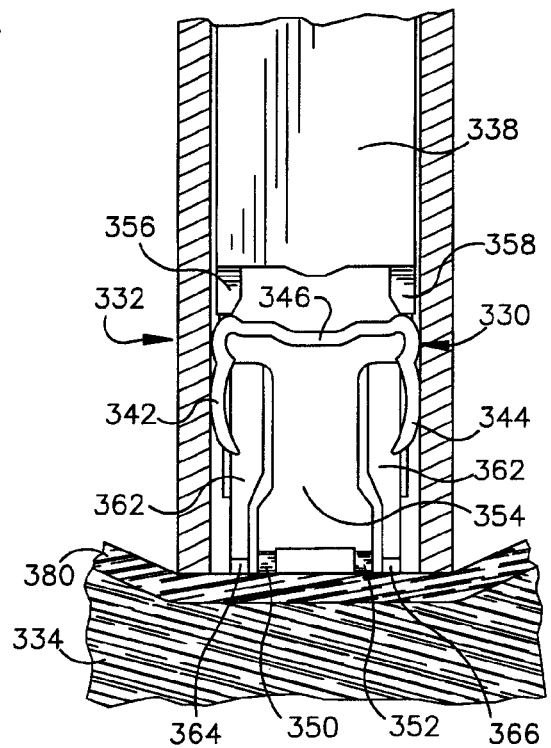
FIG. 24 is a schematic illustration, depicting the manner in which the stapling mechanism of FIG. 23 is pressed against body tissue with a predetermined force by the robotic mechanism of FIG. 1 prior to insertion of a staple.

When the staple 330 (FIG. 23) is to be embedded into body tissue, the robotic mechanism 38 moves a staple mechanism 332 to a desired position relative to body tissue 334 (FIG. 24). The robotic mechanism 38 urges the staple mechanism toward the body tissue 334 with a predetermined force. When the staple mechanism 300 has been moved to the desired position relative to the body tissue 334, a pusher plate 338 is advanced or lowered from the position show in FIG. 23 through the position show in FIG. 24 to the position shown in FIG. 25. As the pusher plate 338 is lowered or advanced to the position shown in FIG. 25, legs 342 and 344 of the staple 330 are moved from a position spaced from the body tissue 334 (FIG. 24) to a position in which the legs extend into the body tissue (FIG. 25).

The staple 330 enters the body tissue 334, a connector or bight portion 346 of the staple 330 moves into engagement with a pair of anvils 350 and 352 (FIGS. 23-25). The anvils 350 and 352 are integrally formed with an anvil plate 354 (FIG. 23) disposed in the stapling mechanism 332. At this time, the legs 342 and 344 of the staple 330 extend into the body tissue 334 (FIG. 25). However, the legs 342 and 344 extend in a generally perpendicular relationship with the connector or bight portion 346 of the staple 330 and do not engage each other. Although there is some gripping action between the legs 342 and 344 of the staple 330 and the body tissue 334 at this time (FIG. 25), the staple 330 is not secured in the body tissue.

Continued downward movement of the pusher plate 338 causes force transmitting members or lands 356 and 358 connected to the pusher plate 338 to press against the connector or bight portion 346 of the staple 330 (FIG. 25). As the pusher plate 338 continues to be advanced or lowered to the position shown in FIG. 26, the lands or force transmitting members 356 and 358 deflect or bend the legs 342 and 344 to the gripping position illustrated in FIG. 26, to dispose a portion of the body tissue 334 between the legs 342 and 344 and the connector or bight portion 346 of the staple 330 (FIG. 26).

Longitudinally extending side surfaces of the staple legs 342 and 344 are disposed in engagement with each other when the staple 330 is in the bent or deflected condition of FIG. 26. The longitudinally extending side surfaces on the staple legs 342 and 344 engage at a location where the staple legs cross beneath (as viewed in FIG. 26) the connector or bight portion 346 of the staple.

Once the staple 330 has been bent or deformed to grip the body tissue 334 in the manner illustrated schematically in FIG. 26, the legs 342 and 344 of the staple are bonded together. The location where the end portions of the legs 342 and 344 cross and engage each other. To effect a bonding of the legs 342 and 344 to each other, the polymeric material of the staple 330 is heated into its transition temperature range at the location where the end portions of the legs 342 and 344 of the staple legs are disposed in engagement.

To effect a heating of the legs 342 and 344 of the staple, ultrasonic vibratory energy is transmitted from the land or force transmitting member 356 to the staple 330. As this is done, the land or force transmitting member 356 functions as a horn for ultrasonic vibratory energy. The opposite land or force transmitting member 358 functions as an anvil of the ultrasonic vibratory energy application system. The ultrasonic vibratory energy application system may have a construction similar to the construction disclosed in the aforementioned U.S. Pat. Nos. 5,836,897 and 5,906,625 or in U.S. patent application Ser. No. 09/524,397. It should be understood that other known devices could be used to heat the staple 330. Thus, an electrical resistance wire heater or a laser could be used to heat the staple 330.

The staple 330 is formed of a polymeric material. The ultrasonic vibratory energy transmitted to the staple 330 from the force transmitting member 356 is effective to heat the polymeric material of the staple legs 342 and 344 into a transition temperature range for the material. When the material of the staple legs 342 and 344 is cooled, a bond is formed between the staple legs in the same manner as previously explained in conjunction with the staple 300 of FIGS. 21 and 22.

Once the legs 342 and 344 of the staple have been bonded together, the staple is released or disengaged from the anvils 350 and 352 by an injector spring 362 having legs 364 and 366 (FIG. 23) which are pressed against the staple 330. This force separates the staple from the anvils 350 and 352.

It is contemplated that the staple mechanism 332 may have any one of many known constructions. It is also contemplated that the staple 330 could have a configuration other than the configuration illustrated in FIGS. 23-26. For example, the staple 330 could have a construction somewhat similar to the construction of the staple 300 of FIG. 21.

The stapling mechanism 332 has a general construction and mode of operation which is similar is to the construction and mode of operation of a known stapling mechanism disclosed in U.S. Pat. No. 5,289,963. However, this known stapling mechanism does not bond the legs of a staple together. By bonding the legs 342 and 344 of the staple 330 together, a resilient springing back of the legs toward their initial positions and a resulting release of the body tissue 334 is prevented.

The staple 330 (FIGS. 23-26) is advantageously formed of a biodegradable polymeric material, such as polycaperlatone. Staple 330 may also be formed of any one of many known biodegradable materials, including polymers or co-polymers of lactic acid, lactides, l-lactides, and isomers of lactic acids and/or lactides. Of course, the staple 330 may be formed of many different known biodegradable materials. If desired, the staple 330 may be formed of a material which is not biodegradable.

The staple 330 will be utilized for tissue repair within a patient's body and in the locations on the surface of the patient's body. Regardless of whether the stapling mechanism 332 is used to staple outside of a patient's body or within the patient's body, the stapling mechanism may advantageously be utilized as part of the robotic mechanism 38 of FIG. 1. However, it should be understood that the stapling mechanism 332 could be manually actuated rather than be robotically actuated if desired.

The stapling mechanism 332 is illustrated in FIGS. 24-26 as connecting a flexible surgical mesh 380 with the body tissue 334. The robotic mechanism 38 may be used to position the surgical mesh 380 in the patient's body. Movement of the surgical mesh 380 through the limited incision 52 by the robotic mechanism 38 may be facilitated by moving the mesh into the patient's body in a rolled up condition. The robotic mechanism 38 would then be operated to unroll the surgical mesh 380 in the patient's body and position the surgical mesh relative to the body tissue 334.

Although only a single staple 330 is illustrated in FIGS. 24-26, a plurality of staples 330 are utilized to connect the surgical mesh 380 with the body tissue 334. In addition to staples 330, suture anchors 60, sutures 66 and retainers 72 (FIG. 5) may be utilized to connect the surgical mesh 380 with the body tissue 334 in the manner previously described in conjunction with FIGS. 2-4. Both staples and suture connections may be utilized to connect the mesh 380 with the body tissue 334. Alternatively, only staples or only suture connections may be used to connect the surgical mesh 380 with the body tissue 334.

Implant of Viable Tissue Components

Figure 27:
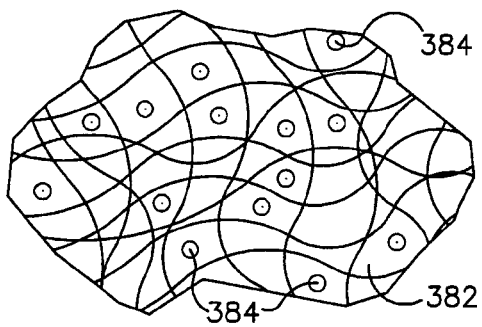
FIG. 27 is a schematic illustration depicting the relationship of viable tissue components to a scaffold or matrix.
Figure 28:
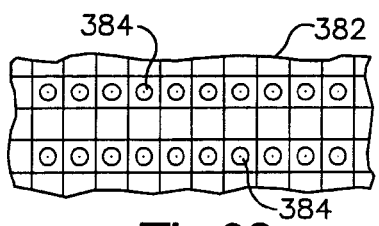
FIG. 28 is a schematic illustration, generally similar to FIG. 27, depicting the relationship of viable tissue components to a different scaffold or matrix.
Figure 29:
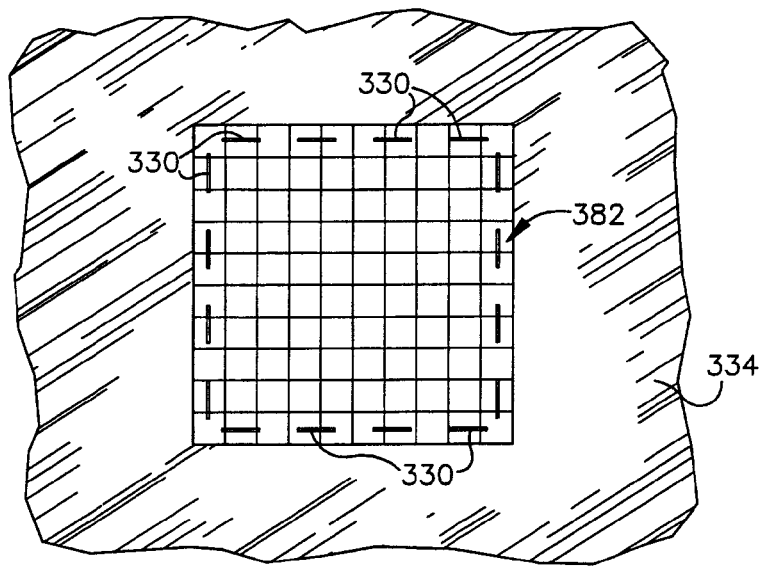
FIG. 29 is a schematic illustration depicting the manner in which the scaffold and viable tissue components of either

Rather than using the staple 330 to connect the surgical mesh 380 with the body tissue 334, the staple 330 may be used to connect a scaffold or framework 382 (FIGS. 27-29) with the body tissue 334. The scaffold 382 provides a non-living three dimensional matrix or supporting framework on which viable body tissue components 384 (FIGS. 27 and 28) are disposed. The three dimensional framework or scaffold 382 may be formed of either biodegradable or a non-biodegradable material.

When the scaffold or framework 382 is formed of a non-biodegradable material, body tissue will grow through the scaffold or framework so that the scaffold becomes embedded in new tissue growth. When the scaffold or framework 382 is formed of a biodegradable material, the scaffold will eventually degrade and be absorbed by body tissue. The scaffold 382 may have fibers of biodegradable material randomly arranged in the manner illustrated schematically in FIG. 27 to form a supporting framework. Alternatively, the scaffold or framework 382 may have biodegradable fibers arranged in an ordered relationship similar to the relationship illustrated schematically in FIG. 28.

It is contemplated that the scaffold or framework 382 may have either a flexible or rigid construction. The scaffold 382 could be formed of a biodegradable material such as polyglycolic acid or polylactic acid. If desired, the scaffold or framework 382 could be formed of fibrous connective materials such as portions of body tissue obtained from human and/or animal sources. The scaffold or framework 382 may be formed of collagen or submucosal tissue.

The scaffold or matrix 382 forms a supporting framework for tissue inductive factors and viable tissue components 384. The viable tissue components 384 may be mesenchymal cells which are introduced into the scaffold or framework in the operating room. Thus, the matrix or scaffold 382 may be constructed at a location remote from an operating room. After the scaffold 382 has been transported to the operating room, the viable tissue components 384, such as mesenchymal cells, may be introduced into the scaffold.

It is contemplated that the matrix or scaffold 382 may contain viable tissue components 384 which include stem cells and/or fetal cells. The stem cells and/or fetal cells may be introduced into the matrix or scaffold 382 in the operating room. It is contemplated that tissue growth inductive factors may be provided in the matrix or scaffold 382 along with any desired type of precursor cells. The scaffold or matrix 382 may also contain viable tissue components 384 which are viable platelets centrifuged from blood in a manner similar to that described in U.S. patent application Ser. No. 09/483,676, filed Jan. 14, 2000 and U.S. Pat. No. 6,174,313. The viable tissue components 384 may be fragments harvested from a patient in the manner disclosed in the aforementioned U.S. Pat. No. 6,174,313.

The scaffold or matrix 382 may have a layered construction with each of the layers being formed at different materials. Each of the layers of the scaffold or matrix may be impregnated with a different material and/or contain different viable tissue components 384. For example, precursor cells may be provided in one layer of the scaffold or matrix 382 and tissue growth inductive factors and/or antibiotics may be provided in another layer of the scaffold or matrix. The scaffold or matrix 382 may be formed of body tissue such as allograft or autograft. The viable tissue components 384 in the scaffold or matrix 382 may be obtained from the patient or from another human being. Alternatively, the viable tissue components 384 may be obtained from an animal.

The scaffold 382 and viable tissue components 384 may be utilized to create organ or gland structure or tissue, such as structural tissue of a pancreas, liver, or kidney. The scaffold or matrix 382 and viable tissue components 384 may be used in the repair of components of a patient's cardiovascular system including the heart and/or blood vessels. It should be understood that a plurality of different types of viable cells may be provided on a single three dimensional matrix or scaffold 382.

The scaffold 382 and viable tissue components 384 may advantageously be positioned in the patient's body by the robotic mechanism 38. When the scaffold 382 and viable tissue components 384 are to be positioned in the patient's body by the robotic mechanism 38, the scaffold and viable tissue components are moved through the limited incision 52 (FIG. 1) by the robotic mechanism 38. When the scaffold or matrix 382 has a rigid structure, the scaffold may be formed as a plurality of separate sections. The rigid sections of the scaffold 382 are sequentially moved through the limited incision 52 and secured to tissue in the patient's body with suitable fasteners, such as the staple 330 and/or suture 66, anchor 60 and retainer 72 fasteners of FIG. 5, by the robotic mechanism 38. The sections of the scaffold 382 may be secured in any desired manner, including the manner illustrated in FIGS. 2-4 or FIGS. 23-26 herein.

When the scaffold or matrix 382 (FIGS. 27-29) has a flexible structure, the scaffold may be rolled up outside the patient's body to form a cylinder. The rolled up scaffold 382, with the viable tissue components 384 thereon, is moved through the limited incision 52 (FIG. 1) into the patient's body by operation of the robotic mechanism 38. Once the rolled up scaffold 382 and viable tissue components 384 (FIGS. 27-29) have been moved into the patient's body by the robotic mechanism 38, the robotic mechanism unrolls the flexible scaffold 382 with the viable tissue components 384 on the scaffold. The robotic mechanism 38 is then operated to position the unrolled scaffold 382 and viable tissue components 384 relative to tissue in the patient's body. The unrolled scaffold 382 is connected with the patient's body tissue with suitable fasteners, such as the staples 330 and/or suture, anchor and retainer fasteners of FIG. 5, by the robotic mechanism 38. The scaffold 382 may be secured in any desired manner, including the manner illustrated in FIGS. 2-4 or FIGS. 23-26 herein. While the robotic mechanism 38 may position and secure the scaffold 382 with the viable tissue components 384 on the scaffold, this may also be done manually.

Figure 30:
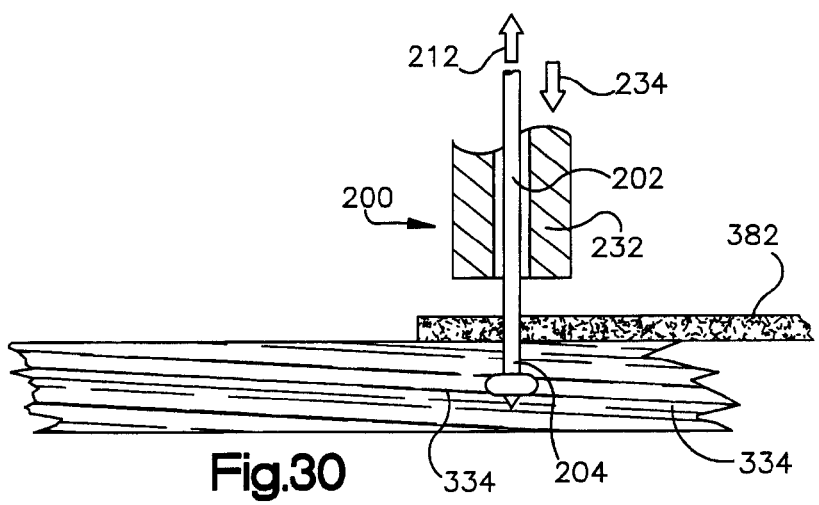
FIG. 30 is a schematic illustration depicting the manner in which the positioning assembly of FIGS. 9 and 10 is utilized to position the scaffold of FIG. 27 or 28 relative to body tissue during operation of the robotic mechanism of FIG. 1.

The tissue positioning assembly 200 (FIG. 30) may be used to position the scaffold 382 and viable tissue components 384 relative to the body tissue 334. When this is to be done, the long thin member 202 is moved through the scaffold 382 into the body tissue 334 with the leading end portion 204 of the long thin member in the contracted condition of FIG. 9. The leading end portion 204 is then expanded in the body tissue 334 (FIG. 30). Alternatively, the leading end portion 204 may be moved through the body tissue and then expanded, in the manner illustrated in FIGS. 10, 11, and 12.

A gripper member 232 (FIG. 30) may be moved along the long thin member 202. The gripper member 232 is pressed against the scaffold 382, in the manner indicated by the arrow 234. This results in the scaffold 382 being pressed against the body tissue 334. The scaffold 382 and a portion of the body tissue 334 are clamped between the gripper member 232 and expanded end portion 204 of the long thin member 202.

The long thin member 202 (FIG. 30) and gripper member 232 are used to grip the scaffold 382 and body tissue 334 and to move them to any desired position in the patient's body. In addition, the gripper member 232 and long thin member 202 hold the scaffold 382 and body tissue 334 in a desired relationship to each other and to other tissue in the patient's body during securing of the scaffold to the body tissue with the staple 330 and/or other fasteners. If desired, a retainer 72 may be secured to the long thin member, in the manner illustrated in FIG. 19. This would enable the long thin member 202 (FIG. 30) to be used as a portion of a fastener interconnecting the scaffold 382 and body tissue 334.

The viable tissue components 384 may be positioned in the patient's body in ways other than using the scaffold or matrix 382. Thus, body tissue components, including viable body tissue components 384, may be harvested from a human or animal body in the manner disclosed in the aforementioned U.S. Pat. No. 6,174,313. The tissue components may then be shaped to form a body having a desired configuration. The tissue components may be shaped using a press in the manner disclosed in U.S. Pat. No. 6,132,472. Alternatively, the tissue components may be shaped to a desired configuration by a molding process. The molding process may be performed using a press similar to any one of the presses disclosed in U.S. Pat. No. 6,132,472. Alternatively, the molding process may be performed using an open mold. The resulting shaped body of tissue components, including viable tissue components, may be secured in a patient's body using the robotic mechanism 38 and one or more of the fasteners disclosed herein.

Tissue Retractors

Figure 31:
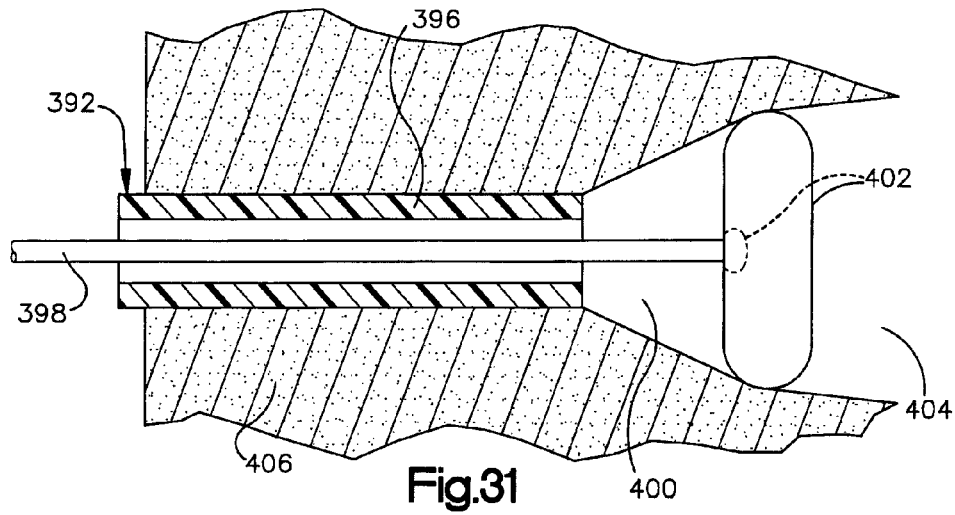
FIG. 31 is a schematic illustration depicting the manner in which an expandable retractor assembly is positioned by the robotic mechanism of FIG. 1 to separate body tissue.

The robotic mechanism 38 (FIG. 1) may be used to position a tissue retractor assembly 392 (FIG. 31) relative to body tissue. The robotic mechanism effects operation of the tissue retractor assembly 392 from a contracted condition to an expanded condition to move body tissue. This movement of body tissue may advantageously create a space for the performance of a surgical procedure by the robotic mechanism 38. Thus, space could be created for the positioning of a suture connection of the type illustrated in FIG. 5 and/or for a staple connection of the type illustrated in FIGS. 22 and 26. Of course, other surgical procedures could be conducted in the space created by expansion of the tissue retractor assembly 392.

The tissue retractor assembly 392 (FIG. 31) includes a tubular, cylindrical cannula or scope 396. A tubular, cylindrical shaft 398 is disposed in a coaxial relationship with the cannula or scope 396 and extends axially through the cannula or scope. However, if desired, the shaft 398 may be offset to one side of the cannula or scope 396. This would facilitate the insertion of one or more surgical instruments through the cannula 396 to a working space 400 created by expansion of a balloon or bladder 402 from the contracted condition shown in dash lines in FIG. 31 to the expanded condition in solid lines in FIG. 31.

As the bladder or balloon expands, portions of body tissue 406 are deflected under the influence of force applied to the body tissue by the bladder or balloon 402. If desired, the bladder or balloon 402 may have a toroidal configuration with a central passage so that surgical instruments may be inserted through the balloon to a working space 404 offset to the right (as viewed in FIG. 31) of the balloon. Expansion of the balloon 402 may be utilized to conduct a surgical procedure, such as dissection.

The tubular shaft 398 has a central passage through which fluid, such as a liquid or gas, may be conducted to the bladder or balloon 402 to effect expansion of the bladder or balloon from the contracted condition to the expanded condition. The shaft 398 and cannula or scope 396 are connected with the robotic mechanism 38 (FIG. 1) to enable the robotic mechanism to position the tissue retractor assembly 392 relative to the body tissue 406 and to enable the robotic mechanism to control the flow of fluid to the bladder or balloon 402 to thereby control the extent of expansion of the bladder or balloon.

It is contemplated that the tissue retractor assembly 392 may have a construction which is different than the construction illustrated in FIG. 26. Thus, the tissue retractor assembly 392 may have any one of the constructions disclosed in U.S. Pat. Nos. 6,042,596 and 6,277,136. The robotic mechanism may be utilized to effect operation of a selected tissue retractor assembly in the same manner as is disclosed in the aforementioned U.S. Pat. Nos. 6,042,596 and 6,277,136.

If the tissue retractor assembly is to effect separation of body tissues along naturally occurring planes, the robotic mechanism 38 may be operated to move the tissue retractor assembly 392 to the desired position in a patient's body where the balloon or bladder 402 is filled with fluid to effect expansion of the bladder or balloon to the condition illustrated in solid lines in FIG. 26. The bladder or balloon is then contracted, by exhausting fluid from the bladder or balloon 402 through the shaft 398. The robotic mechanism 38 may be then operated to advance either just the contracted bladder or balloon 402 relative to the body tissue 406 or to advance the entire tissue retractor assembly 392 relative to the body tissue. Once the bladder or balloon 402 has been advanced, with or without the cannula scope 396, by operation of the robotic mechanism 38, the bladder or balloon 402 is again expanded. This sequential contraction, advancement, and expansion of the bladder or balloon may be repeated any desire number of times to effect the desired separation of portions of the body tissue 406.

It is contemplated that the balloon or bladder 402 may be left in a patient's body. When this is to be done, the balloon or bladder 402 may be formed of a biodegradable material. Of course, components of the retractor assembly 392 other than the balloon bladder 402 may be formed of biodegradable material.

Figure 32:
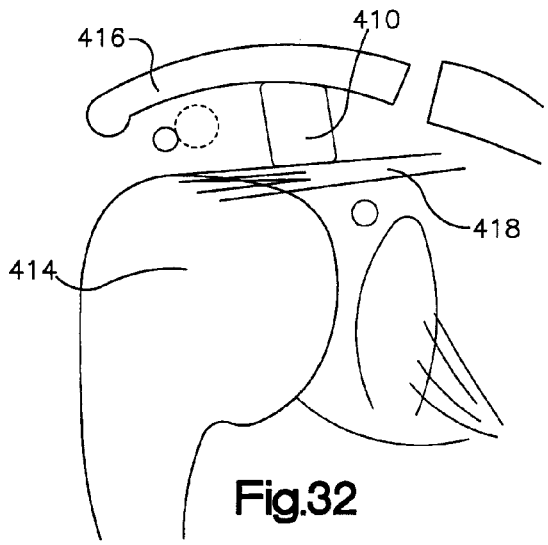
FIG. 32 is a schematic illustration depicting the manner in which an expandable retractor assembly is positioned relative to a shoulder joint by the robotic mechanism of FIG. 1.

A tissue retractor assembly may be utilized to separate bones at a joint. In FIG. 32, a tissue retractor assembly 410 is positioned in a shoulder joint 412. Specifically, the robotic mechanism 38 is operated to position the tissue retractor assembly 410 relative to a humeral head 414, achromium 416 and rotator cuff 418 in the shoulder joint 412.

Once the tissue retractor assembly 410 has been positioned at a desired location in the shoulder joint 412, the robotic mechanism 38 effects expansion of a balloon or bladder in the tissue retractor assembly 410 from a contracted condition to an expanded condition. This effects movement of the achromium 416 relative to the rotator cuff 418. This increases the space in the shoulder joint for the surgeon to work on the body tissue. The manner in which the tissue retractor assembly 410 is used in the shoulder joint 412 is similar to the manner disclosed in the aforementioned in U.S. Pat. No. 6,277,136.

In FIG. 32, the tissue retractor assembly 410 is utilized to create space within a shoulder joint 412. However, it is contemplated that the robotic mechanism 38 may be utilized to position a contracted tissue retractor assembly relative to other joints in a patient's body and to effect expansion of the tissue retractor assembly to create space in these joints. For example, the tissue retractor assembly may be utilized in association with a knee joint in a leg of a patient or with vertebrae in a patient's spinal column.

When a tissue retractor assembly is to be utilized to create space in a joint in a patient's spinal column, the contracted tissue retractor assembly may be inserted between adjacent vertebrae. A balloon or bladder in the tissue retractor assembly is then expanded under the influence of fluid pressure to increase the space between the vertebrae. Depending upon the construction of the tissue retractor assembly and the position where it is located in the patient's spinal column by the robotic mechanism 38, the expansion of the tissue retractor assembly can separate adjacent vertebrae without significantly changing the spacial orientation of vertebrae relative to each other. Alternatively, the tissue retractor assembly may be positioned by the robotic mechanism 38 at a location where expansion of the tissue retractor assembly results in a tilting or pivoting movement of one vertebra relative to an adjacent vertebra. The tissue retractor assembly may have any one of the constructions disclosed in the aforementioned U.S. Pat. Nos. 6,042,596 and 6,277,136.

A tissue retractor assembly 422 (FIG. 33) is moved through an opening formed in a vertebrae 424 in a patient's spinal column. The robotic mechanism 38 may be utilized to form the opening in the vertebrae 424 and to move the contracted tissue retractor assembly 422 into the vertebra.

Figure 33:
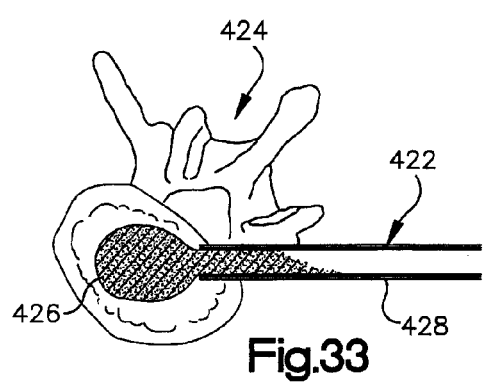
FIG. 33 is a schematic illustration depicting the manner in which an expandable retractor assembly is positioned relative to a vertebra by the robotic mechanism of FIG. 1.

Once the robotic mechanism 38 has been operated to position the tissue retractor assembly relative to the vertebra 424, the robotic mechanism effects expansion of a bladder or balloon 426 from a contracted condition to the expanded condition illustrated schematically in FIG. 33. As this occurs, marrow is compressed within the vertebra 424. The tissue retractor assembly 422 includes a cannula or scope 428 which is utilized to position the balloon or bladder 426 relative to the vertebra 424 and to conduct the fluid (gas or liquid) into the balloon or bladder 426 to effect expansion of the balloon or bladder. The balloon or bladder 426 may be formed of a biodegradable material.

The tissue retractor assembly 422 is subsequently contracted from the expanded condition of FIG. 33 and withdrawn from the vertebra 424. When this has been done, flowable synthetic bone material or cement may be conducted through a cannula into the space in the vertebra 424. It is contemplated that the robotic mechanism 38 will be utilized to position the cannula through which the flow of synthetic bone material or cement is conducted into the space created in the vertebra 424 by expansion of the balloon or bladder 426. The manner in which the balloon or bladder 426 may compress the marrow within the vertebra 424 and create a space which is subsequently filled with synthetic bone material or cement is the same as is disclosed in U.S. Pat. No. 4,969,888.

The balloon or bladder 426 may be formed of a biodegradable material and filled with bone growth inductive factors. The bone growth inductive factors may include bone particles and bone morphogenetic protein. Viable tissue components may be provided in the balloon or bladder 426. The balloon or bladder 426 will degrade with the passage of time and enable bone or other tissue to grow in the space created in the vertebra 424. The balloon or bladder 426 may be filled with a patient's body tissue components harvested in the manner disclosed in U.S. Pat. No. 6,174,313.

In FIG. 33, the tissue retractor assembly 422 has been illustrated in conjunction with a vertebra in a patient's body. It is contemplated that the tissue retractor assembly could be utilized in association with other bones in a patient's body. By utilizing the robotic mechanism 422 to position the tissue retractor assemblies 392, 410 and 422 (FIGS. 31-33) relative to a patient's body, the tissue retractor assemblies can be accurately positioned. The robotic mechanism 38 controls the fluid pressure and thus the force conducted to the bladder or balloon in the tissue retractor assemblies 392, 410 and 422. In addition, the use of the robotic mechanism 38 to control the operation of the tissue retractor assemblies 392, 410 and 422 enables the size of an incision through which the tissue retractor assemblies are inserted to be minimized and the size of an incision for surgical instruments to perform the surgical procedure in space created by operation of the tissue retractor assemblies is minimized.

Threaded Fasteners

Figure 34:
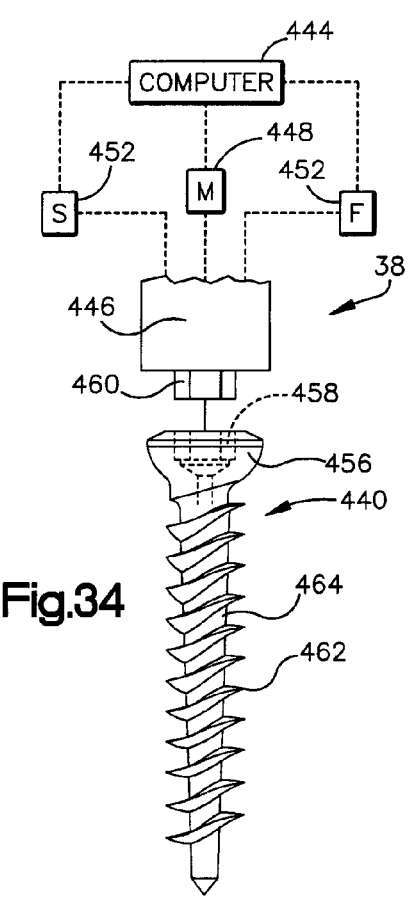
FIG. 34 is a schematic illustration depicting the manner in which the robotic mechanism of FIG. 1 is utilized to position a threaded fastener in body tissue.

The robotic mechanism 38 may also be utilized to secure body tissue with a threaded fastener 440 as illustrated in FIG. 34. Of course, the robotic mechanism 38 may be used with other fasteners if desired. For example, the robotic mechanism 38 could be used in association with fasteners having any one of the constructions disclosed in U.S. Pat. Nos. 5,293,881; 5,720,753; 6,039,753; and 6,203,565.

The robotic mechanism 38 includes a programmable computer 444 (FIG. 34) which is connected with a fastener drive member 446 by a motor 448. In addition to the motor 448, a force measurement assembly 450 is connected with fastener drive member 446 and computer 444. The force measurement assembly 450 has an output to the computer 444 indicating the magnitude of resistance encountered by the fastener drive member 446 to rotation of the fastener 440. A position sensor 452 is connected with fastener drive member 446 and the computer 444. The position sensor 452 has an output which is indicative of the position of the fastener drive member 446. The output from the position sensor 452 indicates the depth or distance to which the threaded fastener is moved into body tissue by operation of the motor 448 to rotate the fastener drive member 446.

The threaded fastener 440 includes a head end portion 456 with a recess 458 which receives a polygonal projection 460 from the fastener drive member 446. Rotation of the fastener drive member 446 by the motor 448 causes the projection 460 to transmit drive torque to the head end portion 456 of the fastener 440.

As the fastener 440 is rotated, a thread convolution 462 on a shank portion 464 engages body tissue. The thread convolution 462 has a spiral configuration. The thread convolution cooperates with the body tissue to pull the threaded fastener into the body tissue as the threaded fastener is rotated.

By utilizing the robotic mechanism 38 to manipulate the fastener 440, the fastener can be accurately positioned relative to body tissue. The output from the force measurement assembly 450 to a computer 444 enables the force, that is resistance to rotation on the threaded fastener 440, to be controlled during rotation of the fastener. This prevents the application of excessive force to the body tissue. In addition, the position sensor 452 enables the distance to which the fastener 440 is moved into the body tissue to be accurately controlled.

Implant

In addition to fasteners to secure tissue in a patient's body, the robotic mechanism 38 may be utilized to position prosthetic implants in a patient's body. During joint replacement surgery and other surgical procedures, prosthetic implants may be placed in a patient's body. The robotic mechanism 38 may be utilized to control movement of a cutting tool during resection of bone in a patient's body.

Figure 35:
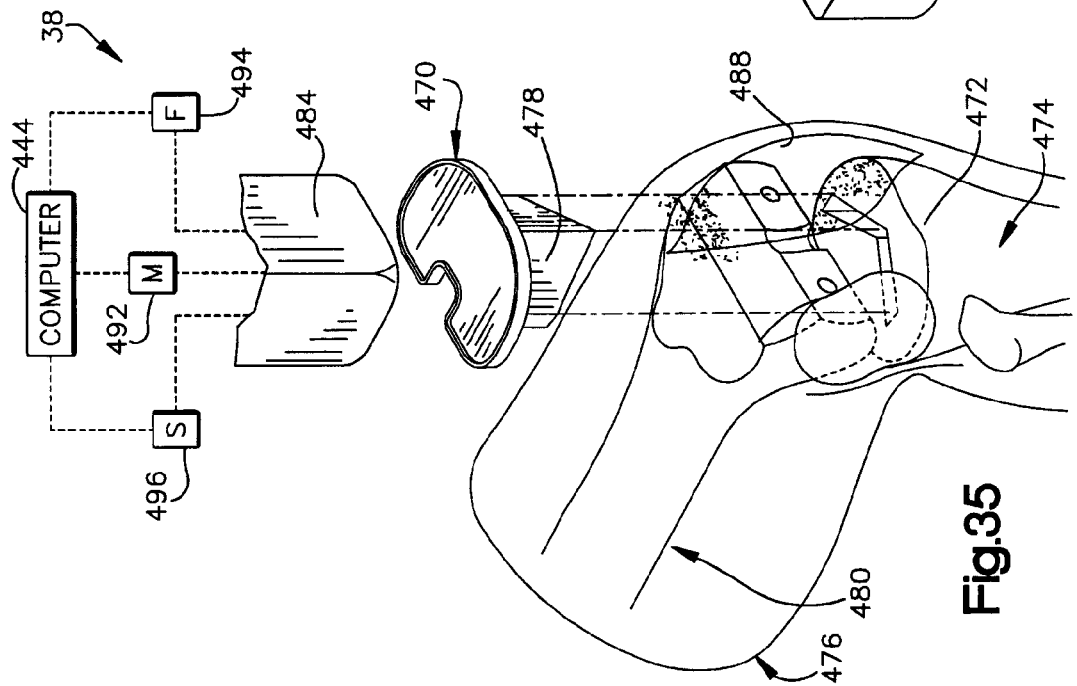
FIG. 35 is a schematic illustration depicting the manner in which the robotic mechanism of FIG. 1 is utilized to position a prosthesis in body tissue.

It is contemplated that the joint replacement surgery may include knee joint replacement. The computer 38 may be utilized to effect a cutting of end portions of a tibia and/or femur in the manner disclosed in U.S. patent application Ser. No. 09/976,396 filed Oct. 11, 2001, by Peter M. Bonutti and entitled Method of Performing Surgery. In addition, the robotic mechanism 38 may be utilized to position a prosthetic implant, such as a tibial tray 470 (FIG. 35) relative to a proximal end portion 472 of a tibia 474 in a leg 476 of a patient. The tibial tray 470 has a keel 478 which is inserted into the proximal end portion 472 of the tibia 474 in the leg 476 of the patient during a knee replacement operation.

During the knee replacement operation, the robotic mechanism 38 effects a resection of both the tibia 474 and femur 480 in the leg 476 of the patient. The robotic mechanism 38 then moves a force transmitting member 484 to move the keel 478 of the tibial tray 470 through a limited incision 488 in the leg 476 of the patient.

The robotic mechanism 38 includes a programmable computer 444 which is connected with the force transmitting member 484 by a motor 492. Operation of the motor 492 is effective to move the force transmitting member and tibial tray 470 relative to the tibia 472 to force the keel 478 of the tibial tray 470 into the tibia 472. A force measurement assembly 494 is connected with the force transmitting member 484 and the computer 444. The output from the force measurement assembly 494 is indicative of a resistance encountered by the force transmitting member 484 in moving the tibial tray 470 into the tibia 474. By monitoring the output from the force measurement assembly 494, the computer 444 can provide an indication to a surgeon of the resistance being encountered to movement of the keel 478 of the tibial tray into the tibia 474 in the patient's leg 476.

A position sensor 496 is connected with the force transmitting member 484 and the computer 444. The position sensor 496 has an output indicative of the position of the force transmitting member 484 relative to the proximal end portion 472 of the tibia 474. This enables a surgeon to monitor the extent movement of the keel 478 on the tibial tray into the proximal end portion 472 of the tibia 474.

The motor 492 has an operating mechanism which effects a pounding of the tibial tray 470 into the proximal end portion 472 of the tibia 474 in much the same manner as in which a hammer has previously been utilized to pound the tibial tray 470 into the 474. However, it is believed that it may be desired to effect the operation of the motor 492 to move the force transmitting member 484 and tibial tray 470 with a continuous insertion stroke without pounding on the tibial tray. This would result in the tibial tray 470 being slowly pressed into the proximal end portion 472 of the tibia 474 with a continuous movement which is monitored by the output from the force measurement assembly 494 and the position sensor 496. By moving the tibial tray 470 with a smooth insertion stroke, accurate insertion of the tibial tray into the tibia 474 is facilitated.

Once the robotic mechanism 38 has been utilized to position the tibial tray 470, a related component of a replacement knee joint may be positioned on the femur 480 by the robotic mechanism. The robotic mechanism 38 may also be utilized to check stability of the knee joint in flexion, extension, and/or rotation. In the manner in which the robotic mechanism is utilized to perform these functions is the same as disclosed in the aforementioned U.S. patent application Ser. No. 09/976,396.

Imaging

It is contemplated that various imaging arrangements may be utilized to enable a surgeon to monitor a surgical procedure, while using the robotic mechanism 38. In the embodiment illustrated in FIG. 1, the single imaging device 40 is utilized to enable imaging of a location where a surgical procedure is being conducted by the robotic mechanism 38 to be transmitted to a monitor 48. Stereoscopic and video stereoscopic viewing of the location where a surgical procedure is being performed by the robotic mechanism 38 may also be desired.

Figure 36:
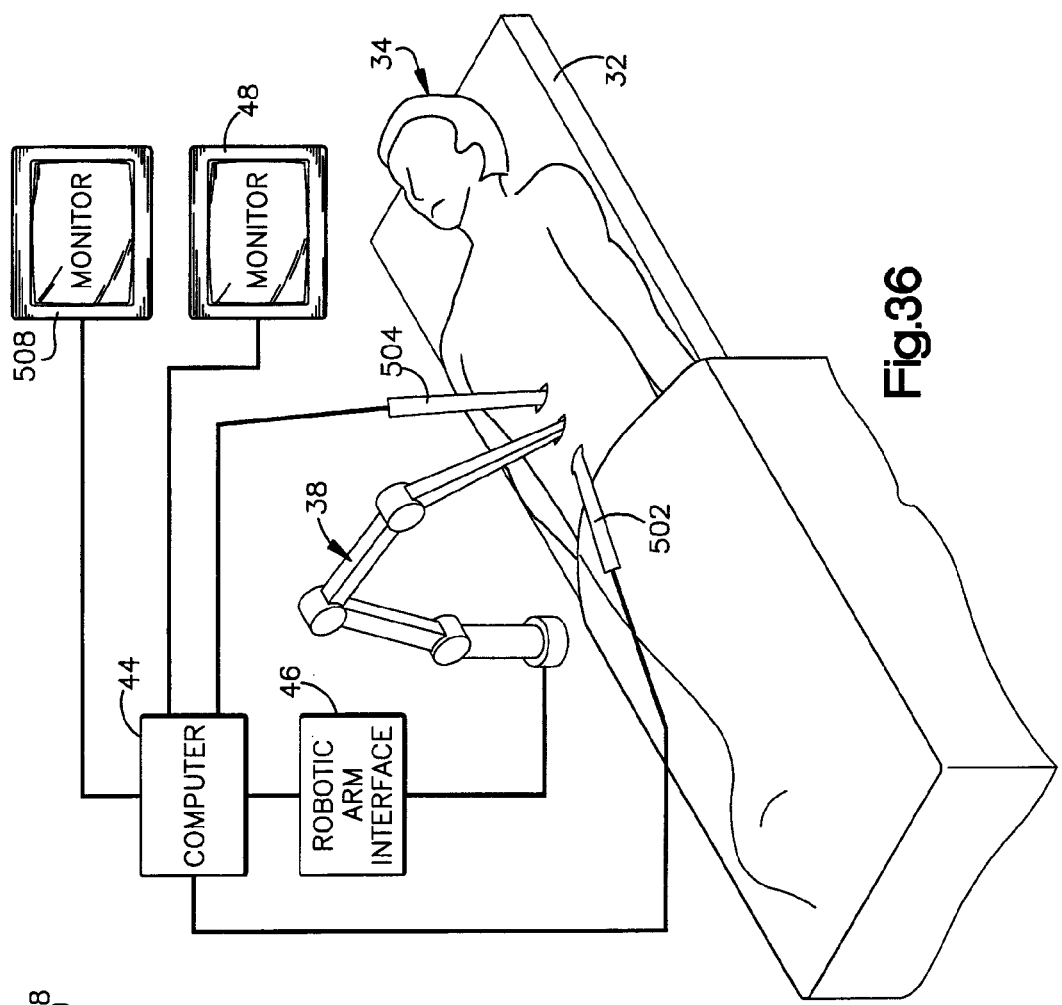
FIG. 36 is a schematic illustration, depicting the manner in which a plurality of imaging devices are used in association with the robotic mechanism of FIG. 1.

A pair of endoscopes 502 and 504 (FIG. 36) may be used in association with the robotic mechanism 38. The endoscopes 502 and 504 are disposed in predetermined angular orientations relative to each other. The output from the endoscopes 502 and 504 is conducted to the computer 44.

The viewing screen of the monitor 48 may be divided into two sections with one section being a monoscopic, that is, two dimensional, image resulting from the output of the endoscope 502. The other section of the screen of the monitor 48 has a monoscopic, that is, two dimensional, image resulting from the output of the endoscope 504. The monitor 508 may be utilized to provide a steroscopic image, that is, a three dimensional image, resulting from the output of both of the endoscopes 502 and 504. The manner in which the stereoscopic images may be obtained from the two endoscopes 502 and 504 at the monitor 508 is similar to that disclosed in U.S. Pat. Nos. 4,651,201 and 5,474,519.

By providing a three dimensional image at the monitor 508, a surgeon has a realistic view of the area where the robotic mechanism 38 is performing a surgical procedure. This enables the surgeon to conduct stereotactic surgery.

A navigation system may also provide inputs to the computer 44 to assist in the control of the robotic mechanism 38 and the performance of the surgical procedure. The navigation system may include transmitters connected with the robotic mechanism 38. Transmitters may also be connected with the endoscope 502 and 504.

If desired, a plurality of navigation members may be connected with tissue in the patient's body by the robotic mechanism 38. Reflective end portions of the navigation members are disposed in the patient's body and are illuminated by light conducted along fiber optic pathways in the endoscopes 502 and 504. Images of the ends of the navigation members are conducted from the endoscopes 502 and 504 to the monitors 48 and 508. The images of the ends of the navigation members enable a surgeon to determine the relative positions of body tissue in the patient's body during performance of a surgical procedure with the robotic mechanism.

Alternatively, the navigation members may extend through the patient's skin into engagement with one or more tissues in a patient's body. Reflective ends of the navigation members would be disposed outside of the patient's body and would be visible to the surgeon. In addition, the reflective ends of the navigation members would be visible to an optical sensing system connected with the computer 44 and robotic mechanism 38. Relative movement between the reflective ends of the navigation members would be sensed by the optical sensing system and would enable the computer 44 to determine the relative positions of tissues in the patient's body. In addition, relative movement between the reflective ends of the navigation members could be visually sensed by the surgeon and would enable the surgeon to determine the relative positions of tissues in the patient's body based on direct observation of the navigation members.

For example, the navigation members could be connected with one or more bones in a patient's body. When the reflective ends of the navigation members are disposed in the patient's body, the endoscope 502 and 504 can be used to determine the location of one or more bones relative to other tissues. When the reflective ends of the navigation members are disposed outside the patient's body, the surgeon and/or an optical sensing system can determine the location of one or more bones relative to other tissues.

Rather than using two endoscopes 502 and 504 to obtain images, an ultrasonic imaging device may be used with only one of the endoscopes. For example, the endoscope 504 could be omitted or merely turned off. A known ultrasonic imaging device may be used to provide images which are transmitted to the computer 44. The ultrasonic imaging device may be constructed and operated in a manner similar to that disclosed in U.S. Pat. Nos. 5,897,495 and 6,059,727. The images which are transmitted to the computer 44 from the ultrasonic imaging device may be used to create monoscopic images at the monitor 48. Alternatively, the images from the ultrasonic imaging device may be combined with images from the endoscope 502 to create stereoscopic images. If desired, the stereoscopic images may be created in the manner disclosed in U.S. Pat. No. 6,059,727.

The images provided by the endoscopes 502 and 504 and/or an ultrasonic imaging device enable the surgeon to monitor the performance of any of the surgical procedures disclosed herein. Additionally, various combinations of the foregoing steps may be included in the surgical procedures. For all surgical procedures, the images provided at the monitors 48 and 508 (FIG. 36) by the endoscopes 502 and 504 and/or the ultrasonic imaging device will facilitate performance of the surgical procedure in the patient's body with the robotic mechanism 38.

Figure 37:
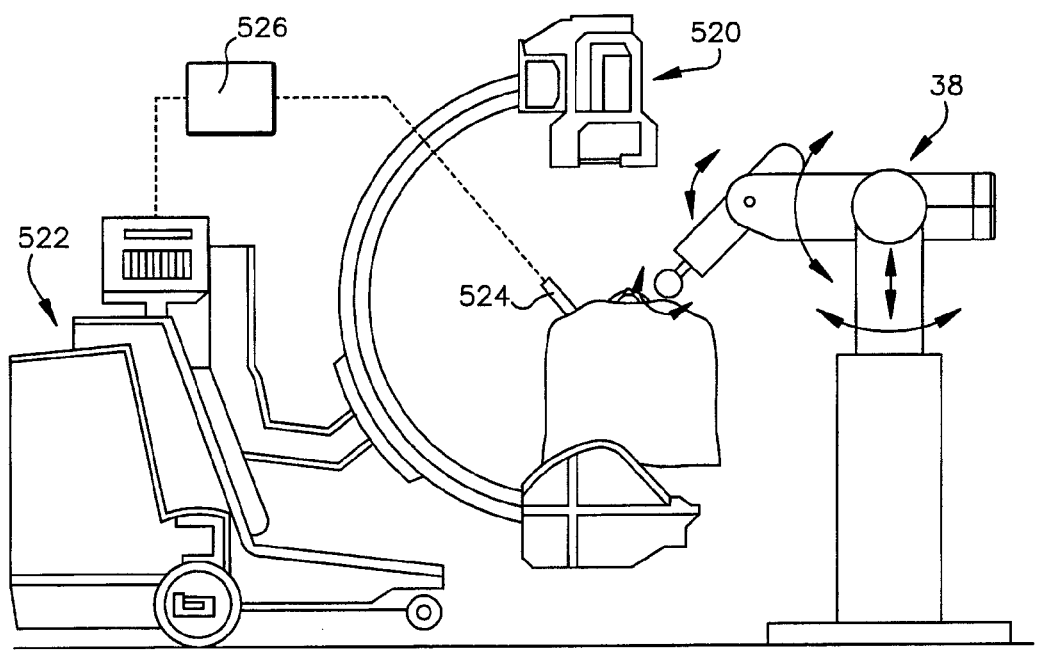
FIG. 37 is a schematic illustration depicting the manner in which a fluoroscope is utilized in association with an endoscope and a robotic mechanism during the securing of body tissue in any one of the ways illustrated in FIGS. 2 through 32.

The robotic mechanism 38 may be utilized with a fluoroscope 520 (FIG. 37). The general construction and mode of operation of the fluoroscope 520 and an associated control unit 522 is the same as is disclosed in U.S. Pat. Nos. 5,099, 859; 5,772,594; 6,118,845 and/or U.S. Pat. No. 6,198,794. The output from an endoscope 524 is transmitted to a computer 526. An image resulting from operation of the fluoroscope 520 is transmitted from the control unit 522 to the computer 526. This enables a monitor for the computer 526 to provide either two separate monoscopic, that is two dimensional, and/or a single stereoscopic or three dimensional view corresponding to the output from both the fluoroscope 520 and the endoscope 524. This may be done by having the computer 526 connected with two monitors, corresponding to the monitors 48 and 508 of FIG. 36.

The three dimensional image provided by the monitor connected with the computer 526 results from a combining of images obtained with the endoscope 524 and fluoroscope 520. The three dimensional image enables a surgeon to have a clear view of a location in a patient's body where the robotic mechanism 38 is being utilized to perform a surgical procedure. Of course, the surgical procedure performed by the robotic mechanism 38 may involve the securing of body tissue and/or a scaffold containing viable tissue components with fasteners in the manner previously explained herein. Alternatively, the surgical procedure may involve the moving and/or dissecting of body tissue with one of the retractors of FIGS. 31-33. The cooperation between the fluoroscope 520 and endoscope 524 facilitates the performance of stereotactic surgical procedures utilizing the robotic mechanism 38.

If desired, an ultrasonic imaging device may be used with either or both of the fluoroscope 520 and endoscope 524. Images obtained with the ultrasonic imaging device may be used with images from the fluoroscope and/or endoscope to provide wither stereoscopic or monoscopic images at monitors which are visible to the surgeon and correspond to the monitors 48 and 508 of FIG. 36.

A magnetic resonance imaging unit 530 (FIG. 38) may be utilized in association with the robotic mechanism 38 during performance of a surgical procedure on the patient 34. The magnetic resonance imaging unit 530 (MRI) provides an image of a location where the surgical procedure is being performed in a patient's body. The portion of the robotic mechanism 38 exposed to a magnetic field generated during use of the magnetic resonance imaging unit 530 (MRI) is formed of non-magnetic materials. Thus, the portion of the robotic mechanism 38 which extends into the magnetic field of the magnetic resonance imaging unit 530 is formed of a material which does not respond to a magnetic field. These materials may include polymeric materials and metals which are not responsive to a magnetic field.

An endoscope 534 (FIG. 38) cooperates with the magnetic resonance imaging unit 530 (MRI) to provide for imaging of the location in the patient 34 where a surgical procedure is being conducted by the robotic mechanism 38. Nonmagnetic materials, primarily polymeric materials, may be used in the endoscope 534. A monitor 538 is disposed at a location where it is visible to the surgeon and is outside of a magnetic field resulting from operation of the magnetic resonance imaging unit 530. The monitor 538 is connected with a computer (not shown) which is connected with both the endoscope 534 and the magnetic resonance imaging unit 530.

The monitor 538 may provide the surgeon a stereoscopic image, that is, a three dimensional image, resulting from outputs of the magnetic resonance imaging unit 530 and the endoscope 534. Alternatively, the imaging unit 538 may provide one monoscopic image, that is, a two dimensional image corresponding to the output of the magnetic resonance imaging unit 530 and a second monoscopic image corresponding to the output of the endoscope 534. The endoscope 534 is constructed of non-magnetic materials which are not effected by the magnetic field of the magnetic resonance imaging unit 530.

Rather than using a magnetic resonance imaging unit 530 to provide an image in association with the endoscope 534, the image may be provided by computerized tomographic scanning and/or positron emission tomography. Regardless of which of the imaging devices is utilized to provide an image of the area where surgical procedure is being conducted, it is believed that it would be advantageous to utilize the robotic mechanism 38 to conduct the surgical procedure.

Markers

In order to facilitate a surgeon's visualization of the location of articles utilized during the performance of surgical procedures by the robotic mechanism 38, markers may be provided in association with the articles. The markers which are utilized in association with one or more articles should be readily detected in an image provided by an imaging unit associated with the robotic mechanism 38. When the endoscopes 40, 502, 504, 524 and/or 534 are associated with the robotic mechanism 38, the markers should be clearly visible in an image transmitted to a monitor, such as the monitor 48, 508, and/or 538 from one or more of the endoscopes. When the fluoroscope 520 (FIG. 27) is associated with the robotic mechanism 38, the markers should be clearly visible in images transmitted to a monitor from the fluoroscope and/or an associated endoscope. Similarly, when a magnetic resonance imaging unit 530 (FIG. 38) is associated with the robotic mechanism 38, the markers should be clearly visible in an image transmitted to the monitor 538 from the magnetic resonance imaging unit.

To facilitate locating articles with the endoscopes 40, 502, 504, 524, and/or 534, light reflective particles may be used as markers. The light reflective particles are illuminated by light conducted along fiber optic pathways in the endoscopes. The light reflective particles may be embedded in the material of the anchor 60 and the suture retainer 72. Alternatively, a light reflective coating could be provided on the exterior of the anchor 60 and/or suture retainer 72. It is also contemplated that light reflective particles could be included in the material of the suture 66.

The staples 300 and 330 (FIGS. 21-26) may be provided with markers to facilitate locating the staples in an image from the endoscopes 40, 502, 504, 524 and/or 534. The markers may be reflective particles embedded in the material of the staple 300 or 330. Alternatively, a reflective coating could be provided on the staple 300 or 330. The reflective particles may be embedded in only the connector or bight portions 318 and 346 of the staples 300 and 330. Similarly, the coating of reflective material may be applied to only the connector or bight portions 318 and 346 of the staples 300 and 330.

In order to facilitate positioning of the scaffold 382 and viable tissue components 384, light reflective particles may be connected with portions of the scaffold 382. Thus, a marker formed of light reflective particle may be provided at each of the corners of the rectangular scaffold 382 illustrated in FIG. 29. Of course, if the scaffold 382 had a different configuration, light reflective particles would be provided at different locations on the scaffold. Regardless of the configuration of the scaffold 382, it is preferable to locate the light reflective particles adjacent to the periphery of the scaffold.

The light reflective particles may be disposed in small groups at spaced locations on the scaffold. Alternatively, the light reflective particles may be disposed in one or more threads which extend along one or more edges of the scaffold. The light reflective particles are formed of a substance which is compatible with the patient's body and reflects light. For example, polished titanium, gold, or platinum particles could be utilized. Alternatively, crystals which reflect light may be used as markers. The crystals may be formed of a salt and dissolve in a patient's body.

When the markers are to be used with the fluoroscope 520 and endoscope 524, it is believed that it may be preferred to form the marker of a radiopaque material which is also reflective. For example, polished particles of titanium, would reflect light so as to be visible in an image transmitted from the endoscope 524 and would be radiopaque so as to be visible in an image transmitted from the fluoroscope 520. It is contemplated that the radiopaque and light reflective particles could be formed off of other materials if desired. For example, a particle which is radiopaque and another particle which is reflective may be utilized. The radiopaque particle would be visible in the image transmitted from the fluoroscope 520 and the reflective particle would be visible in an image transmitted from the endoscope 534.

The reflective radiopaque particles may be embedded in the material of the anchor 60 and suture retainer 72. In addition, the particles may be embedded in the material of the suture 66. Alternatively, the radiopaque and light reflective particles may be provided as a coating on at least a portion of the anchor 60, suture retainer 72 and/or suture 66.

When the robotic mechanism 38 of FIG. 37 is to be utilized in association with the fluoroscope 520 and endoscope 524 to position the scaffold 382, a light reflective and radiopaque marker may be connected with the scaffold. The light reflective and radiopaque marker may be formed by polished particles of titanium disposed at selected locations along the periphery of the scaffold 382. Alternatively, the marker could be formed of a combination of light reflective particles and radiopaque particles. The light reflective particles would be visible in images transmitted by the endoscope 524 and the radiopaque particles would be visible in images transmitted by the fluoroscope 520.

The magnetic resonance imaging unit 530 has a relatively strong magnetic field. Therefore, markers provided in association with articles to be used during performance of a surgical procedure to be imaged with the magnetic resonance imaging unit 530 cannot be formed of a magnetic or magnetizable material. Images transmitted to the monitor 538 from the magnetic resonance imaging unit 530 (FIG. 38) are readily visible if they have a relatively high water or hydrogen content. Therefore, capsules of Vitamin E may be associated with articles to be used during the performance of surgery by the robotic mechanism 38 and imaging with the magnetic residence imaging unit 530. These capsules may be connected with the article or may be embedded in the article. When the capsules are to be embedded in the article, it is believed that it may be preferred to utilize relatively small microcapsules which will not significantly impair the strength of the materials in which they are embedded. The microcapsules may contain Vitamin E, water, or air.

The microcapsules may be embedded in the material of the anchor 60 and/or suture retainer 72. The microcapsules may also be embedded in the material of the staples 300 and 330. This would enable the anchor 60, suture retainer 72 and/or staples 300 and 330 to be readily visible in an image transmitted from the magnetic resonance imaging unit 530.

When articles are to be imaged with the magnetic resonance imaging unit 530, the articles may be marked by a coating of hydrophilic material. The coating of hydrophilic material absorbs body liquid and increases the contrast between the articles and the surrounding environment. For example, the staple 300 (FIGS. 21 and 22) and/or the staple 330 (FIGS. 23-26) may be coated with hydrophilic material. The areas of the staples which are to be bonded together, that is, the end portions 302 and 304 of the staple 300 and the side surfaces of the legs 342 and 344 of the staple 330 (FIGS. 24 and 26), may be left free of the hydrophilic material to promote a formation of a bond between the legs of the staple. They hydrophilic material may be a jell formed of materials such as algin, vegetable gums, pectins, starches, and/or of complex proteins such as gelatin and collagen.

The scaffold 382 may have one or more fibers formed of a hydrophilic material. Alternatively, small bodies of hydrophilic material could be positioned at various locations along the periphery of the scaffold 382. It is contemplated that the entire scaffold 382 could be formed a hydrophilic material, such as collagen.

A marker which is to be used with an endoscope 40, 502, 504, 524, and/or 534 may be a luminescent material. The luminescent material may be in the form of crystals such as zinc or cadmium sulfide. Alternatively, the luminescent material may be a dye. The marker may have chemiluminescence, bioluminescence, photoluminescence or triboluminescence.

The luminescent material forming a marker may be disposed on the surface of the anchor 60, suture retainer 72, and/or the suture 66. It is contemplated that the luminescent material forming a marker may form a coating over a portion of either the staple 300 (FIGS. 21 and 22) or the staple 330 (FIGS. 23-26).

It is contemplated the markers for use with the endoscopes 40, 502, 504, 524 and/or 534 may be used with fasteners other than the particular fasteners enclosed herein. Thus, one or more of the various markers previously described herein may be utilized in connection with a bonded rivet of the type disclosed in U.S. Pat. No. 6,203,565. Of course, the makers may be used in association with any of the other surgical implants disclosed in the aforementioned U.S. Pat. No. 6,203, 565.

The markers previously described herein may be utilized with any one of the expandable retractor assemblies 392, 410, or 422 (FIGS. 31-33) to indicate the positions of the retractor assemblies in an image on a monitor visible to a surgeon. The markers may be positioned on the balloons or bladders in the retractor assemblies 392, 410 and 422. Thus, a marker may be provided on the balloon or bladder 402 in the retractor assembly 392.

Figure 38:
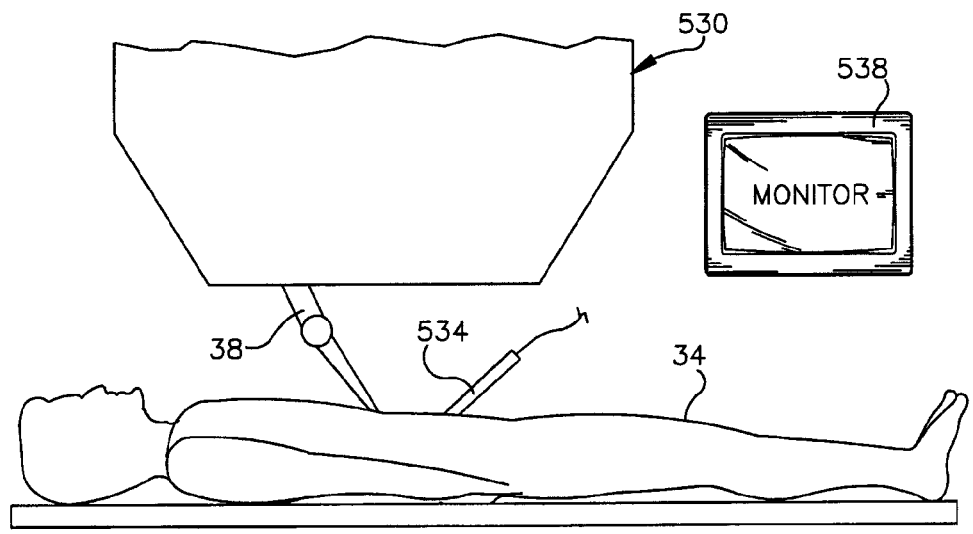
FIG. 38 is a schematic illustration depicting the manner in which the robotic mechanism of FIG. 1 is utilized, with a magnetic resonance imaging unit (MRI) and an endoscope, to secure body tissue in any one of the ways illustrated in FIGS. 2 through 32.

The marker on the balloon or bladder 402 (FIG. 31) may be light reflective so as to be detectable in an image provided by an endoscope 40 (FIG. 1). The marker on the balloon or bladder 402 may also be radiopaque so as to be detectable in an image provided by a fluoroscope 520 (FIG. 37). It is contemplated that a layer or coating of hydrophilic material could be provided on the balloon or bladder 402 to facilitate detection of the balloon or bladder in an image provided by the magnetic resonance imaging unit 530 (FIG. 38).

CONCLUSION

In view of the foregoing description, it is clear that the present invention relates to a method of securing either hard or soft body tissue. A robotic mechanism 38 or manual effort may be used to position a fastener relative to the body tissue. The fastener may be a suture 66, staple 300 or 330, screw 440, or other known device.

The fastener may be a suture 66 which is tensioned with a predetermined force by a robotic mechanism 38 or manual effort. The robotic mechanism 38 or manual effort may also be used to urge a retainer 72 toward body tissue 64 with a predetermined force. The suture 66 may be gripped with the retainer 72 while the suture is tensioned with a predetermined force and while the retainer is urged toward the body tissue 64 with a predetermined force.

Alternatively, the fastener may be a staple 300 or 330. A robotic mechanism 38 or manual effort may be utilized to position the staple relative to body tissue. The robotic mechanism 38 or manual effort may effect a bending of the staple 300 or 330 to move legs of the staple into engagement with each other. The legs of the staple 300 or 330 may be bonded together at a location where the legs of the staple are disposed in engagement.

Regardless of what type of fastener is utilized, a positioning apparatus 200 may be used to position the body tissue 64 before and/or during securing with a fastener. The positioning apparatus may include a long thin member 202 which transmits force to the body tissue. Force may be transmitted from an expanded end portion 204 of the long thin member 202 to the body tissue 64. A second member 232 may cooperate with the long thin member 202 to grip the body tissue. The long thin member 202 may be positioned relative to the body tissue by a robotic mechanism 38 or manual effort.

Various imaging devices may be utilized to assist in positioning a fastener, such as a rivet suture or staple, relative to body tissue. Under certain circumstances at least, it may be desirable to utilize two or more different types of imaging devices. Thus, an endoscope 534 and a magnetic resonance imaging apparatus (MRI) 530 may be utilized to provide an image. Alternatively, an endoscope 524 and a fluoroscopic device 520 may be utilized. If desired, ultrasonic imaging devices may be utilized in association with another imaging device, such as an endoscope or magnetic resonance imaging device. One or more markers may be provided on fasteners to facilitate location of the fasteners in an image.

A fastener (FIG. 5, 22, or 26) may be utilized to secure a scaffold 382 containing viable tissue components 384 in place on body tissue 334. The tissue components 384 may be stem cells, fetal cells, mesenchymal cells, and/or any desired type of precursor cells. It is contemplated that the scaffold 382 with one or more different types of tissue components may be positioned at any desired location within a patient's body, such as within an organ, by the robotic mechanism 38. For example, the scaffold 382 could be positioned in the pancreas or liver of a patient. Alternatively, the scaffold 382 could be connected with a bone in the patient's body. The scaffold 382 may be positioned relative to the body tissue by the robotic mechanism 38 or manual effort. One or more markers may be provided on the scaffold to facilitate location of the scaffold in an image.

It is contemplated that the robotic mechanism 38 may advantageously be utilized to position surgical implants other than fasteners in a patient's body. For example, the robotic mechanism 38 may be utilized to position a prosthesis 470 in a patient's body. If desired, the robotic mechanism 38 may be utilized to position a screw type fastener 440 at a specific location in a patient's body. The robotic mechanism 38 may be used to position a scaffold 382 containing viable tissue components relative to body tissue.

What is claimed is:

1. A robotic fastening system comprising:
   a robotic mechanism including an adaptive arm configured to position a staple relative to a body portion of a patient;
   a robotic arm interface configured to operate the adaptive arm of the robotic mechanism;
   a staple having first and second legs;
   a fastening member coupled to the adaptive arm, the fastening member having first and second force transmitting portions and configured to secure the body portion with the staple by applying a force from the first and second force transmitting portions to move the first and second legs of the staple toward each other;
   at least one of a position sensor configured to indicate a distance moved by the staple and a force measurement device configured to indicate a resistance required to move the staple relative to the body portion; and
   a tissue retractor assembly coupled to the robotic mechanism, the tissue retractor assembly including a cannula configured to facilitate insertion of the fastening member through the cannula into a working space inside the patient.

2. The system of claim 1, further comprising a visual readout configured to enable a user to determine a magnitude of tension on the staple.

3. The system of claim 1, wherein the staple is formed of a polymeric material.

4. A robotic fastening system comprising:
   a robotic mechanism including an adaptive arm configured to position a staple relative to a body portion of a patient;
   a robotic arm interface configured to operate the adaptive arm of the robotic mechanism;
   an endoscope coupled to the adaptive arm;

an imaging device configured provide an image, from the endoscope, of the staple relative to the body portion;

a staple having first and second legs;

a fastening member coupled to the adaptive arm, the fastening member having first and second force transmitting portions and configured to secure the body portion with the staple based on a location of tissue determined with the image provided by the endoscope by applying a force from the first and second force transmitting portions to move the first and second legs of the staple toward each other; and at least one of a position sensor configured to indicate a distance moved by the staple and a force measurement device configured to indicate a resistance required to move the staple relative to the body portion.

5. The system of claim 4, wherein the staple is formed of a polymeric material.

6. A robotic fastening system comprising:

a robotic mechanism including an adaptive arm with an inserter member configured to position a staple relative to a body portion of a patient;

a staple having first and second legs;

the inserter member having a passage extending through at least a portion of the inserter member, the passage being configured to receive the staple in at least a portion of the passage;

a pusher member disposed in at least a portion of the inserter member and configured to move along the passage of the inserter member to urge the staple toward the body portion and apply a predetermined force to the staple to at least one of deflect and bend the first and second legs of the staple; and a computer coupled to the robotic mechanism, the computer configured to determine the predetermined force applied by the pusher member based on the body portion.

7. The system of claim 6, wherein the staple is formed of a polymeric material.

* * * * *

(12) INTER PARTES REVIEW CERTIFICATE (3188th)
United States Patent
Bonutti

(10) Number: US 9,192,395 K1
(45) Certificate Issued: Jul. 17, 2023

(54) ROBOTIC FASTENING SYSTEM

(71) Applicant: Peter M. Bonutti

(72) Inventor: Peter M. Bonutti

(73) Assignee: P TECH, LLC

Trial Number:
  IPR2020-00649 filed Feb. 26, 2020

Inter Partes Review Certificate for:
  Patent No.: 9,192,395
  Issued: Nov. 24, 2015
  Appl. No.: 13/888,957
  Filed: May 7, 2013

The results of IPR2020-00649 are reflected in this inter partes review certificate under 35 U.S.C. 318(b).

INTER PARTES REVIEW CERTIFICATE
U.S. Patent 9,192,395 K1
Trial No. IPR2020-00649
Certificate Issued Jul. 17, 2023

AS A RESULT OF THE INTER PARTES REVIEW PROCEEDING, IT HAS BEEN DETERMINED THAT:

Claims 1 and 4 are cancelled.

\* \* \* \* \*